United States Patent
Alhimiri

(10) Patent No.: US 10,417,381 B2
(45) Date of Patent: Sep. 17, 2019

(54) RATING SYSTEM, PROCESS AND PREDICTIVE ALGORITHMIC BASED MEDIUM FOR TREATMENT OF MEDICAL CONDITIONS AND INCLUDING WORKMAN COMPENSATION AND GENERAL REHABILITATION MODULES FOR OPTIMIZING CARE PROVIDER EFFICIENCIES AND EXPEDITED TREATMENT FOR ACHIEVING HIGHER PATIENT FUNCTIONAL OUTCOMES AND LOWER COST

(71) Applicant: Ali Alhimiri, Allen Park, MI (US)

(72) Inventor: Ali Alhimiri, Allen Park, MI (US)

(*) Notice: Subject to any disclaimer, the term of this patent is extended or adjusted under 35 U.S.C. 154(b) by 576 days.

(21) Appl. No.: 15/177,903

(22) Filed: Jun. 9, 2016

(65) Prior Publication Data
US 2016/0292371 A1   Oct. 6, 2016

Related U.S. Application Data

(63) Continuation-in-part of application No. 14/737,212, filed on Jun. 11, 2015, now Pat. No. 9,734,478, which
(Continued)

(51) Int. Cl.
*G06F 19/00*   (2018.01)
*G16H 50/20*   (2018.01)

(52) U.S. Cl.
CPC .......... *G06F 19/328* (2013.01); *G16H 50/20* (2018.01)

(58) Field of Classification Search
None
See application file for complete search history.

(56) References Cited

U.S. PATENT DOCUMENTS 2,647,727 A   8/1953   Edwards
4,645,006 A   2/1987   Tinsley
(Continued)

FOREIGN PATENT DOCUMENTS

CN   102654890 A   9/2012
CN   102947857 A   2/2013
(Continued)

OTHER PUBLICATIONS

International Search Report and Written Opinion of the International Searching Authority, dated Oct. 28, 2016.
(Continued)

*Primary Examiner* — Michael Tomaszewski
*Assistant Examiner* — Jay M. Patel
(74) *Attorney, Agent, or Firm* — Dinsmore & Shohl LLP

(57) ABSTRACT

The present invention discloses a system, method and non-transitory software based computer writeable medium usable with a processor driven device for optimizing the diagnosis, treatment and resolution of worker injury events, such as associated with a workman compensation claim, and which improves upon the existing paper based module by synthesizing, in a digital environment, symptom, treatment and progress variables in a multi-party available format. A further related rehabilitation module, such as not limited to a worker injury event but also including any injury event associated with a typical accountable care organization (insurer/other payor/etc.) in a general health application is provided for establishing and tracking a patient's functional independent (FEM) measurement score. As with the workman compensation module, the rehabilitation module integrates the establishment of current conditions, achievable goals, and time based tracking of the patient treatment (including time elapsed changes in response to flat line response indicating a non-effective treatment plan) in order
(Continued)

to define a patient goal outcome and to optimize real time treatment and progress tracking to that goal.

14 Claims, 57 Drawing Sheets

Related U.S. Application Data is a continuation-in-part of application No. 14/495,378, filed on Sep. 24, 2014, now Pat. No. 9,734,512.

(60) Provisional application No. 61/883,004, filed on Sep. 26, 2013.

(56) References Cited

U.S. PATENT DOCUMENTS

| | | | |
|---|---|---|---|
| 5,583,758 A | 12/1996 | McIlroy et al. | |
| 6,253,861 B1 | 7/2001 | Carmichael et al. | |
| 6,732,793 B1 | 5/2004 | Lee | |
| 6,820,697 B1 | 11/2004 | Churchill | |
| 6,915,265 B1* | 7/2005 | Johnson | G06F 19/328 705/2 |
| 7,055,605 B2 | 6/2006 | Howlett et al. | |
| 7,113,940 B1 | 9/2006 | Jensen | |
| 7,347,288 B2 | 3/2008 | Lee | |
| 7,347,289 B2 | 3/2008 | Lee | |
| 7,363,240 B1 | 4/2008 | Armentano et al. | |
| 7,387,165 B2 | 6/2008 | Lopez de Cardenas et al. | |
| 7,395,216 B2 | 7/2008 | Rosenfeld et al. | |
| 7,416,029 B2 | 8/2008 | Telfer et al. | |
| 7,613,590 B2* | 11/2009 | Brown | A61B 5/0002 702/188 |
| 7,624,027 B1* | 11/2009 | Stern | G06Q 10/10 705/2 |
| 7,668,733 B2* | 2/2010 | Glimp | G16H 10/20 705/2 |
| 7,693,727 B2 | 4/2010 | Moore | |
| 7,716,069 B2* | 5/2010 | Ulrich | G06Q 10/10 705/3 |
| 7,716,070 B2* | 5/2010 | Glimp | G06F 19/363 705/2 |
| 7,720,692 B2* | 5/2010 | Glimp | G06Q 50/22 705/2 |
| 7,925,519 B2 | 4/2011 | Greene | |
| 8,086,471 B2 | 12/2011 | Gamboa et al. | |
| 8,117,047 B1 | 2/2012 | Cusimano-Reaston et al. | |
| 8,185,458 B2 | 5/2012 | Schmotzer | |
| 8,214,230 B1* | 7/2012 | DiPiero | G06F 19/324 705/2 |
| 8,489,412 B1 | 7/2013 | Gliklich | |
| 8,521,555 B2* | 8/2013 | Adams | G06Q 10/06 705/2 |
| 8,645,166 B2 | 2/2014 | Bessette | |
| 2002/0123670 A1* | 9/2002 | Goetzke | G06F 19/325 600/300 |
| 2002/0123906 A1* | 9/2002 | Goetzke | G06Q 50/22 705/2 |
| 2002/0128866 A1* | 9/2002 | Goetzke | G06Q 50/22 705/2 |
| 2002/0128867 A1* | 9/2002 | Goetzke | G06Q 50/22 705/2 |
| 2003/0087185 A1 | 5/2003 | Chung et al. | |
| 2003/0097185 A1* | 5/2003 | Goetzke | G16H 50/20 700/1 |
| 2004/0044546 A1 | 3/2004 | Moore | |
| 2004/0249701 A1 | 12/2004 | Schwarz | |
| 2006/0025931 A1 | 2/2006 | Rosen et al. | |
| 2006/0253304 A1 | 11/2006 | David | |
| 2006/0287879 A1* | 12/2006 | Malone | G06Q 10/1057 705/2 |
| 2007/0118399 A1* | 5/2007 | Avinash | G06F 19/328 705/2 |
| 2008/0033751 A1* | 2/2008 | Greene | G06F 19/328 705/2 |
| 2008/0114618 A1 | 5/2008 | Pysnik et al. | |
| 2008/0114689 A1 | 5/2008 | Psynik et al. | |
| 2010/0094657 A1* | 4/2010 | Stern | G06Q 10/10 705/3 |
| 2010/0198755 A1* | 8/2010 | Soll | G06F 19/324 706/11 |
| 2011/0118555 A1 | 5/2011 | Dhumne et al. | |
| 2011/0119077 A1 | 5/2011 | Gice et al. | |
| 2012/0030128 A1 | 2/2012 | Nelson et al. | |
| 2012/0109689 A1 | 5/2012 | Lee | |
| 2012/0284052 A1* | 11/2012 | Saukas | G06Q 10/00 705/3 |
| 2012/0303381 A1* | 11/2012 | Bessette | A61B 5/00 705/2 |
| 2013/0117033 A1* | 5/2013 | Mohlenbrock | G06Q 50/22 705/2 |
| 2013/0151281 A1* | 6/2013 | Kaburick | G06F 19/328 705/2 |
| 2013/0159023 A1* | 6/2013 | Srinivas | G06Q 50/22 705/4 |
| 2013/0246086 A1* | 9/2013 | Mun | G06Q 10/067 705/2 |
| 2014/0089010 A1 | 3/2014 | McKee et al. | |
| 2014/0108030 A1 | 4/2014 | Tejeda-Monteagut | |
| 2014/0114874 A1 | 4/2014 | Nelson et al. | |
| 2014/0136233 A1 | 5/2014 | Atkinson et al. | |
| 2014/0244291 A1 | 8/2014 | Bonner et al. | |
| 2015/0088628 A1 | 3/2015 | Alhimiri | |

FOREIGN PATENT DOCUMENTS

| | | |
|---|---|---|
| JP | 10021298 A | 1/1998 |
| WO | 2004022907 A1 | 3/2004 |
| WO | 2004088091 A1 | 10/2004 |
| WO | 2004106694 A1 | 12/2004 |

OTHER PUBLICATIONS

David West et al., "ReHap: Rehabilitation Healthcare Analytics Platform, Computer Integrated Surgery II Spring 2015", Technology Innovation Center, Engineering Research Center for Computer Integrated Surgical Systems and Technology, including appended screenshot showing Internet Publication Date of May 4, 2017, 2 pages total.

David West et al., "Rehabilitation Healthcare Analytics Platform: A Johns Hopkins Technology Innovation Center Project, Computer Integrated Surgery II Spring 2016", Johns Hopkins University, including appended screenshot showing Internet Publication Date of May 4, 2017, 8 pages total.

David West et al., Rehabilitation Healthcare Analytics Platform: Project 11 Final Report, EN.600.446, including appended screenshot showing Internet Publication Date of May 4, 2017, 13 pages total.

"Clinician-Developed System Triages Patients for Therapy", INSIGHT: Tapping Innovative Solutions & Technology at Johns Hopkins Medicine, Johns Hopkins Medicine Marketing and Communications, May 1, 2016, 2 pages total.

International Preliminary Report on Patentability dated Dec. 21, 2017 in International Application No. PCT/US2016/036870 (9 pages total).

Mafi et al., Worsening trends in the management and treatment of back pain, JAMA Internal Medicine, Sep. 23, 2013; 1573-1581, 173(17), doi: 10.1001/jamainternmed.2013.8992, Retrieved from http://archinte.jamanetwork.com/article.aspx?articleid=1722522.

Dr. Krishnaj Gourab et al., "Featured TIC Clinical Innovation Leads", John Hopkins Medicine Technology Innovation Center, including appended screenshot showing Internet Publication Date of May 2, 2017, 2 pages total. https://issuu.com/jasminemcneil/docs/ar_2016_print.

"ReHap: Rehabilitation Healthcare Analytics Platform", Project 11 main page, CIIS Lab, John Hopkins University, including appended screenshot showing Internet Publication Date of May 4, 2017, 2

(56) References Cited

OTHER PUBLICATIONS pages total. https://ciis.lcsr.jhu.edu/dokuwiki/doku.php?id=courses:446:2016:446-2016-11:project_11_main_page.
David West et al., "ReHAP", CIS 2, Spring 2015, Engineering Research Center for Computer Integrated Surgical Systems and Technology, including appended screenshot showing Internet Publication Date of May 4, 2017, 5 pages total. https://ciis.lcsr.jhu.edu/dokuwiki/lib/exe/fetch.php?media=courses:446:2016:446-2016-11:cis_2_poster_teaser_template_2015-rehap.pdf.
"ReHap: Rehabilitation Healthcare Analytics Platform", CIS project plan slides, John Hopkins Medicine Technology Innovation Center, including appended screenshot showing Internet Publication Date of May 4, 2017, 35 pages total. https://ciis.lcsr.jhu.edu/dokuwiki/lib/exe/fetch.php?media=courses:446:2016:446-2016-11:rehap-cis-projectplan.pdf.
"ReHap: Rehabilitation Healthcare Analytics Platform", Checkpoint Presentation slides, John Hopkins Medicine Technology Innovation Center, including appended screenshot showing Internet Publication Date of May 4, 2017, 24 pages total. https://ciis.lcsr.jhu.edu/dokuwiki/lib/exe/fetch.php?media=courses:446:2016:446-2016-11:rehap-cis-checkpoint.pdf.
"ReHAP Schema", Development Team, Mar. 24, 2016, including appended screenshot showing Internet Publication Date of May 4, 2017, 2 pages total. https://ciis.lcsr.jhu.edu/dokuwiki/lib/exe/fetch.php?media=courses:446:2016:446-2016-11:rehapschema_1_.pdf.
David West et al., Computer Integrated Surgery II, Group 11: ReHAP, "Seminar Review of: Validity of the AM-PAC '6-Clicks' Inpatient Daily Activity and Basic Mobility Short Forms", including appended screenshot showing Internet Publication Date of May 4, 2017, 7 pages total. https://ciis.lcsr.jhu.edu/dokuwiki/lib/exe/fetch.php?media=courses:446:2016:446-2016-11:seminarreview-west.pdf.
Diane U. Jette et al., "Validity of the AM-PAC '6-Clicks' Inpatient Daily Activity and Basic Mobility Short Forms", Research Report, Physical Therapy Journal, vol. 94, No. 3, Mar. 2014, pp. 379-391, DOI: 10.2522/ptj.20130199 https://ciis.lcsr.jhu.edu/dokuwiki/lib/exe/fetch.php?media=courses:446:2016:446-2016-11:379.full.pdf.
Microsoft Computer Dictionary, Fifth Edition, 2002, Microsoft Press, p. 23.
Mind—A Brief Introduction, John R. Searle, 2004, Oxford University Press, pp. 62-67.
What is Thought, Eric Baum, The MIT Press, 2004, pp. 33-65.
Robotics, Science and Systems III, Wolfram Burgard, Oliver Brock, and Cyril Stachniss, The MIT Press, 2008, pp. 41-48.
Language and Mind, Chomsky, Oxford University Press, 2005, p. 62.
Computing the Mind, Shimon Edelman, Oxford University Press, 2008, pp. 26-31.
Noetics, Lawrence Krader, 2010, Peter Lang Publishing, pp. 551-553.
Britannica Consise Encyclopedia, Encyclopedia Britannica, 2006, p. 537.
Harvard Business Review, The Employer-Led Health Care Revolution by Patricia A. McDonald, Robert S. Mecklenburg, and Lindsay A. Martin, from the Jul.-Aug. 2015 Issue, 25 pages Publication Date: Jul. 1, 2015.

\* cited by examiner

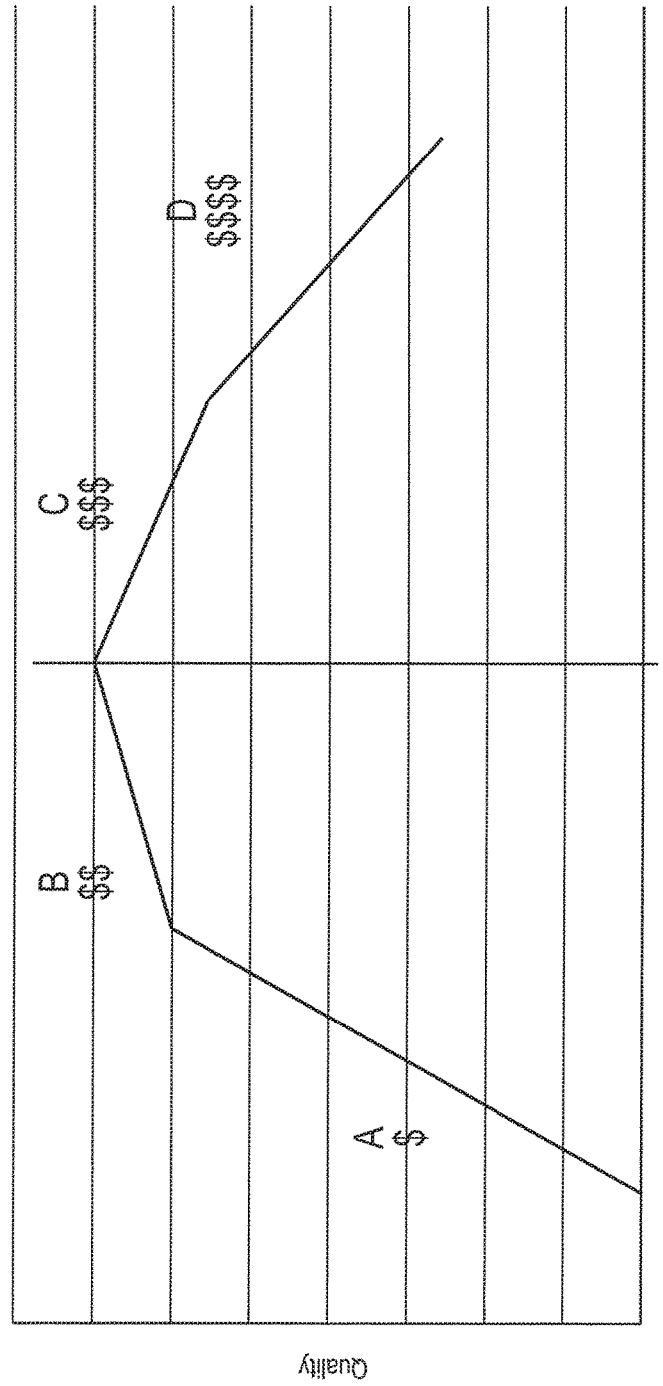

FIG. 4

ACO/SC Spine Program

| Metric/Year | SC percentile % Best Practice more> better | Value factor | % Best Practice index | SC Delta Functional Outcome disability rate less> better | Value factor | Functional Outcome disability rate index | SC Patient Satisfaction more> better | Value factor | Patient Satisfaction index | ACO $ Cost per all patient PMPM less> better | ACO $ Cost per spine patient PMPM less> better | ACO $ Cost average PMPM less> better | Value factor | $/Patient index | Total index per provider (should be less than 1) | 50/50 split PCP and non-PCP providers | Year end Savings |
|---|---|---|---|---|---|---|---|---|---|---|---|---|---|---|---|---|---|
| Providers | | | | | | | | | | | | | | | PCP minimum compliance rate for any saved savings is 80% (0.8) | | 300000 |
| PCPs | Fill out | | | Fill out | | | Fill out | | | | | Fill out | | | | | |
| AA | 95 | 0.5 | 0.5 | 10 | 0.2 | 0.2 | 80 | 0.1 | 0.1 | 20 | 8 | 14 | 0.2 | 0.1972 | 1 | 10655 | |
| BB | 100 | 0.5 | 0.475 | 40 | 0.2 | 0.18 | 75 | 0.1 | 0.08 | 30 | 3 | 16.5 | 0.2 | 0.1967 | 0.9322 | 9932.7 | |
| CC | 98 | 0.5 | 0.5 | 10 | 0.2 | 0.12 | 60 | 0.1 | 0.075 | 10 | 5 | 7.5 | 0.2 | 0.1985 | 0.8917 | 9501.1 | |
| DD | 99 | 0.5 | 0.49 | 40 | 0.2 | 0.18 | 90 | 0.1 | 0.06 | 8 | 12 | 10 | 0.2 | 0.198 | 0.9285 | 9893.2 | |
| EE | 96 | 0.5 | 0.495 | 20 | 0.2 | 0.12 | 90 | 0.1 | 0.09 | 24 | 8 | 16 | 0.2 | 0.1968 | 0.903 | 9621.5 | |
| FF | 99 | 0.5 | 0.48 | 10 | 0.2 | 0.16 | 95 | 0.1 | 0.095 | 19 | 10 | 14.5 | 0.2 | 0.1971 | 0.9318 | 9928.4 | |
| GG | 95 | 0.5 | 0.495 | 20 | 0.2 | 0.18 | 65 | 0.1 | 0.065 | 21 | 11 | 16 | 0.2 | 0.1968 | 0.9371 | 9984.9 | |
| HH | 97 | 0.5 | 0.475 | 50 | 0.2 | 0.16 | 40 | 0.1 | 0.04 | 20 | 16 | 18 | 0.2 | 0.1964 | 0.8718 | 9289.1 | |
| II | 50 | 0.5 | 0.485 | 30 | 0.2 | 0.1 | 20 | 0.1 | 0.02 | 22 | 5 | 13.5 | 0.2 | 0.1973 | 0.8014 | 8539.0 | |
| JJ | 97 | 0.5 | 0.25 | 50 | 0.2 | 0.14 | 80 | 0.1 | 0.08 | 26 | 3 | 14.5 | 0.2 | 0.1971 | 0.8121 | 8653.0 | |
| KK | 98 | 0.5 | 0.485 | 60 | 0.2 | 0.1 | 30 | 0.1 | 0.03 | 18 | 2 | 10 | 0.2 | 0.198 | 0.818 | 8715.9 | |
| LL | 100 | 0.5 | 0.49 | 20 | 0.2 | 0.08 | 50 | 0.1 | 0.05 | 23 | 4 | 13.5 | 0.2 | 0.1973 | 0.8973 | 9560.8 | |
| MM | 100 | 0.5 | 0.5 | 10 | 0.2 | 0.16 | 40 | 0.1 | 0.04 | 23 | 6 | 14.5 | 0.2 | 0.1971 | 0.8971 | 9558.7 | |
| NN | 99 | 0.5 | 0.495 | 50 | 0.2 | 0.18 | 20 | 0.1 | 0.02 | 17 | 5 | 11 | 0.2 | 0.1978 | 0.8628 | 9193.2 | |
| OO | 60 | 0.5 | 0.3 | 10 | 0.2 | 0.1 | 70 | 0.1 | 0.07 | 12 | 9 | 10.5 | 0.2 | 0.1979 | | 0.0 | |
| PP | 72 | 0.5 | 0.36 | 30 | 0.2 | 0.18 | 80 | 0.1 | 0.08 | 10 | 11 | 10.5 | 0.2 | 0.1979 | | 0.0 | |
| QQ | 98 | 0.5 | 0.49 | 20 | 0.2 | 0.14 | 70 | 0.1 | 0.07 | 22 | 13 | 17.5 | 0.2 | 0.1965 | 0.8665 | 9232.6 | |
| RR | 99 | 0.5 | 0.495 | 30 | 0.2 | 0.16 | 20 | 0.1 | 0.02 | 13 | 6 | 9.5 | 0.2 | 0.1981 | 0.8731 | 9302.9 | |
| SS | 95 | 0.5 | 0.475 | 20 | 0.2 | 0.14 | 40 | 0.1 | 0.04 | 12 | 4 | 8 | 0.2 | 0.1984 | 0.8534 | 9093.0 | |
| TT | 60 | 0.5 | 0.3 | 0 | 0.2 | 0.2 | 40 | 0.1 | 0.04 | 10 | 3 | 6.5 | 0.2 | 0.1987 | | 0.0 | |
| Total PCPs | | | | | | | | | | | | | | | 14.0778 | | |
| | | | | | | | | | | | | | | Units | 150000 | 150000.0 | |
| | | | | | | | | | | | | | | $ share | | | |
| | | | | | | | | | | | | | | $/unit | 10655.07395 | | |

FIG. 7

| Metric/Year | MODUS % Best Practice more> better | Value factor | % Best Practice Index | MODUS Functional Outcome Score | Value factor | Functional Outcome disability rate index | MODUS Patient Satisfaction more> better | Value factor | Patient Satisfaction index | Payers Cost Score | Value factor | $/Patient Index | Total Index per provider (should be less than 1) | Total Provider Year end Savings Available | Shared Savings 50/50 Split between PCP & Specialist | #1,2,3,4,5,6,7, 8,9,10,12,13,15, 16 |
|---|---|---|---|---|---|---|---|---|---|---|---|---|---|---|---|---|
| Providers |  |  |  |  |  |  |  |  |  |  |  |  |  |  |  |  |
| PCPs |  |  |  |  |  |  |  |  |  |  |  |  |  |  |  |  |
| AA | Fill out | 0.3 | 0.3 | Fill out | 0.3 | 0.3 | Fill out | 0.1 | 0.1 | Fill out | 0.3 | 0.3 | 1 | 300000 |  |  |
| BB | 95 | 0.3 | 0.285 | 70 | 0.3 | 0.09 | 80 | 0.1 | 0.08 | 50 | 0.3 | 0.285 | 0.74 |  | $7,903 |  |
| CC | 100 | 0.3 | 0.3 | 60 | 0.3 | 0.12 | 75 | 0.1 | 0.075 | 65 | 0.3 | 0.2805 | 0.7755 |  | $8,282 |  |
| DD | 98 | 0.3 | 0.294 | 40 | 0.3 | 0.18 | 60 | 0.1 | 0.06 | 50 | 0.3 | 0.285 | 0.819 |  | $8,747 |  |
| EE | 99 | 0.3 | 0.297 | 30 | 0.3 | 0.21 | 90 | 0.1 | 0.09 | 0 | 0.3 | 0.3 | 0.897 |  | $9,580 |  |
| FF | 96 | 0.3 | 0.288 | 65 | 0.3 | 0.105 | 95 | 0.1 | 0.095 | 65 | 0.3 | 0.2805 | 0.7685 |  | $8,208 |  |
| GG | 99 | 0.3 | 0.297 | 68 | 0.3 | 0.096 | 65 | 0.1 | 0.065 | 15 | 0.3 | 0.2955 | 0.7535 |  | $8,047 |  |
| HH | 95 | 0.3 | 0.285 | 72 | 0.3 | 0.084 | 40 | 0.1 | 0.04 | 0 | 0.3 | 0.3 | 0.709 |  | $7,572 |  |
| II | 97 | 0.3 | 0.291 | 85 | 0.3 | 0.045 | 20 | 0.1 | 0.02 | 50 | 0.3 | 0.285 | 0.641 |  | $6,846 |  |
| JJ | 97 | 0.3 | 0.291 | 69 | 0.3 | 0.093 | 30 | 0.1 | 0.03 | 65 | 0.3 | 0.2805 | 0.6945 |  | $7,417 |  |
| SS | 95 | 0.3 | 0.285 | 86 | 0.3 | 0.042 | 20 | 0.1 | 0.02 | 65 | 0.3 | 0.2805 | 0.6275 |  | $6,702 |  |
| TT | 28 | 0.3 | 0.084 | 32 | 0.3 | 0.204 | 70 | 0.1 | 0.07 | 65 | 0.3 | 0.2805 | 0.6385 |  | $6,819 |  |
| PMR |  |  |  |  |  |  |  |  |  |  |  |  |  |  |  |  |
| PMR1 | 95 | 0.3 | 0.0285 | 75 | 0.3 | 0.075 | 90 | 0.1 | 0.09 | 65 | 0.3 | 0.2805 | 0.474 |  | $16,843 |  |
| PMR2 | 100 | 0.3 | 0.03 | 83 | 0.3 | 0.051 | 85 | 0.1 | 0.085 | 15 | 0.3 | 0.2955 | 0.462 |  | $16,399 |  |
| Spine Surgeon |  |  |  |  |  |  |  |  |  |  |  |  |  |  |  |  |
| SS1 | 100 | 0.3 | 0.03 | 68 | 0.3 | 0.096 | 80 | 0.1 | 0.08 | 65 | 0.3 | 0.2805 | 0.487 |  | $17,287 |  |
| Chiropractor |  |  |  |  |  |  |  |  |  |  |  |  |  |  |  |  |
| Chiro1 |  | 0 | 0 | 75 | 0.3 | 0.075 | 75 | 0.1 | 0.075 | 65 | 0.3 | 0.2805 | 0.431 |  | $15,297 |  |
| Psychology |  |  |  |  |  |  |  |  |  |  |  |  |  |  |  |  |
| Psy1 |  | 0 | 0 | 65 | 0.3 | 0.105 | 80 | 0.1 | 0.08 | 65 | 0.3 | 0.2805 | 0.466 |  | $16,541 |  |
| Physical Therapy |  |  |  |  |  |  |  |  |  |  |  |  |  |  |  |  |
| PT1 |  | 0 | 0 | 80 | 0.3 | 0.06 | 75 | 0.1 | 0.075 | 50 | 0.3 | 0.285 | 0.420 |  | $14,924 |  |
| PT2 |  | 0 | 0 | 70 | 0.3 | 0.1 | 90 | 0.1 | 0.09 | 15 | 0.3 | 0.2955 | 0.476 |  | $16,896 |  |
| PT3 |  | 0 | 0 | 65 | 0.3 | 0.1 | 91 | 0.1 | 0.091 | 65 | 0.3 | 0.2805 | 0.477 |  | $16,932 |  |

Jack Payne's Recommendations
for their visit on 08/20/2014 at 6:10 PM.

Review of System for Spine Pain Report

Positive Responses

None

Negative Responses

Fever or Chills, Nightsweat, Headaches, History of Cancer, Recent Trauma, Recent Infection, Unintentional Weight Loss, Unintentional Weight Gain, Neck Pain, Back Pain, Joint or Limb Pain, Limited Range of Motion, Stiffness, Swelling, Numbness of Tingling, Loss of or Changed Sensation, Bladder of Bowel Problems, Localized Weakness, Impaired Balance, Tripping of Falling, Loss of Coordination, Paralysis, Stress of Any Kind, Anxiety or Depression, Disturbed Sleep, Blood in Urine, Blood in Stool, Abdominal Pain, Other Symptoms,

5,8,10,11, 12,14

130

Management

A purple flag indicates impaired patient function. It is recommended that a referral should be made to a PMR and that the patient be treated in your office using the options below.

Make A Referral

☐ PMR     ☐ Specialist

End Visit

Best Practice

Compliant — 132

Functional Score

Jack Payne's Recommendations
for their visit on 08/20/2014 at 6:14 PM.

Review of System for Spine Pain Report                #5,8,10,11,
                                                          12,14

Positive Responses

None

Negative Responses

Fever or Chills, Nightsweat, Headaches, History of Cancer, Recent Trauma, Recent Infection, Unintentional Weight Loss, Unintentional Weight Gain, Neck Pain, Back Pain, Joint or Limb Pain, Limited Range of Motion, Stiffness, Swelling, Numbness of Tingling, Loss of or Changed Sensation, Bladder of Bowel Problems, Localized Weakness, Impaired Balance, Tripping of Falling, Loss of Coordination, Paralysis, Stress of Any Kind, Anxiety or Depression, Disturbed Sleep, Blood in Urine, Blood in Stool, Abdominal Pain, Other Symptoms,

164

Management

A red flag has been raised. It is recommended that a referral should be made.

A red flag may also indicate an emergency. Can the patient wait for 2 business days?

● Yes    ○ No

166

Suspected Diagnosis:

| Best Practice | End Visit |

Compliant

Functional Score

Review of System for Spine Pain

John Doe  08/26/1981  322 — Spine

Search  Dr.'s Name

320 — Step 1 of 3   258   316 — Start Over

The following questions will help us narrow your diagnosis. Please select all complaints that apply to you.

- 260 — Night sweat:
- 262 — Fever or chills:
- 264 — History of cancer:
- 266 — Recent infection:
- 268 — Recent trauma:
- 270 — Impaired balance:
- 272 — Poor coordination:
- 274 — Tripping or falling:
- 276 — Loss or changed sensation:
- 278 — Numbness or tingling sensation:
- 280 — Localized weakness:
- 282 — Paralysis:
- 284 — Neck pain:
- 286 — Back Pain:
- 288 — Joint or limb pain:
- 290 — Stiffness:
- 292 — Limited range of motion:
- 294 — Swelling:
- 296 — Headaches:
- 298 — Anxiety or depression:
- 300 — Stress of any kind:
- 302 — Disturbed sleep:
- 304 — Unintentional weight loss:
- 306 — Blood in urine:
- 308 — Blood in stool:
- 310 — Bladder or bowel problems:
- 312 — Abdominal pain:
- 314 — Other symptoms:

318 — Next

FIG. 19A

Stress Level Questionnaire

John Doe    08/26/1981                                        ◯ Spine                    Search | & Dr.'s Name Step 2 of 3

Please help us determine your stress level.

Please read and answer the questions carefully. Do not take long to answer the questions, however it is important that you answer every question. There is always a BLANK for your particular situation.

Where do you have pain?  ☐ Arm ☐ Leg ☐ Lower back ☐ Neck ☐ Shoulder ☐ Other
                            324  326   328    330       332    334

You can select multiple.
● Yes
○ No
Auto, work, slip & fall, etc.                                            336

How many days of work have you missed because of pain during the past 18 months? [0 days]
                                                                          338
How long have you had your current pain problem?  [0 days]
                                                   340
What was your last day of work? [         ▼]

Here are some of the things that other people have told us about their pain. For each statement, select a number from 0 to 10 on the scale to say how much physical activities, such as bending, lifting, walking or driving would affect your pain.

342 — To what extent is your work either physically heavy or monotonous?  ● Not at all ─────────── Extremely
344 — How would you rate the pain that you have had during the past week?  ● No pain ─────────── Pain as bad as it could be
346 — In the past three months, on average, how bad was your pain on a 0-10 scale?  ● No pain ─────────── Pain as bad as it could be
    348 — How often would you say that you have experience pain episodes, on average, during the past three months?  ● Never ─────────── Always
350 — Based on all things you do to cope, or deal with your pain, on an average day, how much are you able to decrease it?  ● Can't decrease it at all ─────────── Can decrease it completely

FIG. 19B-1

352 — How tense or anxious have you felt in the past week? ● Absolutely calm and relaxed — As tense and anxious as I've ever felt How much have you been bothered by feeling depressed in the past week? ● Not at all — Extremely
354

In your view, how large is the risk that your current pain may become persistent? ● No risk — Very large risk
356

In your estimation, what are the chances that you will be able to work in six months? ● No chance — Very large chance
358

If you take into consideration your work routines, management, salary, promotion possibilities and work mates, how satisfied are you with your job? ● Not satisfied at all — Completely satisfied
360

362 — Physical activity makes my pain worse ● Completely disagree — Completely agree An increase in pain is an indication that I should stop what I'm doing until the pain decreases ● Completely disagree — Completely agree
364

366 — I should not do my normal work with my present pain. ● Completely disagree — Completely agree Here is a list of five activities. Select a number from 0 to 10 on the scale that best describes your current ability to participate in each of these activities.

268 — I can do light work for an hour. ● Can't do it because of pain problem

270 — I can walk for an hour. ● Can't do it because of pain problem

272 — I can do ordinary household chores. ● Can't do it because of pain problem

274 — I can do the weekly shopping. ● Can't do it because of pain problem

276 — I can sleep at night. ● Can't do it because of pain problem

⊖ Previous | Next ⊕
375         377

FIG. 19B-2

Functional Level Questionnaire

John Doe   08/26/1981   ⊘ Spine

Search   Dr.'s Name

Step 3 of 3

⟳ Start Over

Please help us determine your functional level.

378 — Pain Score ○———————————————————————
         No pain                                         Worst pain ever
380 — Pain Intensity  -Select- ▼
382 — Personal Care  -Select- ▼
384 — Lifting  -Select- ▼
386 — Walking  -Select- ▼
388 — Sitting  -Select- ▼
390 — Standing  -Select- ▼
392 — Sleeping  -Select- ▼
394 — Sex Life  -Select- ▼
396 — Social Life  -Select- ▼
398 — Traveling  -Select- ▼

⊕ Previous     ✓ Submit Questionnaires
       400                    402

FIG. 19C

Pertinent ROS Results

@ John Doe  08/26/1981  322 — 🦴 Spine  404 — [Search]  & Dr.'s Name

✓ Positive Responses — 406
- Loss or changes sensation in the legs — 408
- Numbing or tingling sensation in both legs — 410
- Back Pain — 412

? Unsure — 414
- Loss or changes sensation in the legs — 416

✗ Negative Responses — 418
- Night sweat — 420
- Fever or chills — 422
- History of cancer — 424
- Recent infection
- Recent trauma
- Impaired balance
- Poor coordination
- Tripping or falling
- Localized weakness
- Paralysis
- Neck pain
- Joint or limb pain
- Stiffness
- Limited range of motion
- Swelling
- Headaches
- Anxiety or depression
- Stress of any kind
- Disturbed sleep
- Unintentional weight loss
- Blood in urine
- Blood in stool
- Abdominal pain
- Other symptoms Pertinent HPI and Other History: 426
Pertinent Physical Examination: 428

430
[                    ]

Medical Decision Making 432
Do you suspect any of the following conditions?
434 — ☐Infection ☐Fracture ☐Cancer ☐Cauda Equina ☐Pending Paralysis
☐Weakness ☐Radiculopathy ☐Ankylosing Spondylitis 436 — [None.Continue]

| Supervisor Details | Injured Worker Details |

502 — Supervisor Name
504 — Company
506 — Position
508 — Email
510 — Phone
512 — Address 1
514 — Address 2
516 — City
518 — State
520 — Zip Code

| Supervisor Details | Injured Worker Details |

INJURED WORKER DETAILS

526 — Name  
528 — Date of Birth

Check for user 524  
530 — Email  
532 — Phone  
534 — Address 1  
536 — Address 2  
538 — City  
540 — State  
542 — Zip Code  
544 — INJURY DETAILS  
546 — Describe Injury 548 — Injury Date  
530 — Injury Time Enter below routine Job Duties

552

Submit  
Back  
554

FIG. 24

YOUR DOCTOR 1 ASSIGNMENT
Doctor 1 will be your primary care provider for your injury
John Smith, MD
Physical Medicine & Rehabilitation
12345 Your Street.
Your City, MI 48101
Phone: 888.123.4567
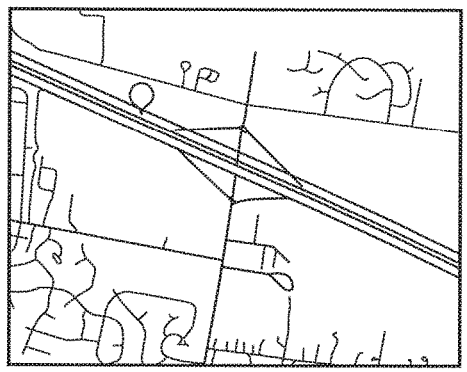
556
Continue
558
FIG. 25

| Worker Name: John Doe    Date of Birth: 11/13/1981 |

CONFIRM DETAILS

Welcome to Company X, please confirm and complete your details

| Personal Details | Injury Details |

PERSONAL DETAILS

- 562 — Patient Name: John Doe
- 564 — Date of Birth: 11 | 11 | 1969
- 566 — Last Four Social Security: 1238
- 568 — Email Address: john.doe@gmail.com
- 570 — Phone Number: 888.123.4567
- 572 — Address 1: 224 Your Street
- 574 — Address 2:
- 576 — City: Your City
- 578 — State: Your State
- 580 — Zip Code: 12345

560

Emergency Contact

- 582 — Name: Jane Doe
- 589 — Relationship: Wife
- 586 — Contact Number: 888.123.4567

Family Doctor

- 588 — Name:
- 590 — Contact Number:

Please create a password to access your account in the future

- 592 — Password:
- 594 — Retype Password:

Worker Name: John Doe    Date of Birth: 11/13/1981

CONFIRM DETAILS

Welcome to Company X, please confirm and complete your details

| Personal Details | Injury Details |

INJURY DETAILS

Please confirm and update your personal details as required

600 — Injury as described by your supervisor

John Dow was involved in a work place injury at our Westland wearhouse on 11.11.2015 at 1:20 pm
he fell off the loading dock when he tried to avoid hilo backing up
he stated that he has neck and right arm pain
Jack Wood
Shift Supervisor
11.11.2015

602 — Add your details of the injury

Below are duties recorded by your supervisor please review for accuracy and add your own detais if needed

598 —

| A | Lifting 20 lb every 1 hour | —600 |
| B | Driving a hilo 3 hours a day | —602 |
| C | Picking material off 3 hours a day | —604 |
| D | Cleaning containers | —606 |
| E | Rolling sheets | —608 |
| F | Typing on a computer | —610 |
| G | Walking between work stations | —612 |
| H | Managing inventory | —614 |
| I | Calling on staff members | —616 |
| J | Answering phone calls | —618 |
| K | 10 hours/day | —620 |
| L | 4 days a week | [+] —622 |

Submit
624

FIG. 27

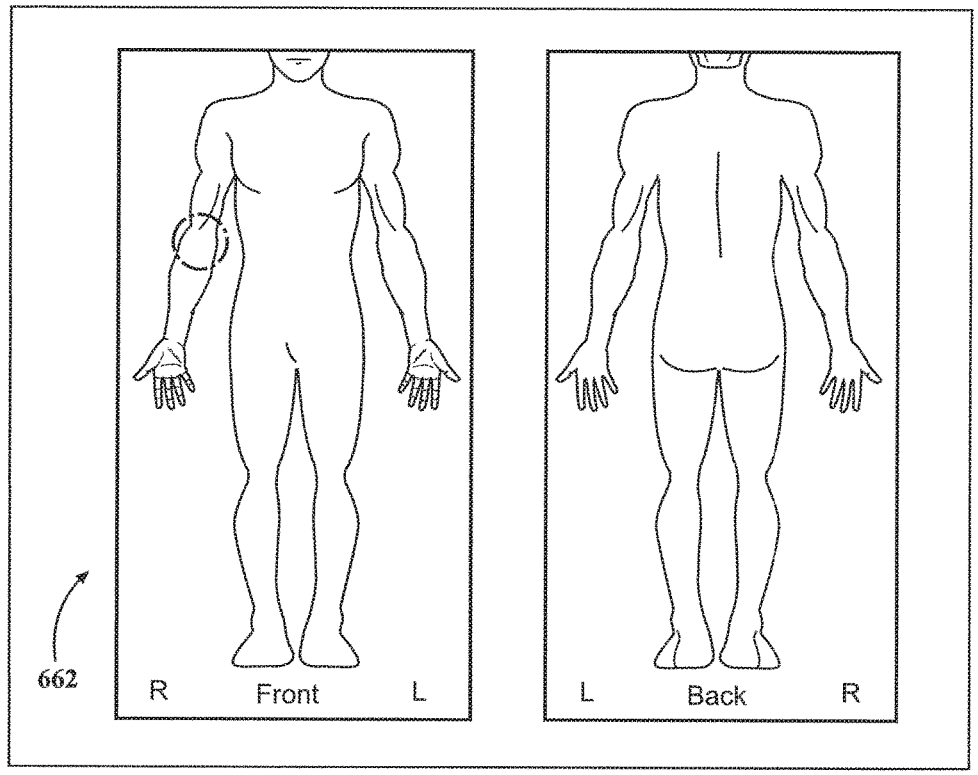
662  R  Front  L    L  Back  R
② Indicate Intensity — 636'
1  2  3  4  5  6  ○ 5  6  7  8  9  10
③ Type of Pain
☐ ⚡Aching  ☐ / Stabbing  ☐ ⟳ Burning  ☐ ZZ Numbness/Tingling
④ Comments: When did it start? What caused it? What makes it better or worse? Any other symptoms?
[+] Add Symptoms Area — 652
| Symptoms Area | | | |
|---|---|---|---|
| Location | Type | Intensity | Other Symptoms |
| | | | |
| | | | |
FIG. 29

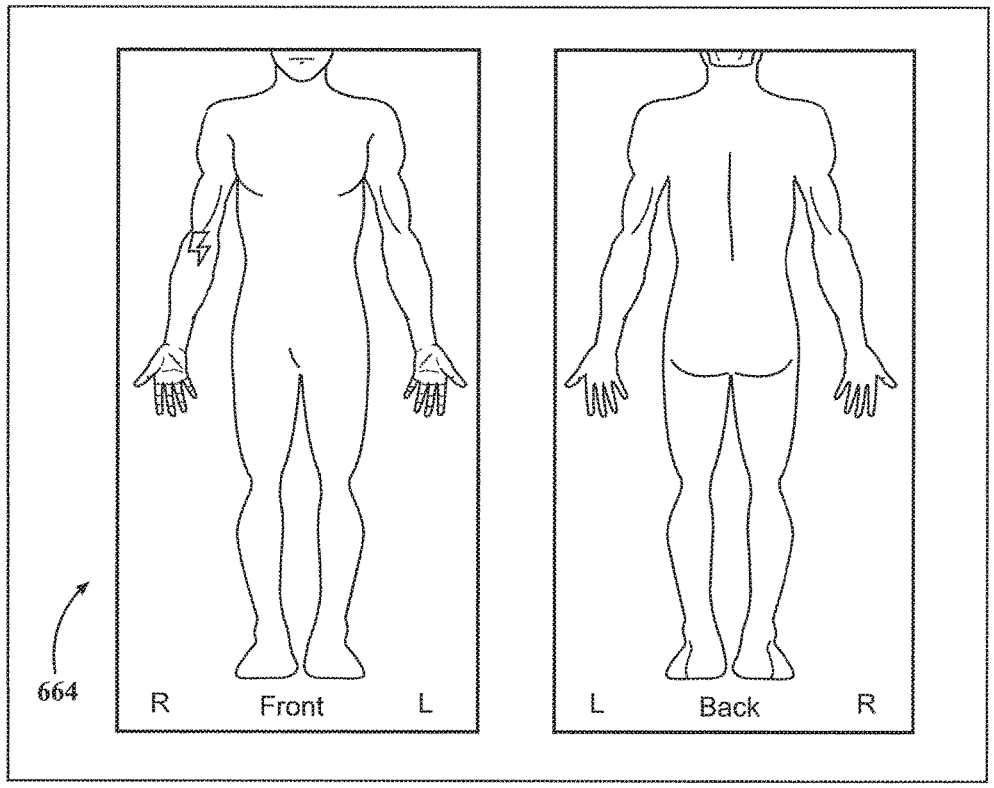
② Indicate Intensity
③ Type of Pain
☑ ⚡Aching  ☐ / Stabbing  ☐ ⟲ Burning  ☐ zZ Numbness/Tingling
└─640
④ Comments: When did it start? What caused it? What makes it better or worse? Any other symptoms?
[                                                                                    ]
[ + Add Symptoms Area ]
| Symptoms Area | | | |
|---|---|---|---|
| Location | Type | Intensity | Other Symptoms |
|  |  |  |  |
|  |  |  |  |
FIG. 30

| 668 | Symptoms Catalog | | | | | | | | | |
|---|---|---|---|---|---|---|---|---|---|---|
| | Injury | E1 | E2 | E3 | E4 | E5 | E6 | E7 | E8 | E9 | E10 |
| | Week | 1 | 1 | 2 | 3 | 5 | 8 | 11 | 14 | 20 | 28 |
| | | 02/01/2015 | 02/03/2015 | 02/05/2015 | 02/10/2015 | 02/16/2015 | 03/02/2015 | 03/24/2015 | 04/14/2015 | 05/05/2015 | 06/09/2015 | 08/04/2015 |

| 670 | Pain Record | | 682 | 684 |
|---|---|---|---|---|
| | Location 640 644 Type 646 | | Intensity | Comments |
| 672 | Neck | ⚡Aching 🔥Burning 💤Numbness/Tingling | ⑨ | Unable to sleep |
| 674 | Shoulder | ⚡Aching 🔥Burning 💤Numbness/Tingling | ⑩ | |
| 676 | Arm | ⚡Aching 🔥Burning 💤Numbness/Tingling | ⑩ | |
| 678 | Forearm | ⚡Aching 🔥Burning 💤Numbness/Tingling | ⑨ | |
| 680 | Hand | ⚡Aching 🔥Burning 💤Numbness/Tingling | ⑨ | |
| 681 | Head | ⚡Aching 🔥Burning 💤Numbness/Tingling | ⑨ | |

FIG. 31

○ John Doe    Date of birth: 1/24/1988

Ability Input (Worker)                                    Date: 16th January 2016

If you were at work today, how much effort will take you to complete your duties

| Duties | Effort % | 1-25 | 26-50 | 51-75 | 76-100 | >100 | Score |
|---|---|---|---|---|---|---|---|
| A. Lifting 20 lb every 1 hour | Patient Current Ability | Minimum | Moderate | Severe | Extreme | Unable | 3 |
| B. Driving a hilo 3 hours a day | Patient Current Ability | Minimum | Moderate | Severe | Extreme | Unable | 2 |
| C. Picking material off 3 hours a day | Patient Current Ability | Minimum | Moderate | Severe | Extreme | Unable | 4 |
| D. Cleaning containers | Patient Current Ability | Minimum | Moderate | Severe | Extreme | Unable | 5 |
| | | | | Current Ability | | | 3.5 |

[ Submit ]

FIG. 40

Date of birth: 1/24/1988

| | | 728 | 730 | 732 | 734 | | 738 |
|---|---|---|---|---|---|---|---|
| Ability Input (Worker) | | | | | | Date: 16th January 2016 | |
| If you were at work today, how much effort will take you to complete your duties | | | | | | | 736 |
| Duties | Effort % | 1-25 | 26-50 | 51-75 | 76-100 | >100 | Score |
| A. Lifting 20 lb every 1 hour | Patient Current Ability | Minimum | Moderate | Severe | Extreme | Unable | 3 |
| | Provider Goal Ability | Minimum | Moderate | Severe | Extreme | Unable | 4 |
| | Barrier to goal is uncontrolled pain. | | | | | | 746 |
| B. Driving a hilo 3 hours a day | Patient Current Ability | Minimum | Moderate | Severe | Extreme | Unable | 2 |
| | Provider Goal Ability | Minimum | Moderate | Severe | Extreme | Unable | 5 |
| | Add Comment | | | | | | |
| C. Picking material off 3 hours a day | Patient Current Ability | Minimum | Moderate | Severe | Extreme | Unable | 4 |
| | Provider Goal Ability | Minimum | Moderate | Severe | Extreme | Unable | 4 |
| | Add another comment here.. | | | | | | |
| | Edit | | | | | | |
| D. Cleaning containers | Patient Current Ability | Minimum | Moderate | Severe | Extreme | Unable | 5 |
| | Provider Goal Ability | Minimum | Moderate | Severe | Extreme | Unable | 5 |
| | Comments (optional) | | | | | | 740 |
| | | Current Ability | | | | | 3.5 |
| | | Goal Ability | | | | | 4.5 |
| | | Modus Ability Gap | | | | | 4.5 - 3.5 = 1 |
| | | | Submit | | | | |

FIG. 41

| F. Social Cognition 802 | Current Function | Ind | Mod1 | Sup | Min PA | Mod PA | Max PA | Total PA | 1 |
|---|---|---|---|---|---|---|---|---|---|
| | Goal Function | Ind | Mod1 | Sup | Min PA | Mod PA | Max PA | Total PA | 4 |
| | Prior Function | Ind | Mod1 | Sup | Min PA | Mod PA | Max PA | Total PA | 7 |

[Add Comment]

818 — 1. Is that patient/family willing to be in an impatient Rehab?
☐ Yes ☐ No

820 — 2. Is the patient/family willing to be in a Subacute Rehab?
☐ Yes ☐ No

822 — 3. Does the patient have the cognition to follow therapy instructions?
☐ Yes ☐ No 824 — 4. Can the patient sit for an hour or more in a chair?
☐ Yes ☐ No 826 — 5. Does the patient have a social support at home?
☐ Yes ☐ No 828 — 6. Enter all Acute diagnosis that the patient is being actively treated for:
☐ Yes ☐ No 830 — [Add]                                                                 832

| | | 839 |
|---|---|---|
| Current Function | 19 | |
| Goal Function | 30 | |

Modus Rehab Function Gap        30 - 19 = 11
                                    836

[Submit]
    838

FIG. 45B

RATING SYSTEM, PROCESS AND PREDICTIVE ALGORITHMIC BASED MEDIUM FOR TREATMENT OF MEDICAL CONDITIONS AND INCLUDING WORKMAN COMPENSATION AND GENERAL REHABILITATION MODULES FOR OPTIMIZING CARE PROVIDER EFFICIENCIES AND EXPEDITED TREATMENT FOR ACHIEVING HIGHER PATIENT FUNCTIONAL OUTCOMES AND LOWER COST

This application is a Continuation-in-part of application Ser. No. 14/737,212 filed on Jun. 11, 2015. Application Ser. No. 14/737,212 is a Continuation-in-part of application Ser. No. 14/495,378 filed on Sep. 24, 2014. Application Ser. No. 14/495,378 claims the benefit of U.S. Provisional Application 61/883,004 filed on Sep. 26, 2013, the contents of which are incorporated herein in their entirety.

BACKGROUND OF THE INVENTION

Field of the Invention

The present invention is generally directed to financial-bio-psycho social management models for optimal treatment of medical conditions. More particularly, the present invention discloses a system, process and, in particular, an improved algorithmic based non-transitory computer writeable medium for treatment of medical conditions in a cost effective fashion.

The system, process and associated algorithmic medium further includes a related module for optimizing the diagnosis, treatment and resolution of worker injury events, such as associated with a workman compensation claim, and which improves upon the existing paper based module by synthesizing, in a digital environment, symptom, treatment and progress variables in a multi-party available format. In particular, the injury event module greatly increases care provider (physician) efficiency by integrating and compiling electronically, in easily readable and time elapsed formats, symptom and treatment variables. The module additionally provides a reasonable and agreeable model, such as between the employer/payer and worker, for establishing minimal goals for facilitating return to work.

A further related rehabilitation module, such as not limited to a worker injury event but also including any injury event associated with a typical accountable care organization (insurer/other payor/etc.) in a general health application is provided for establishing and tracking a patient's functional independent (FEM) measurement score. As with the workman compensation module, the rehabilitation module integrates the establishment of current conditions, achievable goals, and time based tracking of the patient treatment (including time elapsed changes in response to flat line response indicating a non-effective treatment plan) in order to define a patient goal outcome and to optimize real time treatment and progress tracking to that goal.

In this fashion, the time frame between a worker injury event (or rehab setting reported event) and an eventual agreed to return to work event (or final rehab setting event) is minimized through the maximization of effectiveness of the treatment protocols, as well as the maximization of the efficiency of the care provider by synthesizing into a simplified and time interval dynamic record the critical variables associated with the treatment of the patient as derived from the best practices and critical pathway modules and as integrated into these specific applications.

Description of the Background Art

The prior art is documented with examples of systems and methods, such as utilized in the medical field. A first example of this is set forth in Moore, U.S. Pat. No. 7,693,727 which teaches interactive systems and methods for directing, integrating, documenting, and tracking steps taken by medical providers during the process of care for a patient's given condition. Doctors' actions are directed by a prescriptive protocol—a checklist of discrete steps designed for efficient or optimal care of an individual patient's specific condition. The step-by-step checklist is abstracted from decision tree guidelines for the optimal work up and treatment for the condition using probability-based methodology. The care protocols can be derived from widely available and non-proprietary guidelines and decision trees based on public medical research literature.

In one embodiment, the invention can be employed by a primary care clinician at the point of referral into the specialist sector, and at the specialist level when proposing a risky or expensive or otherwise problematic medical or surgical diagnostic or treatment intervention. At these two critical transaction points in care, the checklist functions like a lock, based on a hidden clinical decision algorithm (an explanation of which can be displayed upon request). The system asks the clinician for data and then generates the patient's optimal checklist, displaying it as a point and click form keyed to the stage of care being undertaken by each doctor. As the clinician enters data into the checklist, a decision engine determines whether the checklist data satisfies predetermined criteria for authorization of the proposed action. The system can also document each transaction taken in the process of care to create an electronic record that can be made accessible to all clinicians involved in the process of care.

Moore, US 2004/0044546 teaches interactive methods and systems for directing, integrating, documenting and tracking steps taken by medical providers during the process of care for a given patient's condition. Doctors' actions are directed by a prescriptive protocol—a checklist of discrete steps designed for efficient or optimal care of an individual patient's specific condition. The step-by-step checklist is abstracted from decision tree guidelines for the optimal work up and treatment for the condition using probability-based methodology. The care protocols can be derived from widely available and non-proprietary guidelines and decision trees based on public medical research literature.

In one embodiment, the invention can be employed by a primary care clinician at the point of referral into the specialist sector, and at the specialist level when proposing a risky or expensive or otherwise problematic medical or surgical diagnostic or treatment intervention. At these two critical transaction points in care, the checklist functions like a lock, based on a hidden clinical decision algorithm (an explanation of which can be displayed upon request). The system asks the clinician for data and then generates the patient's optimal checklist, displaying it as a point and click form keyed to the stage of care being undertaken by each doctor. As the clinician enters data into the checklist, a decision engine determines whether the checklist data satisfies predetermined criteria for authorization of the proposed action. The system can also document each transaction taken in the process of care to create an electronic record that can be made accessible to all clinicians involved in the process of care.

A further example of the prior art is the healthcare providing organization (HPO) model of Cusimano-Reaston et al., U.S. Pat. No. 8,117,047, and which teaches a preferred provider network (PPO) or other membership agreement that allows individuals or groups to join via a membership contract. The contract allows the HPO to provide a technical component of a medical evaluation or service. Additionally, the HPO employs or retains the services of healthcare professionals who participate in and monitor an evaluation of a patient who can be at a remote location from the healthcare professional. The HPO provides a medical diagnostic unit, which is known as an EFA-2, that allows the healthcare professional to receive data that pertains to the patient via a real-time communication protocol, or the patient data is collected and stored on an electronic storage device. The healthcare professional then analyzes the patient data and issues recommended treatment.

Lee, US 2012/0109689 teaches a support system for improved quality healthcare, defined as MEGICS (Medical+Logistics), developed in order to improve quality of care and enhance the efficiency of operation of healthcare facilities and providers. When front-line healthcare doctors and nurses make various clinical decisions, MEGICS management system provides them with relevant clinical knowledge in a timely manner with the stated objective being to increase user satisfaction and provide better quality of healthcare services.

Gliklich, U.S. Pat. No. 8,489,412, teaches a data processing system for determining clinical outcomes of medical data gathered by the system. A doctor defines a medical study and can administer and collect data relevant to that study in real time from potentially geographically diverse doctors, patients and other people associated with the study. The system can analyze the medical data in real-time according to any number of clinical algorithms that may be custom defined and edited before and during the study. The clinical algorithms produce clinical outcome data that can be used for treatment of patients participating in the study immediately after the data is input and analyzed. The medical outcomes can indicate such things as performance comparisons, composite outcomes, and risk stratification and assessments for such things as treatments, drugs, illnesses, doctors, patients and physicians groups.

McIlroy, U.S. Pat. No. 5,583,758, teaches a health care management system for use by hospitals, physicians, insurance companies, health maintenance organizations, and others in the health care field includes a processing unit and health condition guidelines. A user inputs information related to the health condition of an individual and guideline treatment options are identified. The user also inputs actual or proposed and final recommendation treatments for the same individual. The resulting comparative information can be used to modify the actual or proposed treatment, or provide explanatory information as to reasons for the difference between the final recommendation treatment and guideline treatment options. Also, the comparative information can be used by a reviewer for evaluation or utilization purposes.

Goetzke, US 2003/0097185, discloses a medical resource for chronic pain patients forecasted using a method or computer software product to improve accuracy in forecasting medical resources, decrease the time required to forecast medical resources, and many other benefits. Desired patient indicia including direct medical indicia, indirect medical indicia, and non-medical indicia are selected to serve as independent variables. At least one chronic pain indication is selected to serve as a dependent variable. A chronic pain forecasting model is created using the patient indicia and the chronic pain indication. The chronic pain forecasting model is applied to a chronic pain patient indicia to create a patient forecast. Many different embodiments of the chronic pain patient dynamic medical resources forecaster method and software product are possible.

In summary, and while describing various systems, methods and protocols for attempting to optimize the efficiency of patient care, the prior art as a generalization acknowledges the inviolability of the present healthcare delivery model with its existing compensation and incentive structures. These notably reward physicians and other medical providers based on the quantum of care provided (e.g. tests conducted, surgical procedures performed, etc.) and as opposed to tying such compensation/incentives to documentable patient outcomes.

SUMMARY OF THE PRESENT INVENTION

The present invention provides a system, method and non-transitory and software/algorithmic based computer writeable medium for revolutionizing the delivery of healthcare, this primarily through the formulation and implementation of results driven compensation/incentives to the provider (e.g. doctor, surgeon or other medical care professional), and as opposed to traditional compensation methods which reward such providers on the basis of quantum of care provided (tests ordered, surgical procedures conducted). The underpinnings of the present invention include a central processor into which is loaded a best practices and corresponding (financial) incentive database, the contents of which can be promulgated or modified by a given payor or ACO (accountable care organization).

In one variant, the non-transitory computer writeable medium incorporates a predictive algorithm which includes a series of protocols including a first protocol or subroutine for establishing a risk profile through stratifying a designated ACO population. A second protocol or subroutine of the predictive algorithm further operates by training the ACO doctors or other care providers in one or more of a series of medical related diagnosis and treatment programs (or disciplines) these further potentially including but not limited to any one or more of joint, spine, cardiac, acute care, post-acute care, wound, vascular, cancer, diabetes, kidney, urology, pulmonary and vision care.

A third successive protocol/subroutine includes establishing one or more management pathways which are customizable by the ACO leadership. This is accomplished through the establishing of a questioning protocol for modifying/customizing the base algorithm for any one or more of a variety of treatment sub-species and in order to establish subroutines at this stage for any one or more of emergency care, immediate care, systemic complications, disability risk, psycho-social issues, preventive care and/or maintenance care.

A fourth protocol/subroutine provides care provider (e.g. doctor) feedback on the desired best practices for the given diagnosis and treatment sub-species resulting from the question and answer protocol achieved in the third subroutine. A fifth protocol results in the creation (again by the ACO or other provider) of a scorecard for each individual care provider (doctor, therapist, etc.), such based primarily upon patient outcome assessment and accounting for patient complexities. In this fashion, shared savings resulting from the implementation of the program results are distributed based on the simplicity, transparency and accountability provided by the present system and computer writeable medium.

One non-limiting physical aspect of the present system includes the provision of a patient kiosk (such loosely defined to include any patient accessible input ranging from a physical station to a mobile application loaded into a smartphone or tablet computer) and which permits a patient to input necessary biographical and medically relevant information along with other information, the carrot for providing which can include additional benefits and enticements. A decision support system interfaces with the processor and, in combination with additional information inputs required by the service provider (e.g. physician, group of physicians or other designated care providing entity including a hospital, clinic, etc.) formulates a provider scorecard for each such individual or entity which grades and rewards such providers based upon their adherence to the best practice standards set by the ACO or other payor.

In this fashion, the present invention seeks to recalibrate the incentive structure of the care provider (such as further defined in non-limiting fashion to include healthcare facilities such as hospitals and nursing homes and in addition to individual physicians or various general/specialized practice groups) by, in large part, tying compensation to adherence to the best practices standards and protocols set by the local ACO or other responsible payor. In this fashion, and by delegating responsibility for the formulation, administration and enforcement of the present system to the designated (e.g. local) payor/ACO, the various care providers are generally are understood to accede to these established standards and protocols, thereby providing the necessary participation for guaranteeing the success of the model.

The advantage of this system is that it rewards/compensates such care providers based upon the desired outcome of treatment which is in accordance with the established practices and protocols (quality of treatment), and without regards to the quantum of treatment provided (number of tests ordered, surgical procedures performed, etc.). At the same time, such care providers are rewarded for any level or quantity of treatment (again including tests, procedures, etc.) which are consistent with the desired standards established by the ACO and, equally importantly, are provided according to the protocols established. One application of this is to incentivize the care provider to follow the desired practices and protocols first and before resorting immediately to invasive medical procedures which do not contribute to overall patient quality of care so much as to the financial benefit of the care provider. Beyond physician and physician groups, the present inventions are further understood to apply to all clinical providers, not limited to therapists, psychologists, nurses, and other healthcare facilities such as nursing homes and hospitals.

A related module provides for optimizing the diagnosis, treatment and resolution of worker injury events, such as associated with a workman compensation claim, and which improves upon the existing paper based module by synthesizing, in a digital environment, symptom, treatment and progress variables in a multi-party available format. In particular, the injury event module greatly increases care provider (physician) efficiency by integrating and compiling electronically, in easily readable and time elapsed formats, symptom and treatment variables. The module additionally provides a reasonable and agreeable model, such as between the employer/payer and worker, for establishing minimal goals for facilitating return to work.

A further related rehabilitation module, such as not limited to a worker injury event but also including any injury event associated with a typical accountable care organization (insurer/other payor/etc.) in a general health application is provided for establishing and tracking a patient's functional independent (FEM) measurement score. As with the workman compensation module, the rehabilitation module integrates the establishment of current conditions, achievable goals, and time based tracking of the patient treatment (including time elapsed changes in response to flat line response indicating a non-effective treatment plan) in order to define a patient goal outcome and to optimize real time treatment and progress tracking to that goal.

BRIEF DESCRIPTION OF THE DRAWINGS

Reference will now be made to the attached drawings, when read in combination with the following detailed description, wherein like reference numerals refer to like parts throughout the several views, and in which:

FIG. 3 is a graph depicting Quality versus Spending and which identifies a maximum point of return on investment;

FIG. 4 is a spreadsheet depiction of a care value index AHA (ACO)/SC spine program;

FIG. 7 is a MODUS (loosely defined as an operational model for sharing risks and rewards between healthcare payers, providers and patients) client spine spreadsheet illustration similar to FIG. 4 and which provides an exemplary breakdown of primary care physicians (PCP's) and associated specialists (spine surgeon, chiropractor, psychologist, physical therapist, etc.) for a given client, such further illustrating such as best practices scores, overall percentage ratings, patient satisfaction, payer cost and shared savings, the payments provided by the ACO for the patient/client being bundled in a designated amount and thereafter distributed to the various providers as per the scorecard ratings achieved;

FIG. 8 is an illustration of a patient enrollment screen display, such as associated with the patient kiosk module, and which provides entry fields for enabling the patient to provide necessary information for the system, the incentive for entering can include specified rewards (e.g. gift certificates, etc.);

FIG. 9 is a screen illustration of an editable preferred specialty providers page associated with the scorecard aspects of the system and computer writeable medium and which provides detail as to particular treatment options and protocols administered by that provider (such as which are condition specific in particular regards to spinal pain treatment) and along with corresponding best practice ratings;

FIG. 10 is a first colored (purple) flag screen illustration generated according to the best practices protocol and associated decision support system, resulting from an initial patient analysis and diagnosis, and with a recommendation for treatment of a diagnosed impaired function of the patient by a primary care physician with specified (desired) options;

FIG. 11 is a succeeding illustration to FIG. 10 and depicting a management generated report based on the initial treatment decisions of the primary care physician;

FIG. 14 is a third colored (red) flag screen illustration generated according to the best practices protocol and associated decision support system, resulting from a succeeding and updated patient diagnosis to that assessed in FIG. 10, and with a recommendation for a referral by the primary care physician such as to a specialist;

FIG. 15 is a succeeding illustration to FIG. 12 and depicting a management generated report based on the decisions of the specialist;

FIG. 19A is a first screen illustration of a patient informational entry page associated with the variant of FIG. 18;

FIGS. 19B-1 and 19B-2 collectively depict a second screen illustration of associated with the patient informational entry page and providing a series of entry fields relative to such issues as stress, pain, etc.;

FIG. 19C is a third screen illustration associated with the patient informational entry page and providing a series of entry fields relative to establishing a patient functional level;

FIG. 20A succeeds FIG. 19 and provides a first screen illustration of a physician (care provider) informational entry page;

FIG. 20B succeeds FIG. 20A and provides a second screen illustration of a physician informational entry page and which includes additional entry fields with real time best practice compliance indication;

FIG. 23 is a supervisor/employer information entry screen associated with a workman compensation module according to a further embodiment of the present inventions;

FIG. 24 is a succeeding supervisor/employer information entry screen to that shown in FIG. 23;

FIG. 25 is a doctor assignment screen which the module produces in response to the inputs of the information entry screens of FIGS. 23-24;

FIG. 26 is a first confirmation of details screen outlining biographical information to be entered by the worker/injured party;

FIG. 27 is a second confirmation of details screen providing additional entry field for the worker/injured party to fill out including confirming details of the injury as reported by the supervisor, as well as confirming and updating scope of duties;

FIGS. 29-30 is another view of the symptoms input screen of FIG. 28 indicating symptom entry fields inputted by the worker relating to type and intensity of pain;

FIGS. 31-39 illustrate a progression of symptoms catalog screens for weeks 1-9 from date of injury event and providing, for the viewing benefit of all of the treating physician, the injured worker, and the ACO/payor/employer condensed/synthesized and time elapsed progress metrics displaying and tracking the injured worker's improvement in condition and function;

FIG. 40 a first worker ability input screen forming a portion of a related sub-component of the workman compensation module and depicting a number of entry fields which specify current ability metrics of the worker/patient;

FIG. 41 is a related worker ability screen which combines the current ability inputs of FIG. 40 with established goals;

FIGS. 45A and 45B collectively depict a first rehabilitation setting input screen according to a further module and providing a series of patient entry fields such as for each of prior function, current function and goal function;

DETAILED DESCRIPTION OF THE PREFERRED EMBODIMENTS

Figure 5:
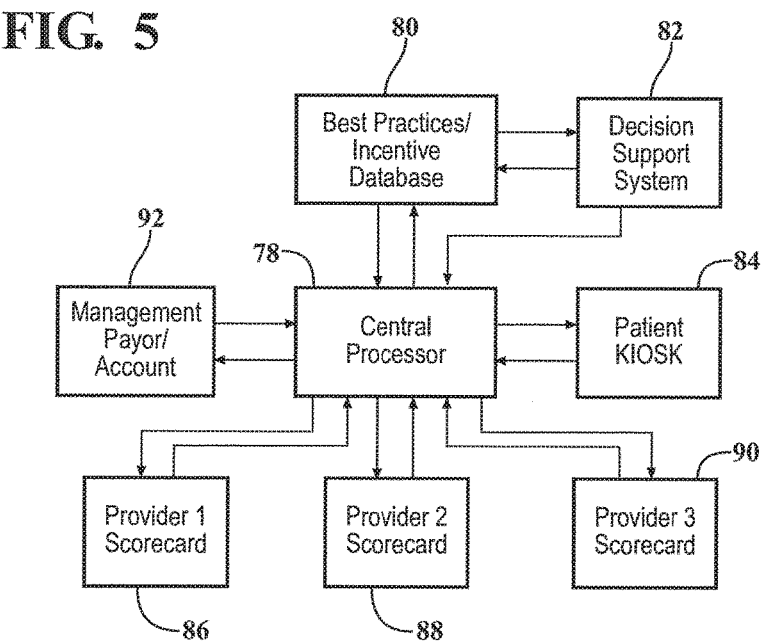
FIG. 5 is a flow diagram of the present system and which illustrates the interactive nature of the central processor which interfaces with each of the best brackets/incentive database, associated decision support system, patient kiosk, provider scorecards and payor/ACO interface.

With reference initially to FIGS. 1-4, a first non-limiting application of the present system, method and software/algorithmic based computer medium is depicted in the form of a specific spinal pain related application of the present invention, it being understood that, with succeeding reference to FIG. 5 et seq., the present inventions are applicable to any situation dealing with the providing of services, such not limited to any subset arear of specialty involving the delivery of healthcare and can be equally applicable to non-medical related models in which the desire is to retrain/ incentivize the various service providers to focus on adherence to a best practices model and actual/verifiable patient/ client outcomes, and as opposed to basing such incentives and compensation on the quantity of service provided.

Referring again to the particular model of FIGS. 1-4, from a statistical standpoint, approximately 80% of the population will experience some level of spinal pain at some point in their lifetime. At any given time, 31% of the population suffers from an existing spinal related issue. Spinal fusion procedures currently account for the number 1 inpatient cost with spinal pain currently also the number 1 outpatient cost and second highest reason for work absenteeism. Other factors relating to the costs of spinal pain and associated conditions include incidences of emergency room visits (#3 for females and #5 for males for age groups 15-65), the cost to the U.S. economy (presently $100 billion per year) and the percentage (41% to 87%) of worker compensation costs.

Existing spinal treatment protocols, such as in particular first or second level fusion of spinal vertebrae, further often result in significant costs (surgical and hospital including for operating room, anesthesiologist, follow up care, etc.) as well as patient downtime during recovery. An outcome study in the state of Washington found 100% disability rate for patient undergone spinal fusion surgery. Other medical conditions associated with persistent back pain, notably anxiety and depression, are a major factor in worsening the patient outcome and the current care model fails to address the anxiety and depression because the care for these conditions is not as lucrative as doing procedures on these patients. In lieu of this, editable management options are provided for various providers group preferences, along with color and numbers visual real-time feedback to users about their compliance score (with subsequent reference to FIG. 17).

As a result of the fee for service payment system, providers are rewarded for doing more (procedures or medication prescriptions) regardless of the patient medical or functional outcomes. Currently, the medical system has very limited mechanisms to hold providers accountable for their work and providers are often in fact rewarded for doing and providing more care (and not necessarily better care) for their patients.

Existing treatment schemes (including fee for service models) reward care providers in volume as opposed to effectiveness of the care, resulting in significantly diminished returns on investment (as referenced in the apex point depicted in the graph of FIG. 3), with even decreased returns for significant additional investment as reflected in patient morbidity and mortality. Providers compliance with best practice guidelines for spine pain has always been low and in the study by Mafi et al 2013, the compliance with best practices it being noted as worsening over the past decade.

Figure 1:
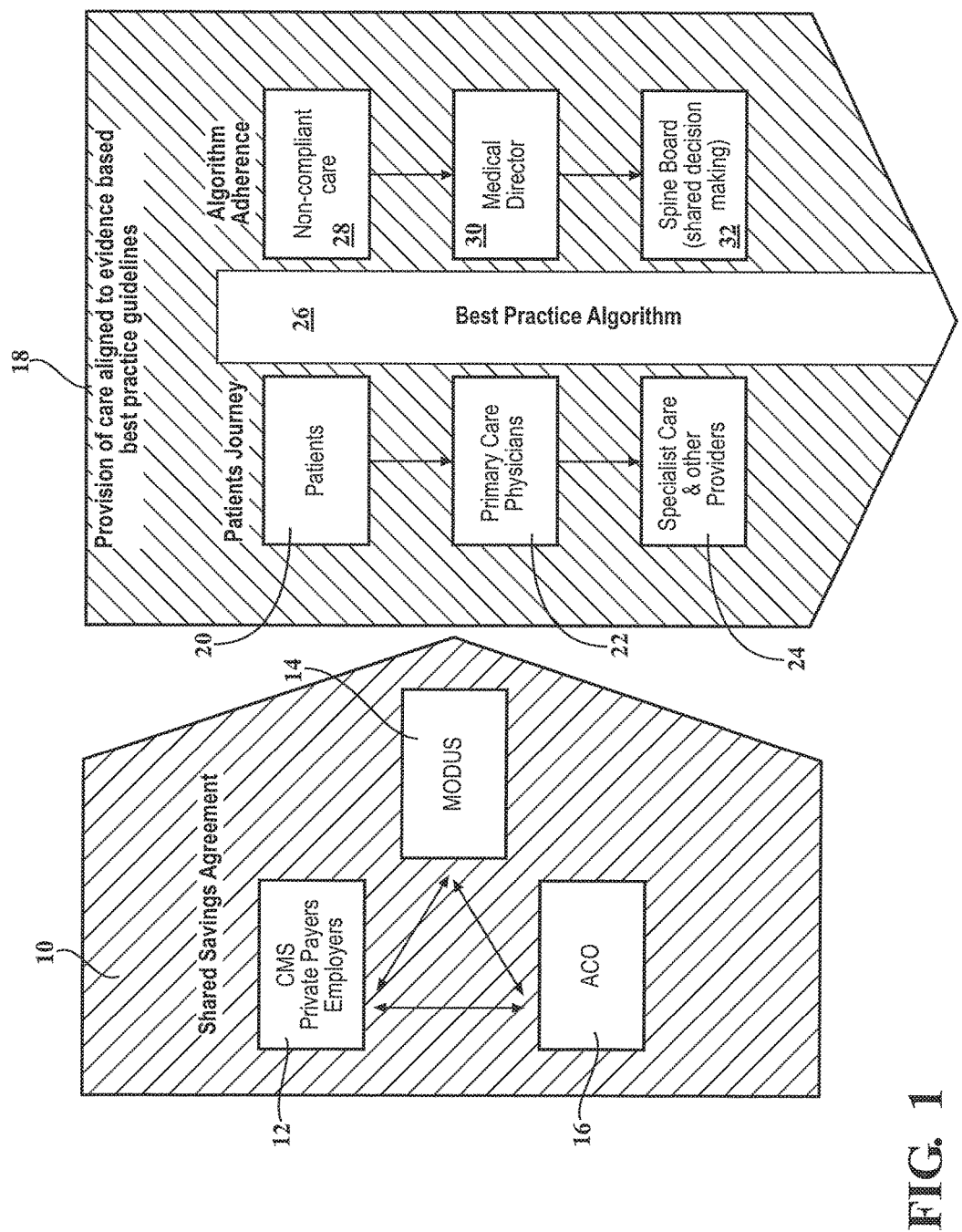
FIG. 1 is a schematic of an operational model according to one non-limiting aspect of the present invention and which combines aspects of shared savings agreements as applied to provisional of level of care aligned to evidence based best practice guidelines.

In response to the above conditions, the present system enables health care payers and to recognize value and pay for the provider's results instead of just paying for efforts. Beyond that, the present invention seeks to combine system, process and algorithmic based medium for establishing a best practices protocol for treating a variety of medical conditions (including spinal pain management). Referring first to FIG. 1, a schematic of an operational model is provided according to one non-limiting aspect of the present invention and which combines aspects of shared savings agreements as applied to provisional of level of care aligned to evidence based best practice guidelines. The present system will measure data on clinical providers in regards to each of best practice compliance, patient's functional outcomes and patient satisfaction. The unique data will further enable the payers to reward providers for their patients outcomes and not just for efforts (e.g. such as again measured in volume of service or care provided). Such a system effectively makes the providers accountable to their patients and payers.

FIG. 1 illustrates, at 10, an overall representation of a shared services agreement and which encompasses the interactive aspects of a CMS (Centers for Medicare/Medicaid Services) Private Payers Employers 12, scientific consultants 14 and ACO (Accountable Care Organizations). By definition, ACO's are groups of doctors, hospitals and other healthcare providers that share responsibility for providing care for their patients. By coordinating their efforts, these groups provide higher-quality care in a more cost-efficient manner. They then share in the profits from the savings that result. As further defined, an Accountable Care Organization can be developed through the Centers for Medicaid and Medicare (CMS) or privately outside of the CMS structure.

The shared services agreement (module) 10 interfaces with a further module 18 encompassing a provisional of level of care aligned to evidence based best practice guidelines. A patient journey component includes designations for patients 20, primary care physicians 22 and specialist care and other providers 24. A best practices algorithm (see as generally represented at 26 in FIG. 1 and further delineated in FIG. 2) is provided and interfaces the patient journey components with algorithm adherence aspects including each of non-compliant care 28, medical director 30 and spine board 32.

Figure 2:
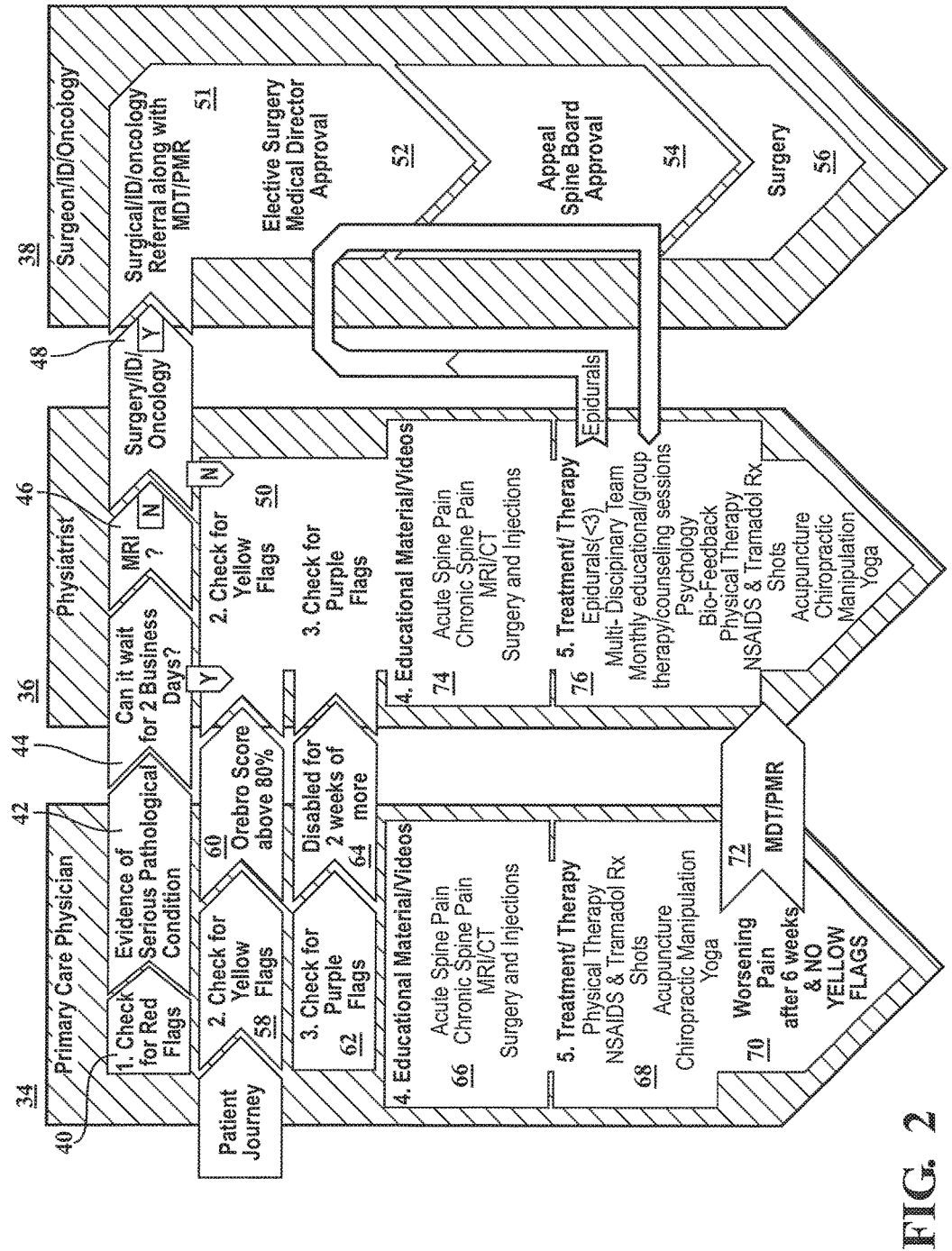
FIG. 2 is a related representation of a best practices algorithm dealing with interactive events involving each of a primary care physician, physiatrist and surgeon.

Proceeding to FIG. 2, a related representation of the best practices algorithm 26 is provided and detail dealing with interactive events involving each of a primary care physician 34, physiatrist 36 and surgeon 38 components. The patient journey starts with either the primary care physician, a physiatrist or a spine surgeon and they all initiate the care by checking, at step 1 (40), for any immediate red flags which are evidenced of serious pathological conditions (42) then checking for yellow flags associated with catastrophizing responses by the patient who will need multi-disciplinary care team (that includes psychological care) and everyone checks for purple flags (documenting the patient functional level) 36.

A magnetic resonance imaging (MRI) 44 step can succeed the evaluation step 42, following which a surgical recommendation 46 of the physiatrist. By definition, a physiatrist/ rehabilitation physicians is a medical doctor who has completed training in the medical specialty of physical medicine and rehabilitation (PM&R). Specifically, rehabilitation physicians provide each of diagnosing and treatment of pain, restoration of maximum function lost through injury, illness or disabling conditions, treatment of the whole person, not just the problem area, leading a team of medical professionals, providing non-surgical treatments, and managing medical problems and treatment/prevention plans.

By further definition, the job of a rehabilitation physician is to treat any disability resulting from disease or injury, from sore shoulders to spinal cord injuries. The focus is on the development of a comprehensive program for putting the pieces of a person's life back together after injury or disease—without surgery unnecessary medical procedures and by incorporating the shared decision protocols integrated into the present inventions.

Rehabilitation physicians are doctors of function, they take the time needed to accurately pinpoint the source of an ailment. They then design a treatment plan that can be carried out by the patients themselves or with the help of the rehabilitation physician's medical team. This medical team might include other physicians and health professionals. These include such as psychologists, physical therapists, occupational therapists, health coaches, athletic trainers, social workers, neurologists, orthopedic surgeons, and physical therapists. By providing an appropriate treatment plan, rehabilitation physicians help patients stay as active as possible at any age. Their broad medical expertise allows them to treat disabling conditions throughout a person's lifetime.

Surgical recommendation 46 can result in yes 48 or no 50 steps. If yes, surgeon 38 module is activated and results in a surgical referral 51, progressing to an elective surgery medical director approval step 52, appeal of a spine board approval 54 and, finally, surgery 56.

Alternate to red flag step 40, a check for yellow flag step 58 proceeds to a determination if an Örebro score exceeds 80% (at step 60). The same occurs at previously identified step 50 in the instance of the physiatrist (module 36) determining that surgery is not an option.

The Örebro Musculoskeletal Pain Questionnaire (ÖMPQ), formerly known as the Acute Low Back Pain Screening Questionnaire (ALBPSQ), was developed to help identify patients at risk for developing persistent back pain problems and related disability.

The questionnaire is intended to be used with individuals who are experiencing regional pain problems that are affecting their performance at work, taking repeated short spells of sickness absence or are currently off work. In one version of the questionnaire, there are twenty one scored questions concerning attitudes and beliefs, behaviour in response to pain, affect, perception of work and activities of daily living.

The questionnaire can usually be completed in 5 min before the patient meets the health professional. A cut-off score of 105 and below has been found to predict, with 95% accuracy, those who will recover and, with 81% accuracy, those who will have no further sick leave, in the next 6 months.

Prediction of long-term sick leave (>30 days within the next 6 months) was found to be 67% accurate. A cut-off score of 130 and above correctly predicted 86% of those who failed to return to work. The effect of this score is to assist the clinician to apply interventions (including the use of activity programs based on cognitive behavioural strategies) to reduce the risk of long-term pain-related disability. Evidence indicates that these factors can be changed if they are addressed. It has also been found that the total score is a relatively good predictor of future absenteeism due to sickness absence as well as function, but not of pain. The results suggest that the instrument could be of value in isolating patients in need of early interventions and may promote the use of appropriate interventions for patients with psychological risk factors.

The primary care physician module 34 includes a further step 62 for checking for the existence of a purple flag, this further indicating at step 64 that the patient is likely disabled for two weeks or more (in turn leading to a similar purple flag analysis within physiatrist module 36). Additional steps associated with the primary care physician module 34 include each of step 66 for providing (to the patient) education material/videos relating to acute/chronic spinal pain, MRI or CT (computed tomography) procedures, surgery and associated injections, as well as step 68 for providing treatment/therapy options (physical therapy, non-steroidal anti-inflammatory drugs or NSAIDS, Tramadol Rx shots, Acupuncture, chiropractic manipulation and yoga). Following these steps, and if worsening pain persists after six weeks with no yellow flags (step 70), an MRI procedure is performed at step 72 when advancing to the physiatrist module 36.

Physiatrist module also includes a similar step 74 (as compared to at 66 in physician module 34). Step 76 recites additional treatment/therapy protocols including up to three epidural procedures (see further feedback loop interfacing with surgical module 38 and steps 52-54. Additional aspects of step 76 include each of use of multi-disciplinary teams, psychology, bio-feedback and other aspects previously recited in step 68.

Additional aspects of the invention include the provision of a suitable software component for effectuating some or all of the objects of the invention, such including interfacing each of the modules 34, 36 and 38 of the best practice algorithm, this in order to most effectively and efficiently providing for communication between the various care providers and in order to enforce the objectives of the best practices protocol in order to avoid excessive treatments/procedures and, most notably, unnecessary surgeries in order to effectively treat many types of spinal ailments. The software module is understood to interface with any suitable processor driven tablet, hand-held smart phone, laptop, PC or the like in order to quickly and efficiently interface each of the medical providers or other specialists described herein.

The care value index of FIG. 4, see at 75, provides one non-limiting example of a tabular arrangement for providing a breakdown of individual metrics for any plurality of care providers not limited to primary care physicians (PCP's) and specialty care physicians such as spinal surgeons, chiropractors, psychologists and the like. Referencing the table of FIG. 4, the purpose for this is to provide one non-limiting example of a series of metrics which can be used in establishing a supporting financial model for assisting in incorporating an existing/most recently updated best practices protocol and in order to determine both the maximum efficiency of investment referenced in FIG. 3 (graph 75 depicting Quality versus Spending and which identifies a maximum point of return on investment), along with providing a readily accessible model for properly acknowledging and rewarding a provider for both adhering to the best practices protocol. In concert with the above description, the objects of the present invention include the ability to partner with providers networks in order to achieve better patient clinical and functional outcomes at lower cost. By rewarding providers for integration, care coordination, adopting evidence based best practice and peer review, the present system results in minimizing unnecessary care which will result in benefits for patients, practitioners, employers, employees and third parties.

Proceeding to FIG. 5, a flow diagram is provided of the present system and which illustrates the interactive nature of a central processor 78, which interfaces with each of a best brackets/incentive database 80, an associated decision support system module 82, a patient kiosk 84, and a plurality of subset devices 86, 88, 90, et seq., associated with each of a designated group of individuals or entities associate with a service provider organization (such ranging from an individual physician to a practice group including classes of primary care physicians, specialists/surgeons, physical care specialists and the like). Also depicted at 92 is payor/ACO module which likewise interfaces with the central processor 78 and can include a separate computer, laptop or any other processor driven device. The payor/ACO module is also generally designated as a management model and to account for the fact that the payor/ACO may elect to designate an outside supervisory entity.

Without limitation, the processor 78 can include any type of computing device not limited to a hard drive containing computer, laptop, etc., as well as a cloud based processor or database. The subset devices 86, 88, 90 et seq. can further be provided as any of a laptop, tablet computer, smart phone or the like and which are in wired or wireless, including 3G, 4G LTE, Bluetooth, or NFC (near field communication) with the central processor and its output functions.

As will also be now described with reference to FIG. 6 et seq., the implementation and performance of the present system and method relies upon the creation of an effective algorithmic based software program which is loaded into or otherwise interfaced with the central processor 78 and its various communicating components 80-92. Such a software program can include various modules or components associated with each of the hardware devices, in one instance a first software module associated with the central processor module 78, as well as its interfacing lookup table incorporating the best practices model and the attendant decision support system, and which also includes additional subset modules in interfacing/two-way communication with the central processor and module, such subset modules also envisioning being in the form of a mobile application which can be accessed by any of a laptop, tablet or smart phone.

Figure 6:
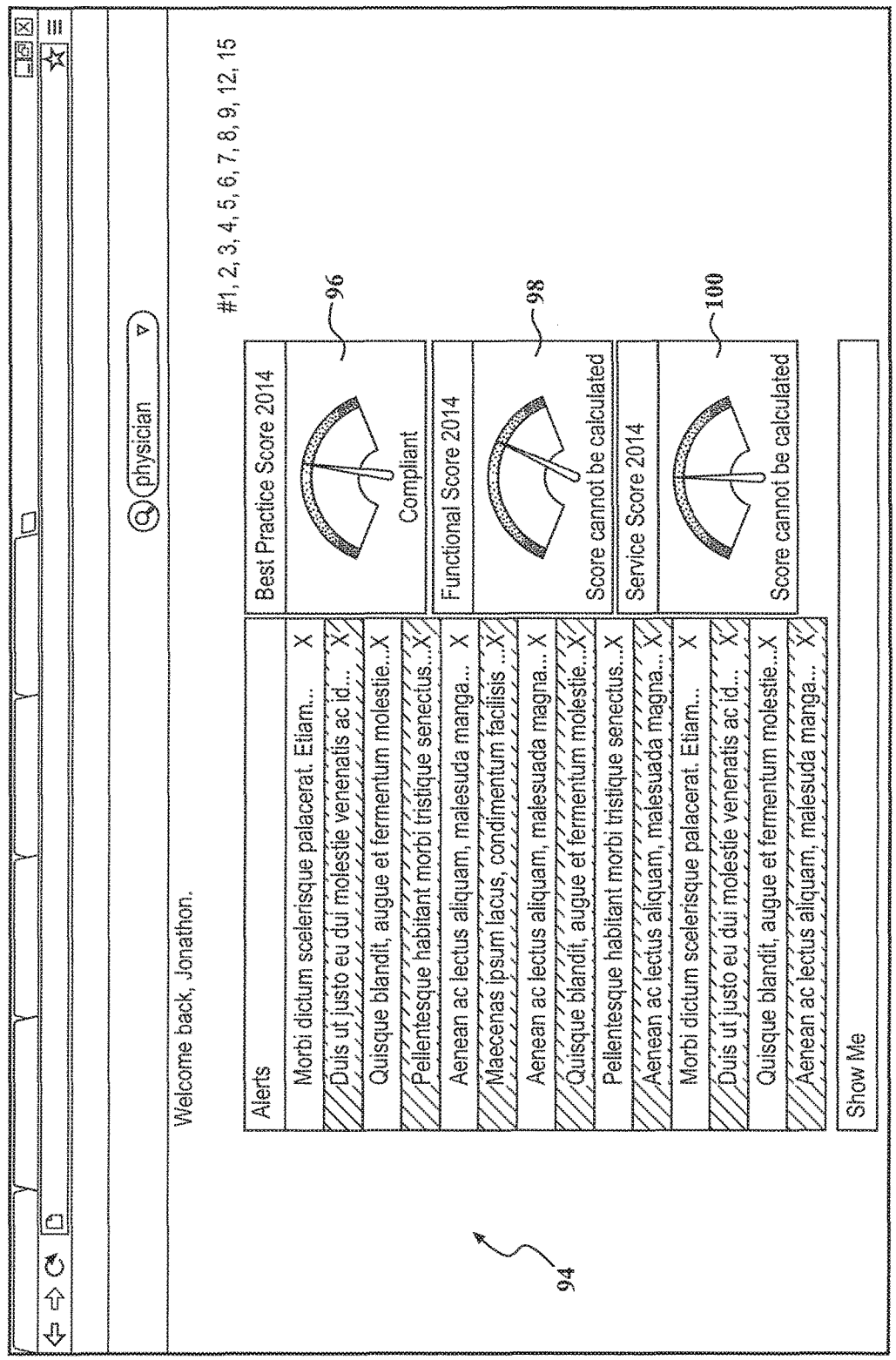
FIG. 6 is a first screen shot illustration of a best practices driven scorecard which is derived from the present system and non-transitory computer writeable medium for providing a rating of the physician or other care provider on the basis of adherence to the practice objectives and protocols established by the ACO or other designated authority.

Referring to FIG. 6 is a first screen shot illustration is provided at 94 of a best practices driven scorecard which is derived from the present system and non-transitory computer writeable medium for providing a rating of the physician or other care provider on the basis of adherence to the practice objectives and protocols established by the ACO or other designated authority. Without limitation, this can include providing an ongoing rating (such as on a yearly basis) on a percentage basis of an achieved best practices score (see for example at 57% at 96), as well functional score (further example shown at 68% at 98) and service score 100.

FIG. 7 is a spreadsheet illustration, at 102 and similar to as shown at 75 in FIG. 4, and which provides an exemplary breakdown of primary care physicians (PCP's on line item 6) and associated specialists (spine surgeon on line 36, chiropractor on line 38, psychologist on line 40, physical therapist on line 42, etc.) for a given client, in this instance associated with a spinal treatment program. This illustration further itemizes such as best practices scores, overall percentage ratings, patient satisfaction, payer cost and shared savings, the payments provided by the ACO for the patient/client being bundled in a designated amount and thereafter distributed to the various providers as per the scorecard ratings achieved. The spreadsheet illustrations of FIGS. 4 and 7 can generally represent one output and illustrative function associated with the management (ACO/payer) module 92 and which assists in tracking the breakdown and distribution of lump sum budgets which are allocated to a given practice group/service provider.

Figure 8:
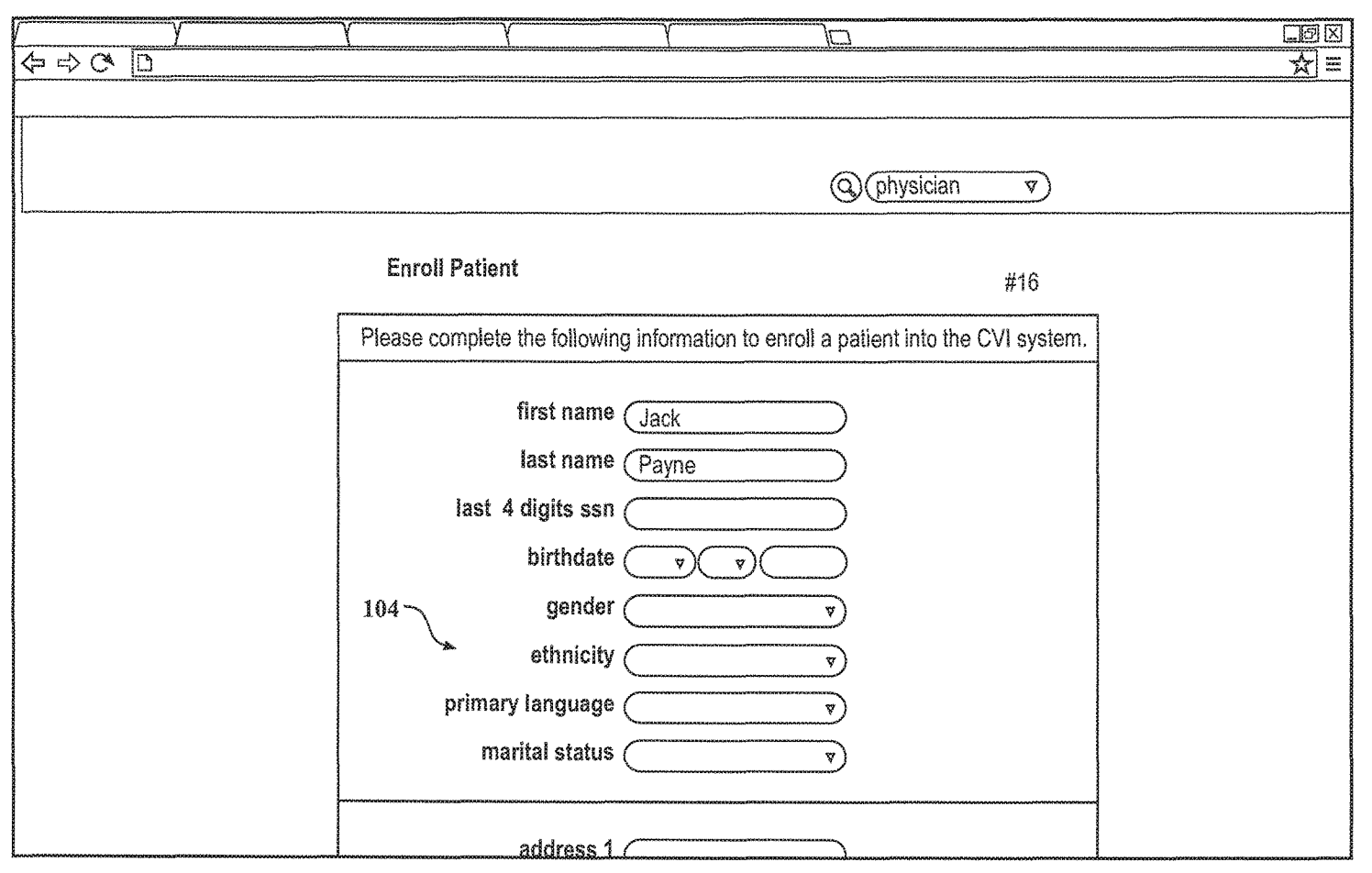

FIG. 8 is an illustration, at 104, of a patient enrollment screen display, such as associated with the patient kiosk module, and which provides a series of biographical or other entry fields for enabling the patient to provide necessary information for the system. The present inventions contemplate the participation of the patient/client, not only in the inputting of information which is more efficiently obtained directly as opposed to being recorded by other personnel, but also in the ability to provide the patient/client with the ability to comment on the performance of the care provider to further assist in assessing and scoring the performance metrics of that provider. The present inventions contemplate providing incentives to the patient for his/her participation and such can include specified rewards (e.g. gift certificates, discounts, etc.) for providing the requested information.

Figure 9:
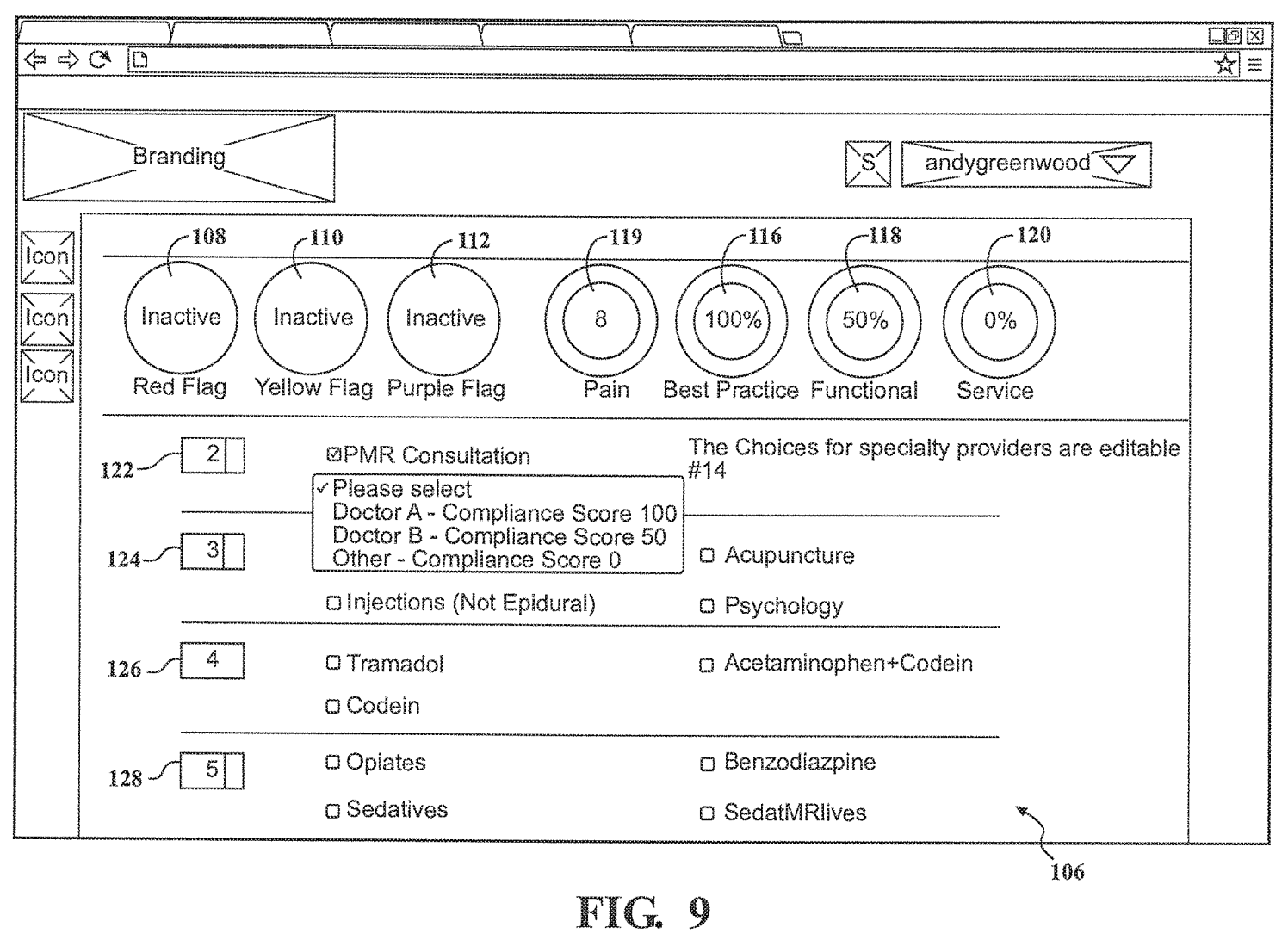

FIG. 9 is a screen illustration of an editable preferred specialty providers page, see generally at 106, associated with the scorecard aspects of the system and computer writeable medium and which provides detail as to particular treatment options and protocols administered by that provider (such as which are condition specific in particular regards to spinal pain treatment) and along with corresponding best practice ratings). As will be described with additional detail in reference to succeeding FIGS. 10-17, the specialty provider's page can designate any one of a red 108, yellow 110 or purple 112 flag, as well as providing a pain level indicator 114, a best practice compliance score field 116, a functional field 118 and a service field 120. Additional designations 122-128 in FIG. 9 can reference color coding for each of a succession of treatment option subsets, respectively at 2-5, and associated with various stages of spinal pain treatment.

Figure 11:
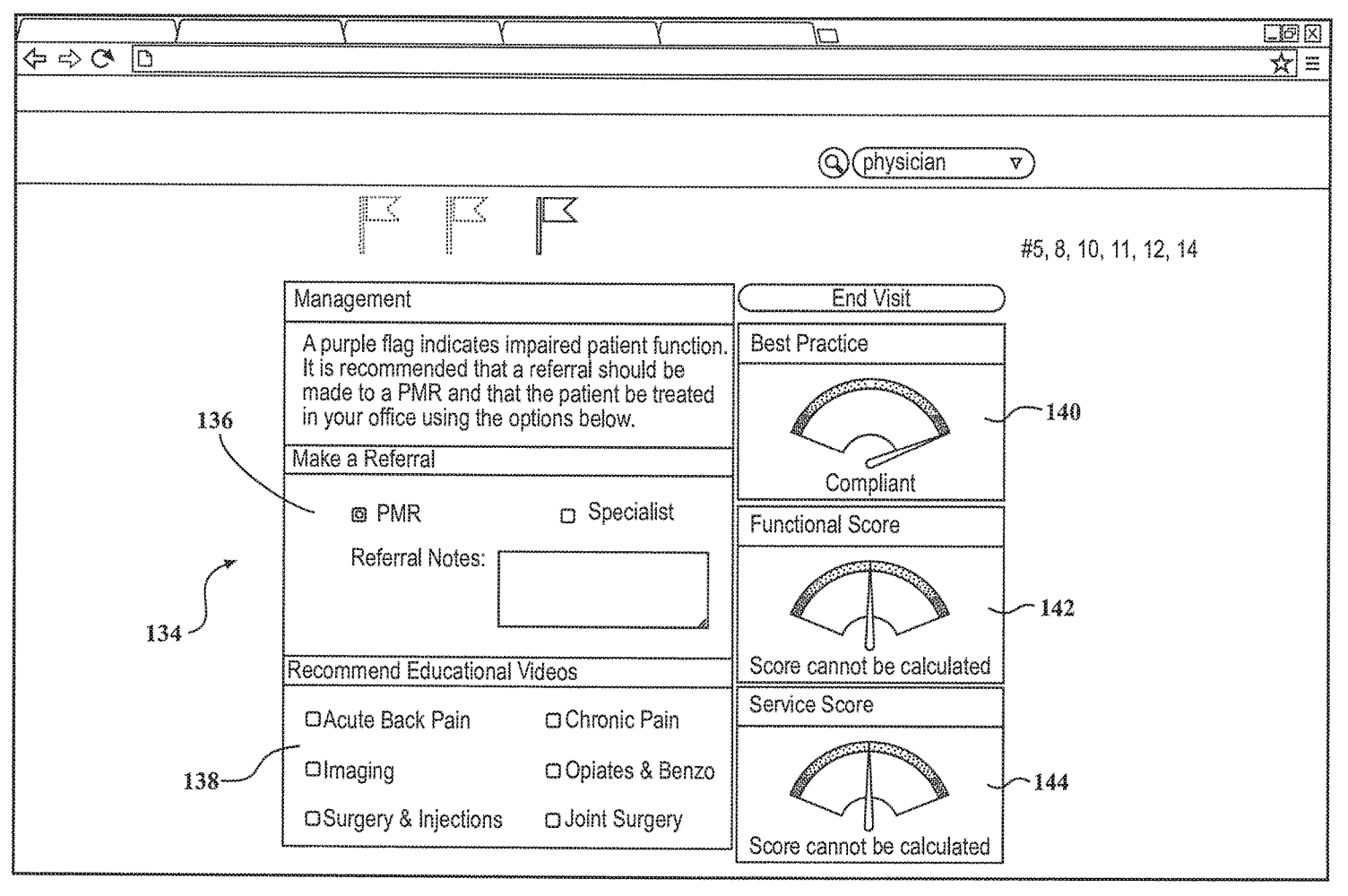

FIG. 10 is a first colored (purple) flag screen illustration 139, such as which can be associated with the management module 92, and which is generated according to the best practices protocol and associated decision support system, and resulting from an initial patient analysis and diagnosis, and with a recommendation for treatment of a diagnosed impaired function of the patient by a primary care physician with specified (desired) options. Also depicted at 132 is a field designating that care provider's functional score in terms of best practice compliance. FIG. 11 is a succeeding illustration to FIG. 10 and depicting a management generated report 134 based on the initial treatment decisions of the primary care physician and including entry fields for referrals 136, recommended educational videos 138, as well as rating identifiers (such as provided on a percentage basis) and again including best practice 140, functional score 142 and service score 144.

Figure 12:
FIG. 12 a second colored (yellow) flag screen illustration generated according to the best practices protocol and associated decision support system, resulting from an alternate initial or further patient analysis and diagnosis (to that provided in FIG. 10) and indicating an increase in the patient's anxiety level, and with a recommendation for treatment of the patient by a primary care physician with additional specified (desired) options.
Figure 13:
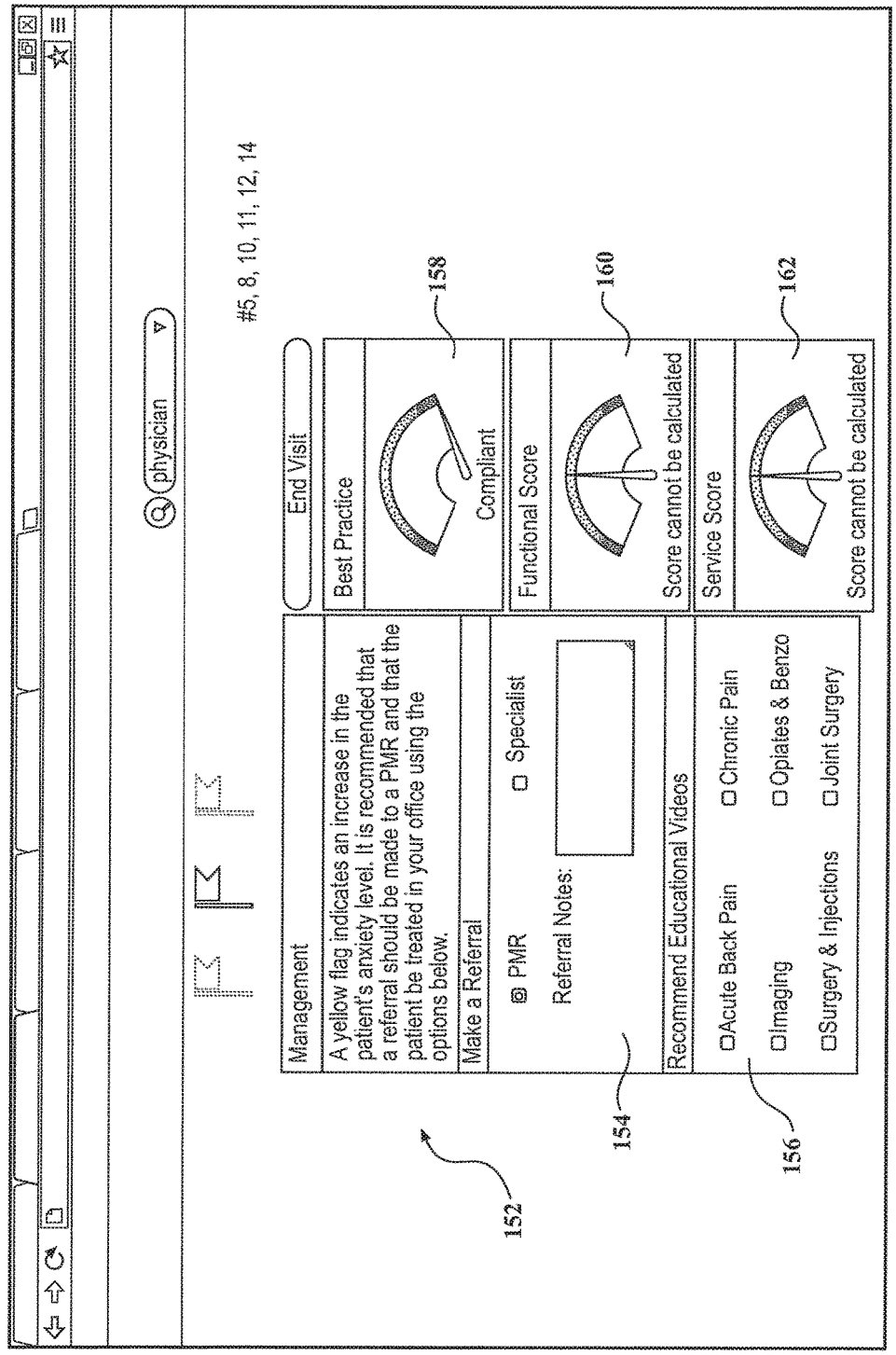
FIG. 13 is a succeeding illustration to FIG. 12 and depicting a management generated report based on the decisions of the primary care physician.

FIG. 12 is a second colored (yellow) flag screen illustration 146 generated according to the best practices protocol and associated decision support system, this resulting from an alternate initial or further patient analysis and diagnosis (to that provided in FIG. 10) and indicating an increase in the patient's anxiety level (at field 148), and with a recommendation for treatment of the patient by a primary care physician (150) with additional specified (desired) options. FIG. 13 is a succeeding illustration to FIG. 12 and depicting a management generated report 152 based on the decisions of the primary care physician, along with and including entry fields for referrals 154, recommended educational videos 156, as well as rating identifiers (such as provided on a percentage basis) and again including best practice 158, functional score 160 and service score 162. In application, this designation can further provide a final service outcome (the scorecard) that MODUS (as defined herein) provides.

Figure 15:
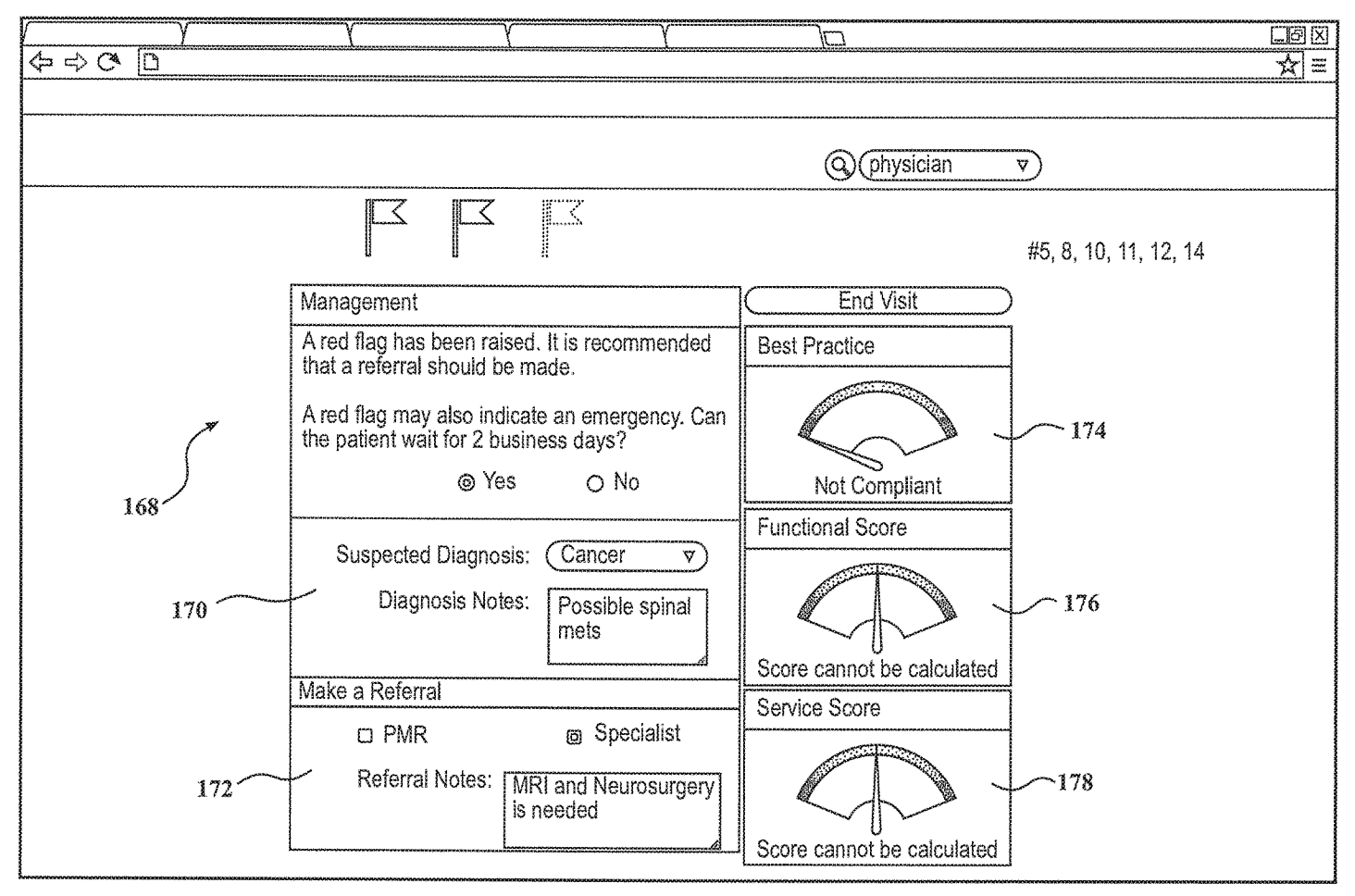

FIG. 14 is a third colored (red) flag screen illustration 164 generated according to the best practices protocol and associated decision support system, resulting from a succeeding and updated patient diagnosis to that assessed in FIG. 10, and with a recommendation, at 166, for a referral by the primary care physician such as to a specialist. FIG. 15 is a succeeding illustration to FIG. 12 and depicting a management generated report 168 based on the decisions of the specialist, such including a diagnosis field 170, referral field 172 and repeat of compliance ratings for best practice (not compliant as designated at 174), functional score 176 and service score 178.

Figure 16:
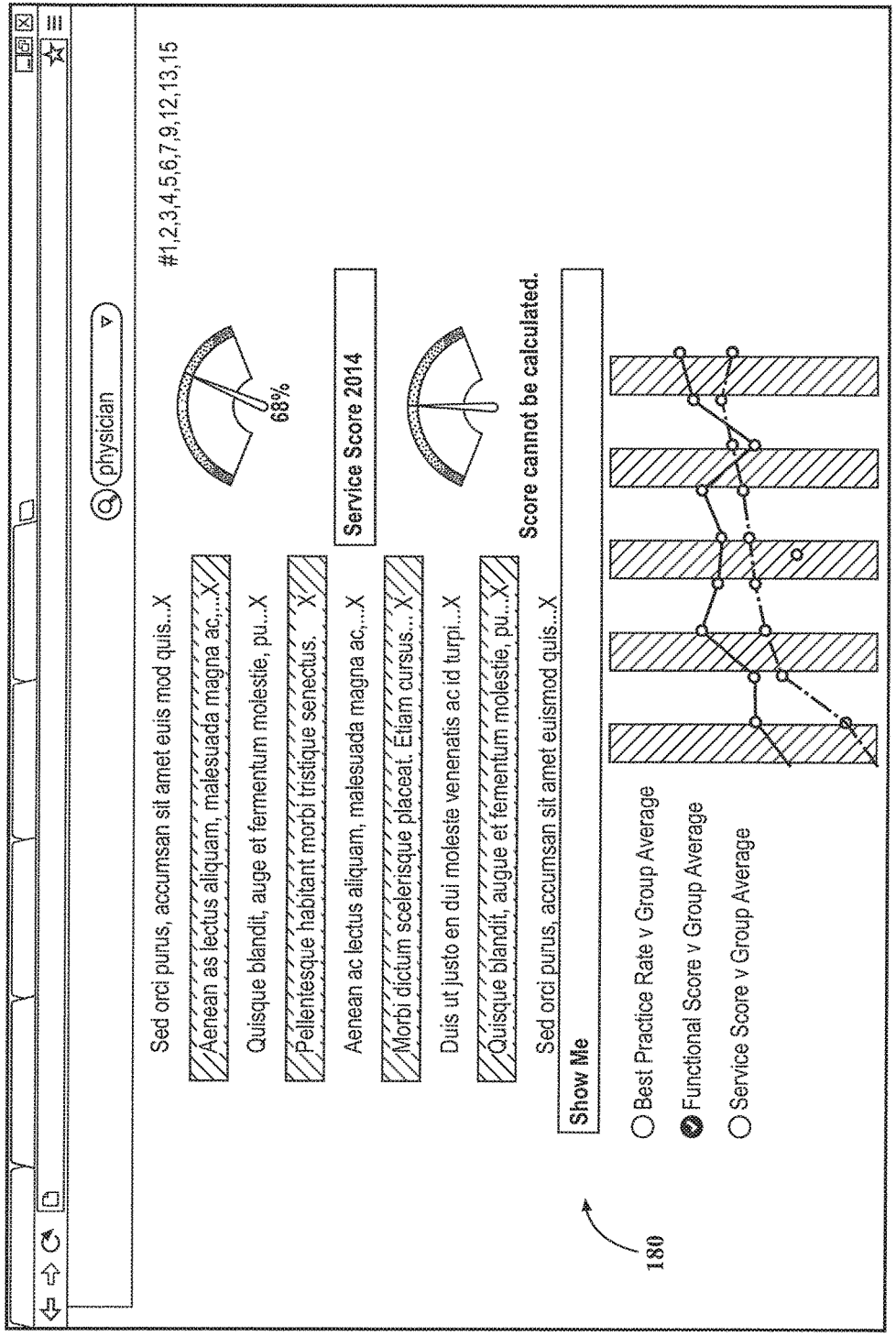
FIG. 16 is a screen display of a comparison graph of a functional score vs. group average for a given physician.
Figure 17:
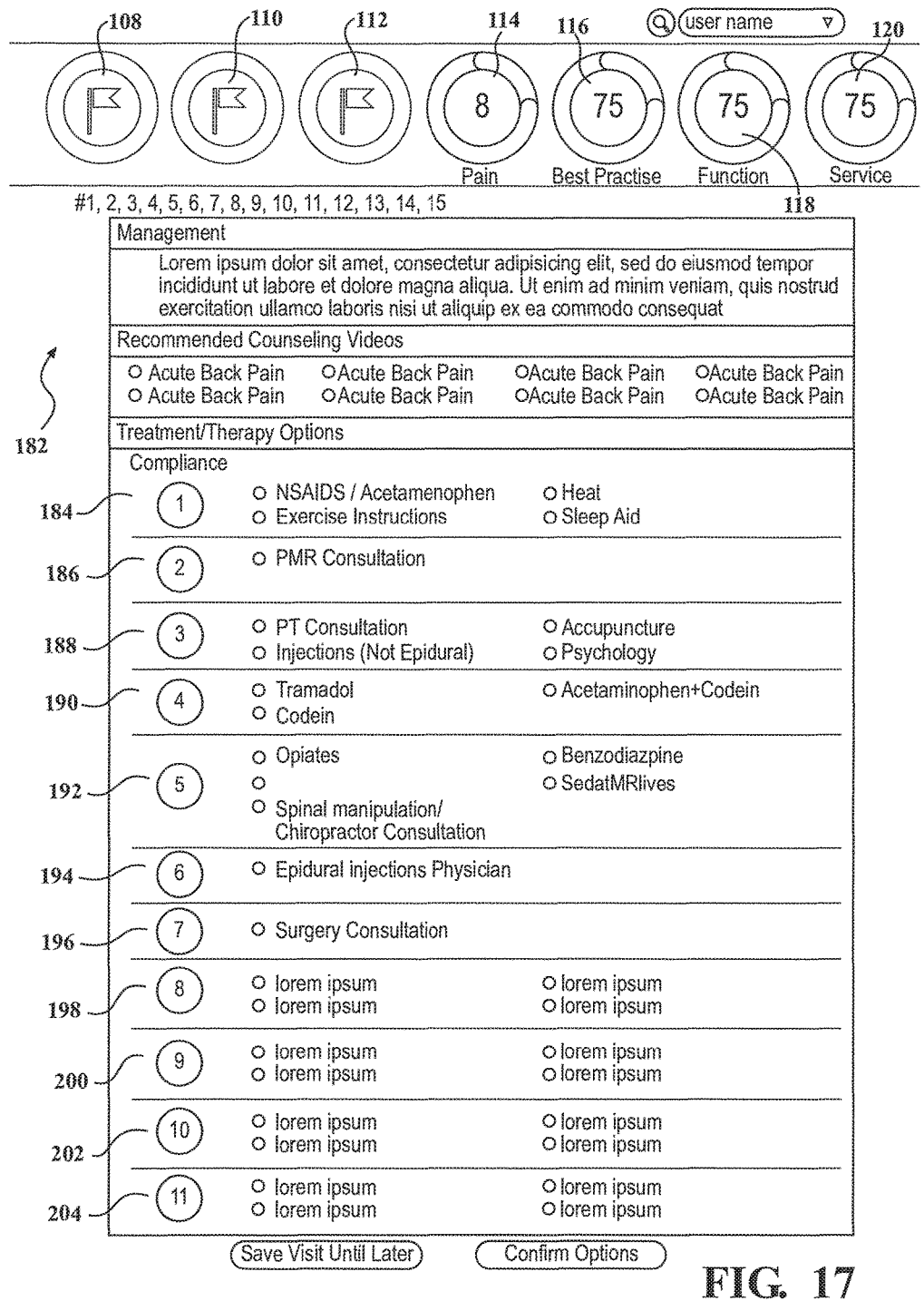
FIG. 17 is a management screen display and which provides compliance ratings for care providers, based upon stages or gradations of care ranging from in clinic care from the primary physician through specialist care and surgery.

FIG. 16 is a screen display 180 of a comparison graph of a functional score vs. group average for a given physician and which assists in tracking the real time performance of that individual relative to the overall group. FIG. 17 is a management screen display and which provides compliance ratings for care providers, based upon stages or gradations of care ranging from in clinic care from the primary physician through specialist care and surgery. The flag and rating fields 108-120 described in FIG. 9 are repeated, along with additional fields 184-204, these respectively designating a scale of compliance ranging from 1 (least intensive) to 11 (most intensive).

In application, the software/algorithmic based protocol can function in one instance to create a series of subroutines for operating the present system and which include a first such subroutine for assembling a best practices model in the form of a database interfacing with the processor device and which presents series of treatment options ranging from desirable to undesirable associated with a given type of service. A second subroutine provides a decision support system interfacing with the best practices database and processor device, the support system providing any of a grading or awarding system for scoring, in real time, performance metrics for each of any number of providers of the service.

A third subroutine outputs to a plurality of subset processor devices assigned to each of the providers, real time and continuously updated scoring of their performance metrics based upon the grading/awarding system and as a result of the treatment options selected and inputted by the provider. A fourth subroutine (such as which can be integrated into the third subroutine) incentivizes adherence by the providers to the best practices model by tying desirable performance metrics to financial incentives which are scaled to each treatment option.

Additional subroutines include providing and incentivizing patient input to the processor driven device in the form of at least one of medical/biographical data input and commentary/rating regarding the service provider. A management module can also include at least one additional subroutine interfacing with the processor driven device for monitoring and tracking adherence to the best practices model.

Additional subroutines can designate a sum of funds representative of an operating budget for the service provider and for disbursement on a percentage basis to each of any number of subset service providers based upon adherence to the best practices model. This can further include subdividing the sum between different practice groups and sub-specialties associated with a given class of service providers.

Addressing the initial example described in FIGS. 1-4, one subset application of the software based algorithmic medium can in particular include the treatment options associated with said first subroutine further including being integrated into a medical care protocol and further including any one or more of a first physician service provider assessing a patient's condition, a second physiatrist service provider further assessing the patient and interfacing with said first physician in an extreme diagnostic event, and a third surgeon service provider for additionally assessing the patient and interfacing with the second physiatrist service provider in at least an epidural related event. This can further include an MRI procedure associated with an interfacing event between the physician and physiatrist modules.

Figure 18:
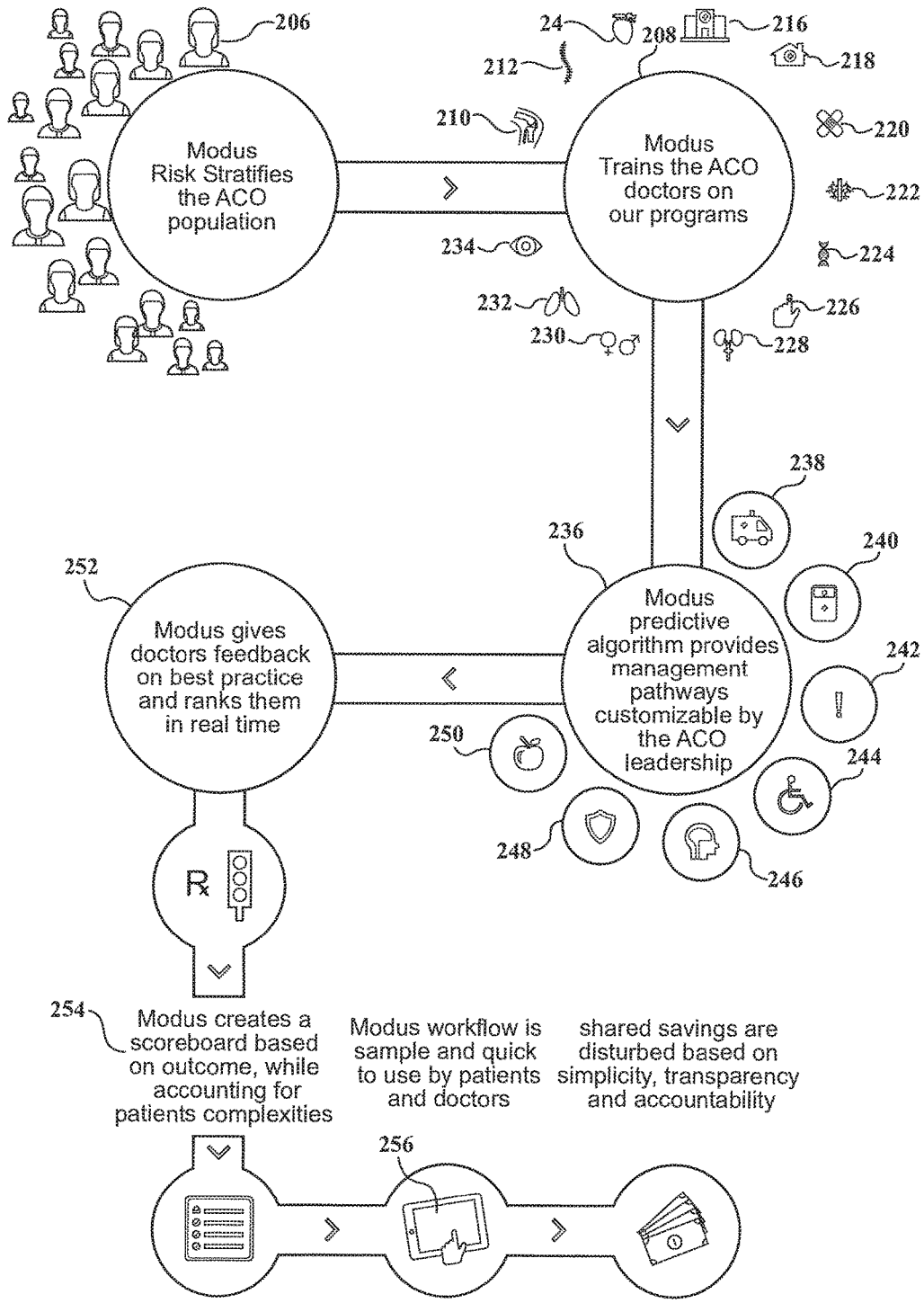
FIG. 18 is a flow diagram of the predictive algorithm of the further variant of the non-transitory computer writeable medium of the present inventions.

FIG. 18 is a flow diagram of the predictive algorithm of the further variant of the non-transitory computer writeable medium of the present inventions. As previously described, this variant of the non-transitory computer writeable medium incorporates a predictive algorithm which includes a series of protocols for modifying a base or template version of the algorithm into any of a number of modifications or sub-variants and in order to quickly and conveniently customize the computer writeable medium.

A first protocol 206 or subroutine for establishing a risk profile through stratifying a designated ACO population. For purposes of definition, the ACO population constitute a membership of a health care plan or other designated group of individuals for which medical coverage is provided and further for which a designated sum of funds is deposited or otherwise retained for providing payment for services rendered on behalf of the membership or target group.

A second protocol or subroutine, see at 208, of the predictive algorithm further operates by training the ACO doctors or other care providers in one or more of a series of medical related diagnosis and treatment programs (or disciplines) these further potentially including but not limited to any one or more of joint care 210, spine care 212, cardiac care 214, acute care 216, post-acute care 218, wound care 220, vascular care 222, cancer care 224, diabetes care 226, kidney care 228, urology care 230, pulmonary care 232 and vision care 234. In one non-limiting variant, a base algorithm is provided which includes a pre-programmed subroutine program or code directed to any one or more of the above care disciplines 210-234, it being further understood that the listing provided is open-ended and can be augmented or substituted by any other care specialty or sub-specialty for which an ACO can provided coverage.

A third successive protocol/subroutine includes establishing one or more management pathways which are customizable by the ACO leadership, see as designated at 236. By way of explanation, the customization or configuration of the predictive algorithm is facilitated by a series of questions and answers which are built into the customization aspects of the software and which are asked of the care providers assigned to one or more of the enumerated specialties.

In this fashion, the questioning protocol built into the pathways between the second 208 and third 236 subroutines provides for the necessary modification/customization of the base algorithm, such as for any one or more of a variety of treatment sub-species, and in order to establish subroutines at this stage for any one or more of emergency care 238, immediate care 240, systemic complications 242, disability risk 244, psycho-social issues 246, preventive care 248 and/or maintenance care 250. As previously noted, the lists provided herein are open ended and can be substituted or supplemented by additional care subspecies without departing from the scope of the inventions described herein.

A fourth protocol/subroutine 252 provides care provider (e.g. doctor) feedback on the desired best practices for the given diagnosis and treatment sub-species resulting from the question and answer protocol achieved in the third subroutine. As with the previous disclosed embodiments, this can include providing any type of grading or coding protocols, such as utilizing and combination of letters, colors or other generally identifiable symbols for conveying visualization of the grading of the specific care providers conduct as reflective of the pre-established best standards which are integrated into the algorithmic functions of the associated program.

A fifth protocol 254 results in the creation (again by the ACO or other provider) of a scorecard for each individual care provider (doctor, therapist, etc.), such based primarily upon patient outcome assessment and accounting for patient complexities. Such informational feedback, as previously described, can be communicated via electronic device (see handheld tablet as depicted at 256). In this fashion, shared savings resulting from the implementation of the program results are distributed based on the simplicity, transparency and accountability provided by the present system and computer writeable medium.

Proceeding to FIG. 19A, a screen illustration is generally shown at 258 of a patient information entry screen associated with the variant of FIG. 18 and which illustrates a series of fields which can be selected checked by the patient. These include individual Yes (check mark), No (X) or question (?) fields for selected symptoms including each of Night Sweat 260, Fever or Chills 262, History of Cancer 264, Recent Infection 266, Recent Trauma 268, Impaired Balance 270, Poor Coordination 272, Tripping or Falling 274, Loss or Changed Sensation 276, Numbness or Tingling Sensation 278, Localized Weakness 280, Paralysis 282, Neck Pain 284, Back Pain 286, Joint or Limb Pain, Stiffness 290, Limited Range of Motion 292, Swelling 294, Headaches 296, Anxiety or Depression 298, Stress of any Kind 300, Disturbed Sleep 302, Unintentional Weight Loss 304, Blood in Urine 306, Blood in Stool 308, Bladder or Bowel Problems 310, Abdominal Pain 312, and Other Symptoms 314.

A check mark (Yes) for any of these symptom fields further brings up a "Tell us More" data key entry field which allows the patient user to provide additional information. A similar field is brought up in the instance of the right side (?) icon being selected for entry of additional patient provided information. Other features include a Start Over button 316 and a Next button 318. The screen display 258 may further include a patient identity field 320 and a care discipline identifier 322 (see also Spine field 212 in FIG. 18).

FIG. 19B is a second screen illustration (divided into FIGS. 19B-1 and 19B-2) of associated with the patient informational entry page and providing a series of entry fields relative to such issues stress, pain, lost productivity, etc. Referencing FIG. 19B-1 initially, this includes entry fields for indicating pain in any one or more of arm 324, leg 326, lower back 328, neck 330, shoulder 332 or other 334. Also indicated are fields for days of work missed 336, duration of current pain 338 and last day of work 340.

An additional series of patient entry fields are provided for physical aspect of work 342, pain rating over previous week 344, average scale of pain over past 3 months 346, severity and frequency of pain episodes over past three months 346 and 348, and pain decrease success 350. Corresponding scale selections are provided for each of the additional entry fields 342-350.

FIG. 19B-2 also includes fields for each of tension over previous week 352, depression over previous week 354, current pain persistence risk 356, probably of working in 6 months 358, job satisfaction with current limitations 360, physical activity to pain correlation 362 and consequent rescission of work function 364, and cessation of normal work at current pain level 366. As with FIG. 19B, corresponding scale selections are provided for each of the additional entry fields 352-366.

Also depicted in FIG. 19B-2 are a selection of five activities, the patient entry answers to which are scaled from 0-10 and include each of "I can do light work for an hour 368", "I can walk for an hour 370", "I can do ordinary household chores 372", "I can do the weekly shopping 374" and "I can sleep at night 376". Previous 375 and Next 377 fields are located at the bottom of the page to facilitate either going back to screen page 19B-1 or forward to 19C.

FIG. 19C is a third screen illustration associated with the patient informational entry page of FIG. 19 and providing a series of entry fields relative to establishing a patient functional level. This includes a pain score bar 378 with an adjustable range between no pain and worst pain ever for each of Pain Intensity 380, Personal Care 382, Lifting 384, Walking 386, Sitting 388, Standing 390, Sleeping 392, Sex Life 394, Social Life 396, and Traveling 398. Also illustrated are previous 400 and submit questionnaire 402 fields.

FIG. 20A succeeds FIG. 19A-19C and provides a series of Review of System/Physician Clinical Decision informational entry page 404, such repeating the patient identity field 320 and care discipline identifier 322 from FIG. 18. This includes Positive Responses (field 406) designations for each of Loss or Changed Sensation 408, Numbness or Tingling Sensation 410 and Back pain 412.

FIG. 20A provides additional fields including "?Unsure" 414, indicating a sub-field for Bladder or Bowel Problems 416, as well as a Negative response field 418 indicating such as Night Sweat 420, Fever or Chills 422, History of Cancer 424, et seq. Other fields include Pertinent HPI and Other History 426, Pertinent Physical Examination Fields 428 and 430 and Medical Decision Making Field 432 including a variety of individual conditions 434 (including each of Infection, Fracture, Cancer, Cauda Equina, Pending Paralysis, Weakness, Radiculopathy, Ankylosing Spondylitis). An alternate "None. Continue" field 436.

Figure 20B:
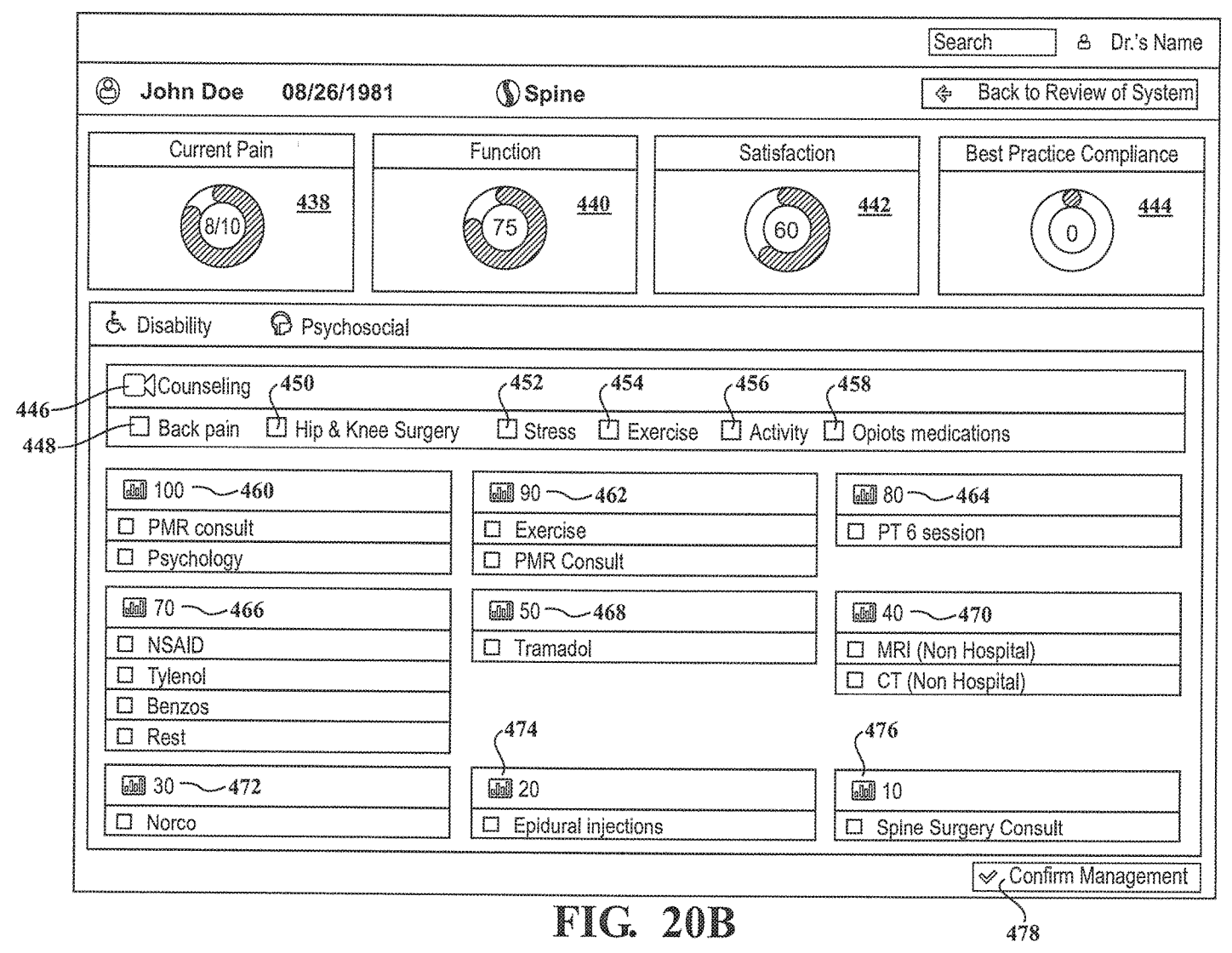

FIG. 20B provides a further screen illustration succeeding FIG. 20A for the care provider informational page and including g a series of informational entry fields along with real time displays for Current Pain 438, Function 440, Satisfaction 442 and Best Practice Compliance 444. Also provided are a series of provider entry fields for determining a treatment level for a selected disability or psychosocial malady. This includes counseling 446 such as for each of back pain 448, hip & knee surgery 450, stress 452, exercise 454, activity 456 and opiats, medication 458.

FIG. 20B also provides a series of physician/care provider entry selections for given treatment protocols, such corresponding to the real time tool bar functions 438-444. These include any one or more of PMR Consult or Pyschology 460 (at scale of 100), Exercise and/or PMR Consult 462 (scale 90), Physical therapy (PT) session 464 (scale 80), one or more of NSAID, Tylenol, Benzos or Rest options 466 (at scale 70), Tramadol 468 (scale 50), magnetic resonance imaging (MRI) or computed tomography (CT) 470 (scale 40), Norco 472 (scale 30), Epidural injections 747 (scale 20) and Spinal Surgery Consultation 476 (scale 10). Confirm management selection 478 progresses to the last screen, FIG. 21, described as follows.

Figure 21:
FIG. 21 is a counseling and feedback screen illustration regarding management pathways established in FIG. 18.

FIG. 21 is a counseling and feedback screen illustration 480 regarding the management pathways established in FIG. 18. Again repeated is the patient identity field 320 and care discipline identifier 322 from FIG. 18. Also repeated are the Current Pain 438, Function 440, Satisfaction 442 and Best Practice Compliance 444 fields from FIG. 20B.

FIG. 21 provides for physician counseling for patients, as well as instant (real time) feedback on management choices determined in the flow diagram of FIG. 18 (between steps 308 and 236 as described above). As previously explained, the pathway and options for management changes depend on the patient informational input, as well as the physician's answers to the questions posed between the steps in the FIG. 18 flow diagram.

An Emergency Care section 446 includes a Counseling field 448 which is customized to indicate which sub-fields taken from Back Pain, Hip & Knee Surgery, Stress, Exercise, Activity and Opiats medications have been checked. The feedback aspects of the Management page 480 further provides scaled selections 100, 90, 80, 70, 50, 40, 30, 20 and 10. A designation (check) of one of these boxes corresponds to each of Stat MRI/CT (for one hundred at 450), Stat Neurosurgery Consult (for ninety at 452), Direct Hospital Admission (for eighty at 454), ER (for seventy at 456), PMR Consultation (for fifty 458), NSAIDS (for forty 460), Opiates (for thirty 462), Benzos (for twenty 464) and PT or physical therapy for the lowest percentage or scale (for ten at 466). Also indicated is a confirm management screen 468 for designating confirmation of review by the Payor/ACO.

Figure 22:
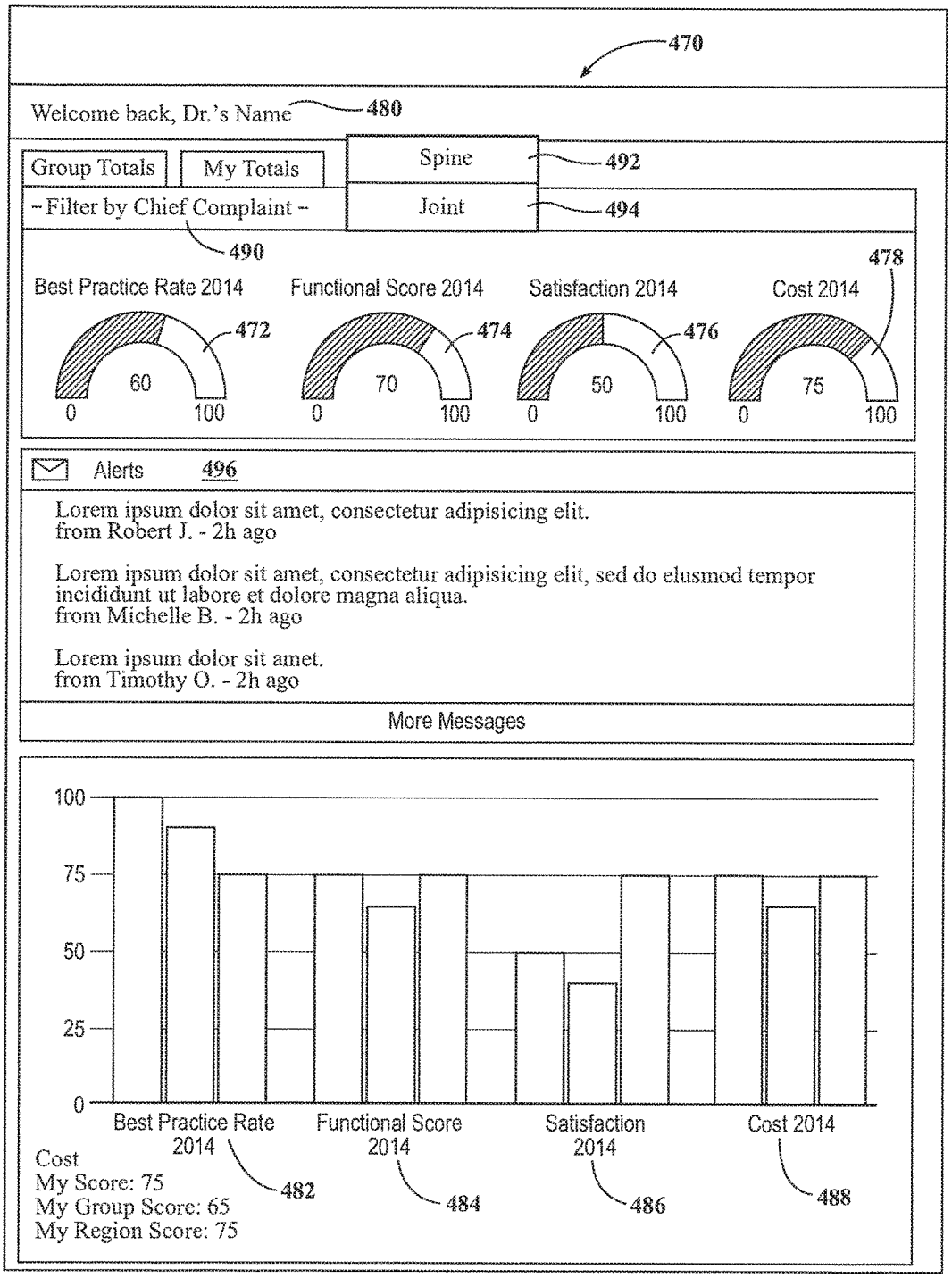
FIG. 22 is a screen illustration of a dashboard page indicating real time updated metrics including Best Practice Rate, Functional Score, Satisfaction and Cost, such further including ratings for each of individual score, group score and regional score.

Finally, FIG. 22 is a screen illustration of a dashboard page 470 indicating real time updated metrics for each of Best Practice Rate 472, Functional Score 474, Satisfaction 476 and Cost 478 (in each instance for selected year 2014). Aspects of this page may also include identification of given car provider 480 for which scoring is provided.

Each of Best Practice Rate, Functional Score, Satisfaction and Cost may further be further subdivided to provide breakout ratings or scores for each of individual/group/region, as further shown at 482, 484, 486 and 488 respectively, such again in ratings of 0-100. Also shown is a Filter by Chief Complaint Field 490, such including further selectable fields including each of spine 492 and joint 494. Alert field 496 also provides for providing additional feedback and communication between the payor (ACO) and the care provider.

Given the above description, the present invention (including each and all of the system, method and non-transitory computer writeable medium) accordingly provides an incentive structure for rewarding care providers based upon best practice decision making (quality or outcome dependent) and not merely upon quantity of services provided (e.g. tests ordered, surgical procedures conducted etc.). In this manner, health care dollars are more equitably distributed as well as saved by such a merit/outcome based sharing and distribution scheme, such that the service care provider (physician or other like) can also be paid a bonus as an incentive for keeping their patients/clients more healthy, more able (less disabled) ad more satisfied, as well as preventing the administration of unnecessary treatments and procedures such as are attendant with current quantity of service based compensation models.

Variants of the present system also contemplate a pool or bundle of funds being designated (such representative of historical costs incurred for any given number of physicians or practice groups, including tiers of care providers drawn from PMP (primary care physicians), specialists (cardiology, spinal surgery, etc.), these being paid out on a percentage basis to the various care providers based upon their individual scorecard results regarding adherence to the best practice protocols established by the relevant ACO/care provider, such further reflecting the results/outcome of the treatment provided (i.e., outcome driven performance by the physician or other care provider based results and not compensated as a variable of the quantity of, often unnecessary, services).

Additional advantages include the establishing of performance metrics for clinical providers that are based on adherence to best practice, patient's functional outcome, patient satisfaction and cost. Adherence to the model created in the present invention further derives from the authority implicit in the local ACO or other payer and, along with the creation of transparent metrics for achieving higher compensation levels, serves to more equitably distribute shared savings and other financial incentives between all of the various stake holders (patients, care providers, and payers).

Other advantages of the system include the ability to readily monitor and record the providers/physician's choices in a real-time decision tree which interfaces with the decision support system module and which is reflected in the continually updated scorecard for each such physician/provider. In this fashion, real time feedback to the physician is achieved to monitor ongoing activity in regards to the diagnosis and treatment provided, with the incentive driven compensation structure in place for guiding and influencing such decision making in the directions dictated by the ACO/payer.

In this fashion, the present system, method and computer writeable medium provides a tools to the management portion of the operation or model (e.g. payers, provider organizations, ACO's, etc.) for carrying out the management of the provider's preferences and behavior (as again dictated by the formulated best practices protocols), such further enabling the management portion to control utilization and expenditure of the resources allocated to such care.

In this fashion, customization of the present system is made possible of the best practices formulated, such by the responsible payer or ACO for various types of disease management based upon the manager's (payer's/provider organizations/ACO) preference) and which can further be modified for any criteria or input not limited to differences in geography (i.e. best practices may vary from locale to locale and the present system builds in the flexibility to take this into account). The real-time performance metrics achieved by the present system also enable instant feedback to the providers to both assess current practice and to provide direction (along with accompanying incentives) for adhering to the formulated best practice protocols for present and future treatment of the patient.

The report card aspects also provide comparison metrics for each of the providers/physicians, this further providing a competitive environment (not driven exclusively by dollars) for adopting and adhering to the best practice protocols formulated by the management portion (e.g. including or representing the interests of the payer). The reward mechanism of the present invention is also modified and calibrated to cover any type of care provider (or groups of care providers) not limited to primary care physicians, specialists, or combination/groups of such providers which may be incorporated into a given practice or other entity.

The additional advantage of providing a reward mechanism for participation of the patient (not limited to providing coupons or rebates for undertaking data entry functions), further assists in maximizing the efficiency and economy of the medical records component of the system, as well as assisting in the formulation of correct and unbiased scorecard evaluations of each provider/physician by integrating the patient experience and input into the incentives driving the system.

Summarizing, a listing of the objective made possible by the present inventions include, but are not limited to, each of the following:

1. Establishing an algorithmic computerized medical providers scorecard.

2. Providing an algorithmic computerized operational tool to promote providers collaborations, coordination, integration and shared decision making.

3. Establishing an algorithmic computerized operational method for bundle payment management.

4. Creating an algorithmic computerized operational model for paying for performance.

5. Using an algorithmic computerized reward/incentive system to encourage providers to follow of best practice.

6. Establishing algorithmic computerized performance metrics for clinical providers that are based on adherence to best practice, patient's functional outcome, patient's satisfaction and cost.

7. Creating an algorithmic computerized transparent operational model for the distribution of shared savings and other financial incentives between all stakeholders (patients, providers and payers.

8. Algorithmic computerized system for monitoring and recording of providers choices in a decision tree.

9. Provide real time, instant algorithmic computerized feedback for providers compliance with best practice on every patient enrolled in the program.

10. Providing an algorithmic computerized tool to managers (payers, providers organizations/ACOs) for management of providers preference and behavior and enables the management of providers groups to control utilization.

11. Customizable algorithmic computerized best practice options for disease management based on the managers (the payers/providers organizations/ACO) preference (given best practice can vary geographically).

12. Providing algorithmic computerized real time, instant feedback for providers for overall year to date compliance for their patient population.

13. Providing an algorithmic computerized comparison metric for providers to measure their performance vs others in the group and other groups.

14. Enabling the managers (the payers/providers organizations/ACO) to use algorithmic computerized to create and manage an editable specialty physicians providers network.

15. Use algorithmic computerized System for empowering patients and providers teams by linking the individual provider financial incentives to the patient's and team's experience.

16. Creating an algorithmic computerized system to use as a reward mechanism for patients' compliance with care and electronic data entry into the providers medical records system.

To summarize, and drawing on the above disclosure, the predictive algorithm of the present invention (MODUS) provides for risk stratification of the population and, based on the results extracted, (co-morbidity's, Socioeconomic, psychosocial and other risk factors), the Modus predictive algorithm provides clinical management pathways, that are customizable by the ACO's (the providers group) leadership or the healthcare payer (insurance carriers of self insured employer).

The pathways are meant to:
a. Be a check list reminder process about best practice on routine/common clinical conditions (to help providers remember the mundane "stupid" items, that can cause significant problems if they are missed.
b. Preventive care reminders for various propulsion needs.
c. Standardize care based on beast practices guidelines
d. Inform providers at all levels (PCP, specialists and others) of the ACOs expectation for managing their population with various clinical conditions and co-morbidity's (Doctors will feel confident and less anxious about making care decisions that are researched, informed and recommended by their ACO)

Pathways starts with a basic low risk and complexities (Maintenance care), and built up as risks and complexities increases in a patient (Emergency care, immediate care, Systemic complications, Disability risk, Psycho-social and preventive care)

Pathways will increase flexibility for the ACO to focus time and resources allocations on the highest risk patients.

Additional envisioned embodiments include applying the system, method and associated algorithmic based (software) medium to other medical and, potentially, non-medical applications beyond those described herein, such as including but not limited to orthopedics conditions, diabetes care, cardio-pulmonary related chronic conditions, cancer and the like.

Depending further on the chronic condition we are managing, the present system and model will be adjusted accordingly and appropriate clinical providers will be deployed for it and outcome measures will be adjusted to be relevant to the chronic condition. Subject to modification, the providers will generally be PCPs (primary care physicians), then a non-interventional specialist and an interventional specialist. For example in cardiac care the team will include PCPs, cardiologists and interventional cardiologist and cardiac surgeons (along with teams of dietitians, physical therapist, exercise physiologists, trainers) as well as relevant educational material that will be provided to the patients.

Given the above discussion of the modules covering the rating system, process and medium for establishing best practices compliance tied to compensation (FIGS. 1-17) and for establishing an optimizing a predictive algorithm for treatment of patient conditions (FIGS. 18-22), the present inventions additionally disclose a pair of related modules covering both workman compensation (FIGS. 23-44) and general ACO/insurer rehabilitation (FIGS. 45-51) variants. In each case, the workman comp and rehab modules are configured utilizing many similar components as associated with the previous variants and provide for optimizing the diagnosis, treatment and resolution of either of worker or general patient injury events.

As will be further described, and in associated with a workman compensation claim, the module improves upon the existing paper based model for documenting and processing such claims, this by synthesizing, in a digital environment, all of symptom, treatment and progress variables in a multi-party available format. In particular, the injury event module greatly increases care provider (physician) efficiency by integrating and compiling electronically, in easily readable and time elapsed formats, symptom and treatment variables. The module additionally provides a reasonable and agreeable model, such as between the employer/payer and worker, for establishing minimal goals for facilitating return to work.

Prior employing the workman compensation module, the employer/payer (also ACO as previously defined) will choose a providers network, e.g. a group of medical professionals and ancillary support staff including personal therapists, pharmaceutical staff, imaging specialists, hospitals, and the like. As per the initial module of FIGS. 1-18, a best practices model is established with corresponding payment and fee schedules and, as further depicted in succeeding FIGS. 19-22, predictive algorithms are integrated for establishing specific recommended treatment protocols.

At this point, and referring initially to FIG. 23 a supervisor/employer information entry screen 500 is provided (such as again integrated into a processor based device)

which, following the occurrence of a worker injury event, constitutes the initial action in the opening and reporting of the event. A series of entry fields include each of Supervisor Name 502, Company 504, Position 506, Email 508, Phone 510, Address fields 512 and 514, City 516, State 518, Zip Code 520 and Continue button 522.

FIG. 24 is a succeeding supervisor/employer information entry screen, at 524, to that shown in FIG. 23 for inputting injured worker details and including fields for each of Worker Name 526, Date of Birth 528, Email 530, Phone 532, Address fields 534 and 536, City 538, State 540, Zip Code 542, Injury Details 544, Description of Injury field 546, Injury Date 548, Injury Time 550 and concluding with Job Duties 552 for the supervisor/employer to list the routine job duties of the worker. Following clicking submit button 554, and proceeding to FIG. 25, a doctor assignment screen 556 is provided which the module produces in response to the inputs of the information entry screens of FIGS. 23-24 for assigning a doctor of suitable qualifications and training (i.e. trained in physical medicine and rehabilitation or PMR, occupational medicine, sports medicine, etc.) for treating the injured worker.

For convenience, the doctor assignment screen further includes address and map information and, as will be described throughout the succeeding screens of the workman comp module, the physician/doctor's role at this point is to establish a patient/physician relationship (i.e. to function as the primary care physician and to examine and treat the worker's injury). As will be further described, the doctor further functions to assist in setting up realistic and achievable goals for recovery of function of the patient/worker over a given time frame, the objective being to facilitate return to work once minimal and commonly agreed to metrics (as between physician/payor/worker) are achieved.

Following clicking on continue button 558, a Confirmation of Details page 560 at FIG. 26 is accessed in which a number of personal fields are listed, including biographical fields for each of Patient Name 562, Date of Birth 564, Last Four Digits of Social Security 566, Email address 568, Phone Number 570, Address fields 572/574, City 576, State 578, Zip Code 580, Emergency Contact fields for Name 582, Relationship 584 and Contact Number 586, and finally Family Doctor (regular PCP) Name 588 and Contact Number 590. For purposes of security, Password 592 and Retype Password 594 fields are also provided and, once completed Continue button 596 is accessed to advance to Confirm Injury Details screen display 598 of FIG. 27.

FIG. 27, based on the information previously inputted, provides an explanatory (non-editable) field for Injury as described by your supervisor 600 as well as a worker input field 602 for inserting additional injury details. Also listed are a series of duty fields as previously recorded by the supervisor for review by the worker for purposes of assessing accuracy, this intended to provide an exemplary and non-limiting summary of the typical performance metrics which the worker is expected to achieve.

By example, FIG. 27 provides such a non-limiting summary as including performance metrics for "Lifting 20 lb every 1 hour" (600), "Driving a hilo 3 hours a day" (602), "Picking material off 3 hours a day" (604), "Cleaning containers" (606), "Rolling Sheets" (608), "Typing on a Computer" (610), "Walking between work stations" (612), "Managing inventory" (614), "Calling on staff members" (616), "Answering phone calls" (618), "10 hours/day" (620), and "4 days a week" (622). In this manner, FIG. 27 also provides additional entry fields for the worker/injured party to fill out including confirming details of the injury as reported by the supervisor, as well as confirming and updating the scope of duties as provided, following which submit button 624 is accessed to advance to the patient treatment portion of the module.

Figure 28:
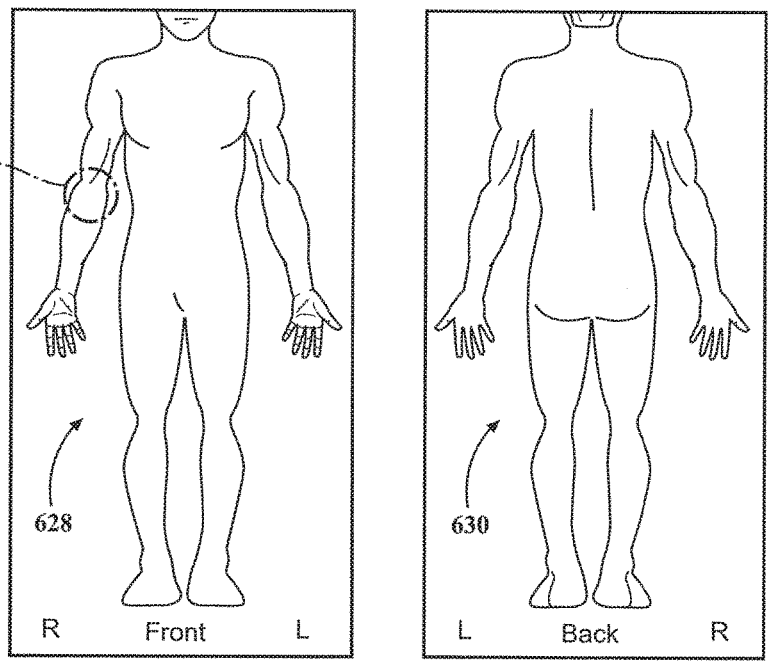
FIG. 28 is a first symptoms input screen for the worker/injured party to indicate present physical symptoms/conditions.

Proceeding now to FIG. 28, a first symptoms input screen 626 is provided for the worker/injured party to indicate present physical symptoms/conditions relating to the treatment stage. As with each of the succeeding screen displays through FIG. 39, a pair front 628 and back 630 pictorial representations are provided of a patient and in which the patient (either alone or in the presence of the participating physician) can indicate a physiological location (see inner right elbow 632 in representation 628). Additional fields are provided for indicating pain intensity (at 634) with an associated 1-10 pain scale (at 636).

A further field 638 is provided for indicating type of pain (see selecting fields for Aching 640, Stabbing 642, Burning 644 and Numbness/Tingling 646). Comment field 648 is also provided and includes entry location for comments (at 650) such as when pain started, what caused it, what makes it better or worse, other symptoms, etc. Also provided is an add symptoms area 652 and, in combination with list fields for Location 654, Type 656, Intensity 658 and Other Symptoms 660, facilitate listing of the additional symptoms. FIGS. 29-30 are general repeats of the symptoms input screen of FIG. 28, at 662 and 664, respectively, with pain intensity level 636' (at 6) indicated in FIG. 29 and aching pain 640 designation provided in FIG. 30.

Proceeding to FIGS. 31-39, illustrated are a progression of symptoms catalog screens for weeks 1-9 from date of injury event and providing, for the viewing benefit of all of the treating physician, the injured worker, and the ACO/ payor/employer condensed/synthesized and time elapsed progress metrics displaying and tracking the injured worker's improvement in condition and function. Referring first to FIG. 31, a screen illustration 666 is provided again showing the front 628 and back 630 pictorial representations, the back illustration further including pain indications 640, 644, 646 et seq. which can be entered by either point and click and/or by capacitive touch (tactile) interface.

Pain Record entry fields are further provided for each of Neck 672, Shoulder 674, Arm 676, Forearm 678, Hand 680 and Head 681, each depicting a selected variety of pain fields again including each of Aching 640, Burning 644 and Numbness/Tingling 646. Pain Intensity indicator 682 provides a range (typically between 1-10) for each of the afore-mentioned areas of pain, with Comments field 684 provided for listing any related patient conditions.

Figure 32:
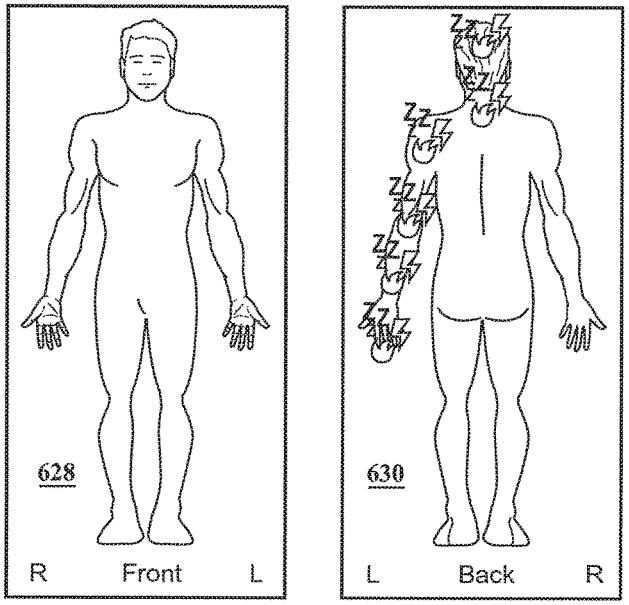
Figure 33:
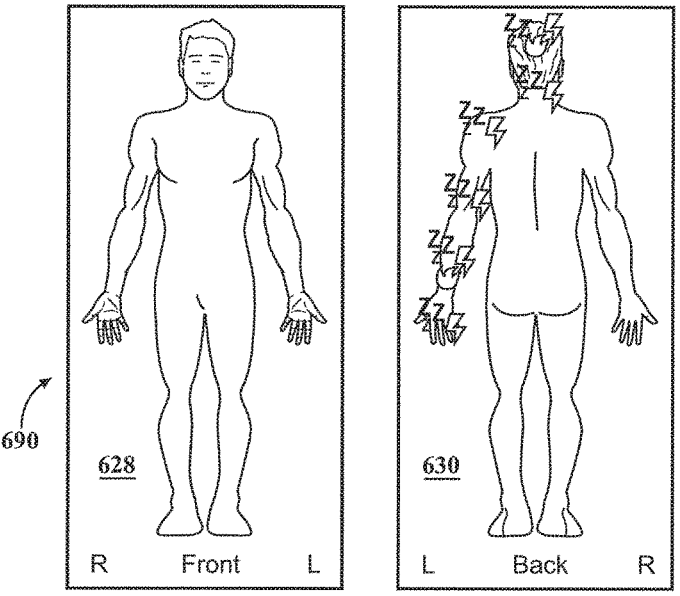
Figure 34:
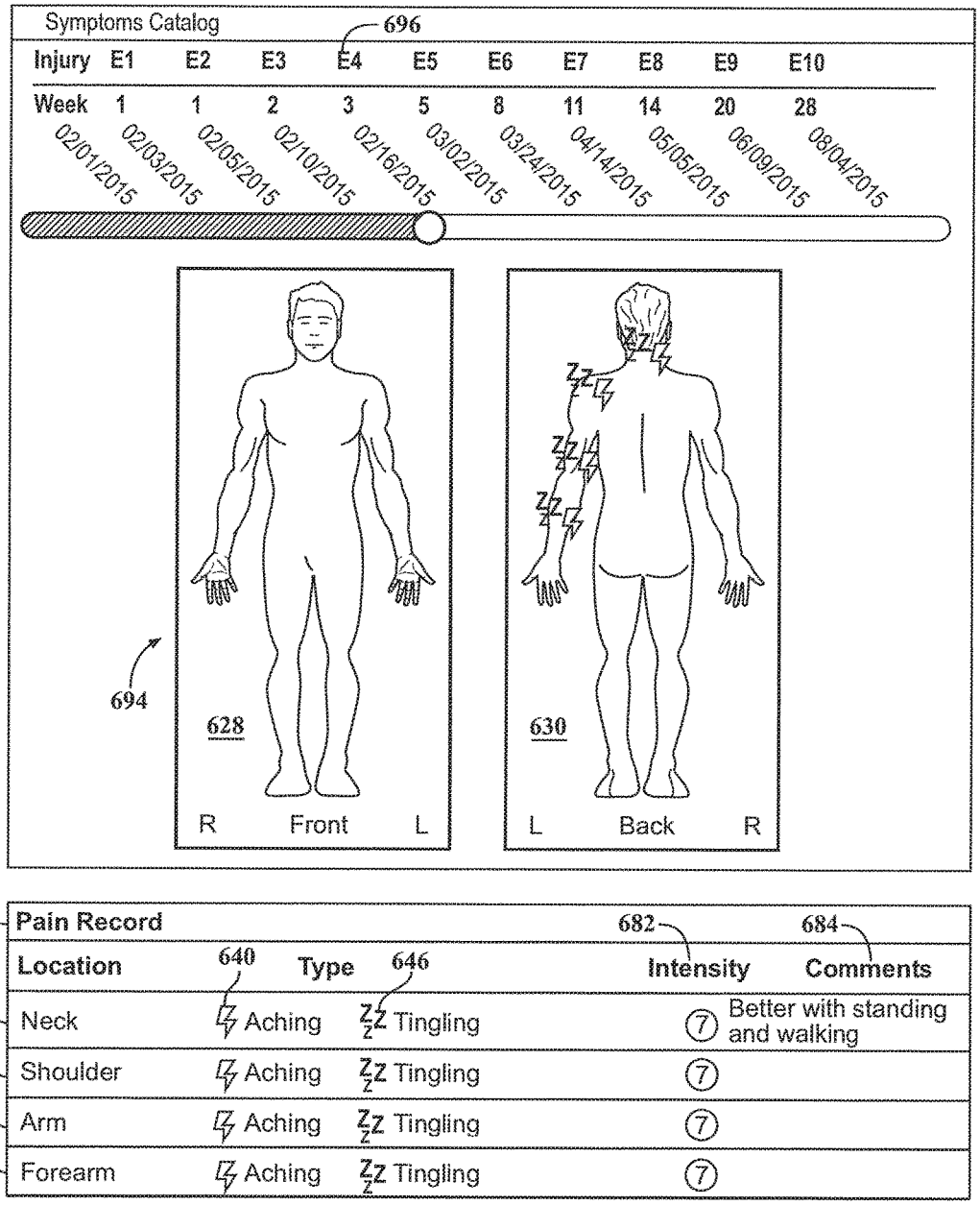
Figure 35:
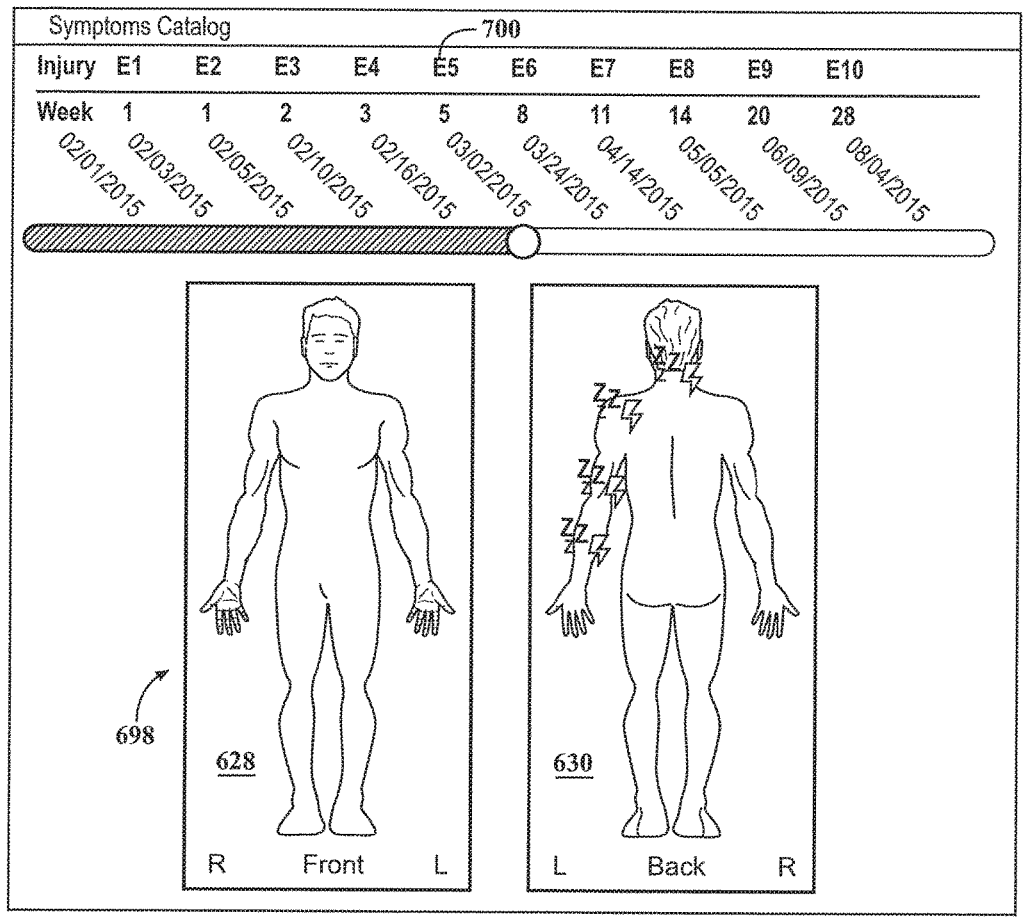
Figure 36:
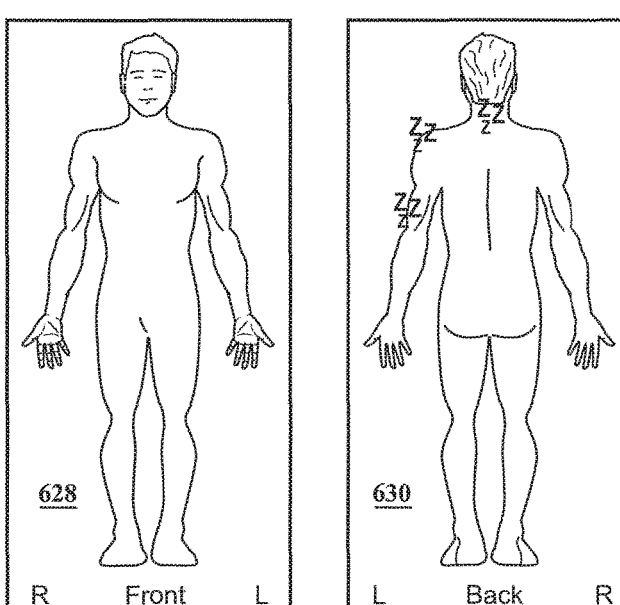
Figure 37:
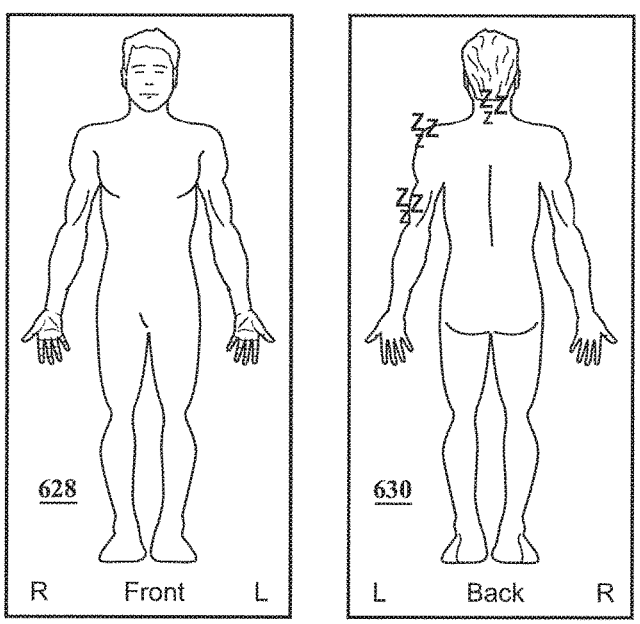
Figure 38:
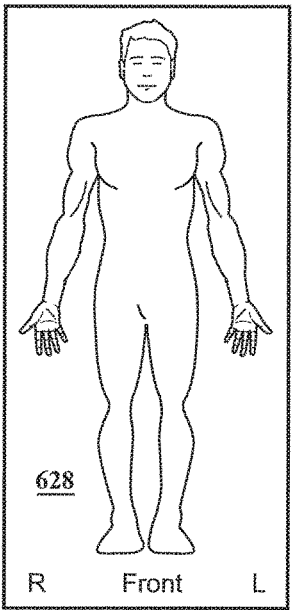
Figure 39:
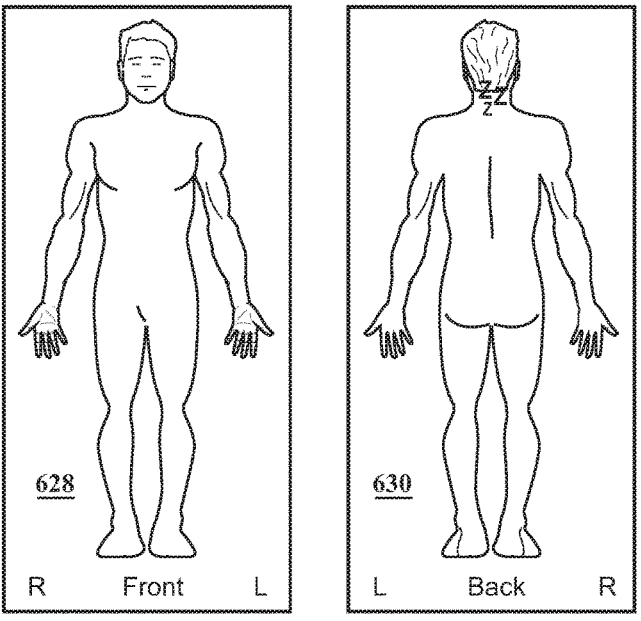

FIG. 32 provides a succeeding screen illustration 686 of a Symptoms Catalog for a further time interval shown at 688 as corresponding to week 2 from an injury event. Further succeeding screen illustrations are shown at 690 for week three 692 (FIG. 33), at 694 for week four 696 (FIG. 34), at 698 for week five 700 (FIG. 35), at 702 for week six 704 (FIG. 36), at 706 for week seven 708 (FIG. 37), at 710 for week eight 712 (FIG. 38) and, finally, at 714 at week nine 716 (FIG. 39). As further shown, the pain intensity variables are shown decreasing from week to week (FIGS. 31-39) for pictorial depictions 628 and 630 and associated intensity readings 682.

The Pain Record, Intensity and corresponding pictorial representations as shown also decrease in both quantity and intensity over the course of FIGS. 31-39 (week one to week nine) corresponding to the improvement of the worker/ patient and such that, by week nine, only minor neck pain 672 remains with numbness 646 at pain intensity level two. In this fashion, the module provides a condensed and synthesized record of past and current patient metrics (pain type, level, etc.) which enable the physician to optimize present and future treatment protocols (these again consistent with the previous best practice module (FIGS. 1-17) and predictive algorithm module (FIGS. 18-22) to ensure that the correct and optimal treatments are applied to the injured worker/patient in order to expedite patient recovery.

Proceeding to FIG. 40 a first worker ability input screen 718 is shown forming a portion of a related sub-component of the workman compensation module and depicting a number of entry fields which specify current ability metrics of the worker/patient. These include patient inputted (or supplied) current ability for a non-limiting listing of duties, such as particular to the expected abilities of a given job description and including each of "A. Lifting 20 lb every 1 hour" (at 720), "B. Driving a hilo 3 hours a day" (at 722), "C. Picking material off 3 hours a day" (at 724), and "D. Cleaning containers" at (726).

As further shown, the ability ranges can include any given percentage breakdowns, such as shown including effort percentages which the worker/patient needs to expend in order to accomplish each of the enumerated duties for each of 1-25% (at 728 for Minimum Effort), 26-50% (at 730 for Moderate Effort), 51-75% (at 732 for Severe Effort), 76-100% (at 734 for Extreme Effort) and, finally, >100% (at 736 for Physically Unable). As further shown, a score column (at 738) is provided for tallying grades of between one to five for each duty (e.g. as shown minimum effort corresponding to a score of five, moderate a score of four, severe a score of three, extreme a score of two, etc.). An average grade (see 3.5 at 740) is indicated for providing a Current Ability of the injured worker patient (as further determined by a date 742 indicated at the top of the screen). Finally, submit button 744 provides for entering of the data screen information and advancement to the next screen (FIG. 41 as described).

FIG. 41 is a related worker ability screen, at 746, which combines the current ability inputs of FIG. 40 with established goals (defined as goal ability 748) constituting a reachable performance ratio discussed between the physician and patient and which may also represent an intermediate or final metric which needs to be achieved in order for the worker to be cleared to return to partial/limited or full duties. This discrepancy (or difference) between the current ability 740 and goal ability 748 is further indicated as an ability gap (at 750) and submit button 752 enters the information of screen FIG. 41 prior to advancing to subsequent FIGS. 22-24.

Figure 42:
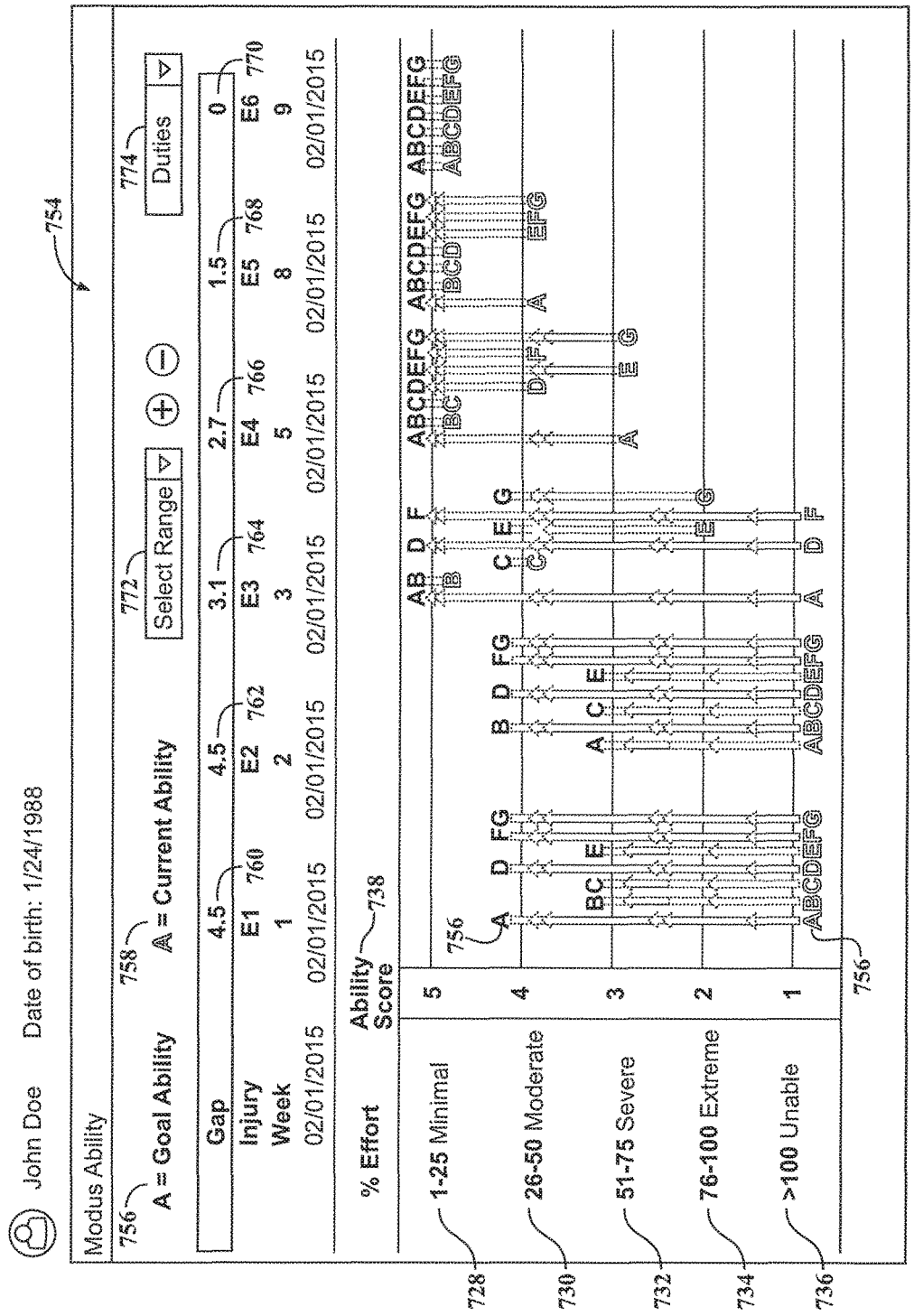
FIGS. 42-44 are a progression of time charted ability screens which track patient/injured worker current ability with goal ability over time intervals, the objectives of which are to facilitate use by all parties and in particular by the treating physician in the establishment and, if necessary, modification of the treatment protocol for obtaining faster patient recovery and achievement of (commonly agreed to) goals to enable return to work.
Figure 43:
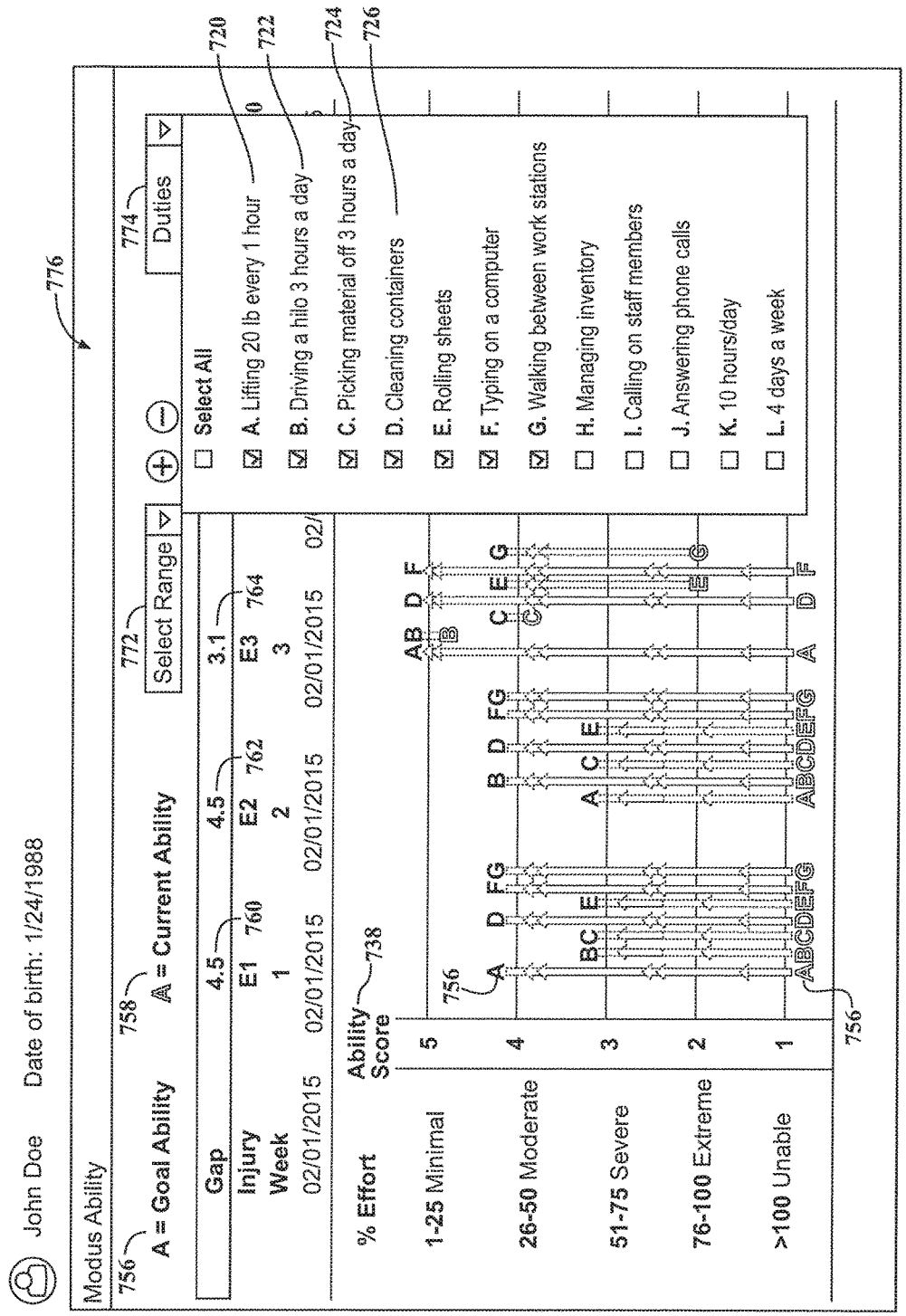
Figure 44:
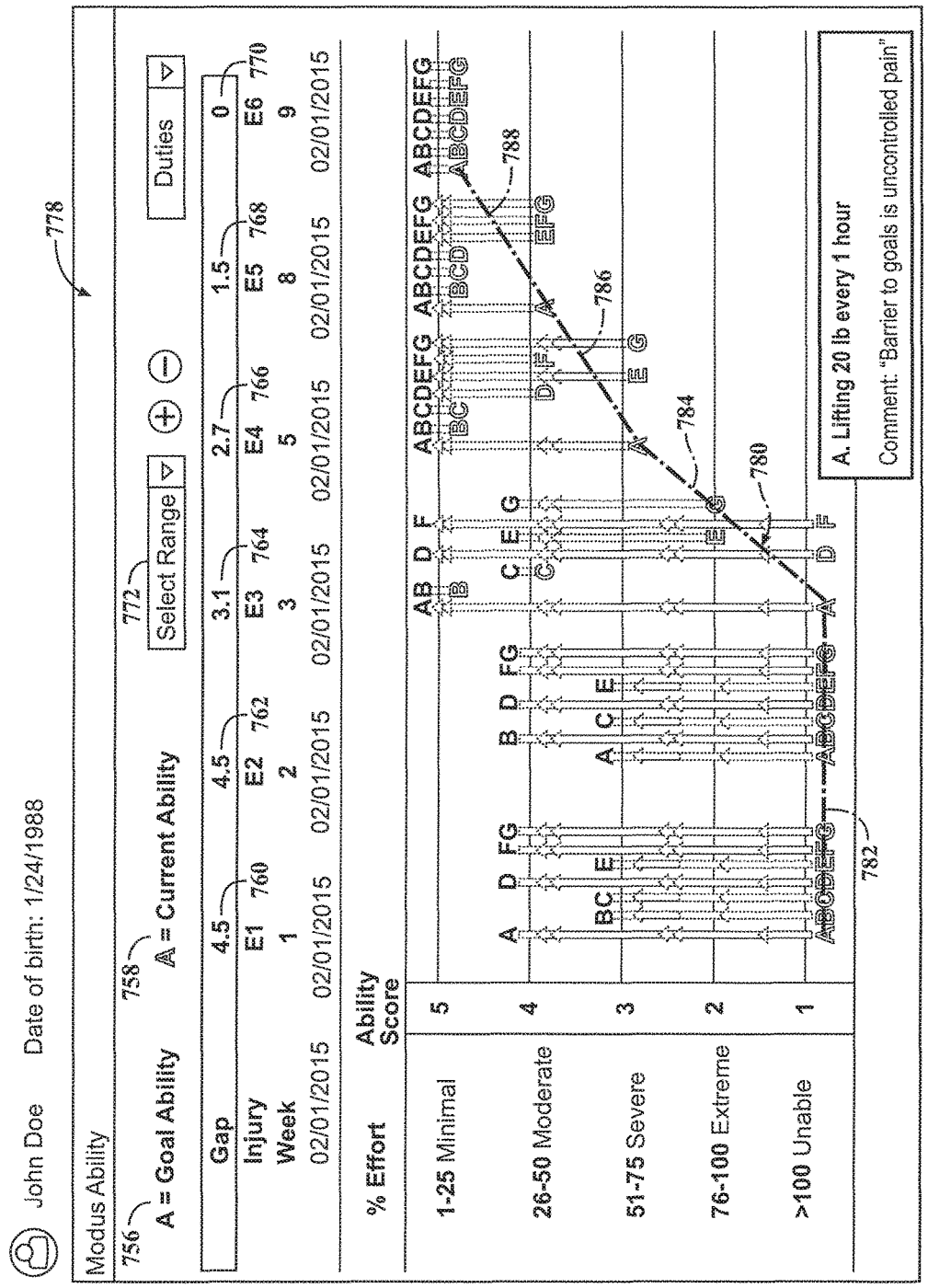

Referencing now each of FIGS. 42-44, a progression of time charted ability screens are provided which track patient/injured worker current ability with goal ability over specified time intervals (such as is shown on a weekly basis), the objectives of which are to facilitate use by all parties and in particular by the treating physician in the establishment and, if necessary, modification of the treatment protocol for obtaining faster patient recovery and achievement of (commonly agreed to) goals to enable return to work. FIG. 42 (ability screen 754) establishes a range on a weekly or other time interval established basis for each of goal ability 756 and current ability 758 for each of the previously identified duties 720, 722, 724, et seq.

As such, FIG. 42 compiles and presents, for the benefit of physician by optimizing the efficiency and minimizing the time investment in the treatment of the injured worker, data points for each of the afore-mentioned duties in the form of graphical ranges between current ability and goal covering a given succeeding time intervals (see gap 4.5 for week one at 760, gap 4.5 week two at 762, gap 3.1 for week three at 764, gap 2.7 for week five at 766, gap 1.5 for week eight at 768 and, finally gap 0 for week nine at 770). Drop down menus for selecting range (plus or minus for 772) and duties (further at 774) are also provided. As further shown, the ranges between current ability and goal ability, and corresponding gap, decrease from the first recordation (again week one at 760) following the injury event to the final recorded event (week nine at 770), such corresponding to an achieved metric which has been previously agreed to between the employer/supervisor and the worker as part of a workman compensation negotiation for facilitating a return to work event.

Succeeding screen 776 for FIG. 43 substantially repeats the information from screen 754 of FIG. 42, with the duties menu 774 selected to indicate such as those duties previously identified at 720, 722, 724, et seq., and referenced as A-L. The current and goal ability metrics are further presented in both light (current 758) and dark (goal 756) shading in the corresponding range depictions in order to provide a quick graphical interface to indicate a progression of the shrinking or minimizing of the degree of range or gap between current and goal abilities week to week until the gap is minimized or eliminated.

FIG. 44 provides a yet further representation at 778 of a graphical progression (see generally at 780) which is assembled by the present module algorithms and which is intended to represent an overall progression of current ability over time. As shown, the graph 780 includes a first linear component 782 representing weeks 1-3 which can correspond to initial post injury time intervals in which the treatments prescribed by the physician are not effective in the treatment of the injured worker/patient.

As further shown, and at week 3, the treating physician presumably changes the treatment protocol (such as again assisted by the best practices and predictive algorithm components previously described), the result being that succeeding linear component (at 784 for weeks three to five, at 786 for weeks five to eight, and 788 for weeks eight to nine) correspond to a quick visual confirmation for the benefit of the physician/patient/employer, etc, as to the efficacy of the subsequent treatment protocols concluding in the return to work event. In this fashion, the injured worker will utilize the module to describe the injury details (typically during the first physician visit), record the symptoms associated with each subsequent visit and record ongoing functional metrics regularly during each subsequent appointment (or encounter). For purposes of calculation, the graphical datum points are understood to generally correspond to an averaging of all of the duties (A-G) for a given time interval, understanding that the ranges for each specific duty at each given interval will vary and a composite or average datum score (as between current and goal abilities) is desired for determining general improvement of function (as further defined by the upward angle of the graphical portions 784, 786 and 788 terminating in the achievement/triggering of the back to work event.

As described, the advantages of the workman compensation module (FIGS. 23-44) provide for all of the employer/payer, the physician (PCP or other therapist) and the injured worker/patient to be able to utilize the same in order to monitor case progress and worker function, to approve or deny treatment options, to open or close claims, and to maintain record keeping with Electronic Injury Record (EIR) features associated with existing software for handling such workman compensation claims. In this fashion, the workman compensation module can be configured to interface, to the extent necessary, with existing electronic software associated with previously existing workman compensation electronic claims modules (much of which is limited to pdf scanning of existing paper forms with little else in regards to electronic interface-ability or functionality).

Proceeding now to FIGS. 45-51, a further related rehabilitation module is presented, such as not limited to a worker injury event but also including any injury event associated with a typical accountable care organization (generally defined as any of a provider network as previously identified, insurer, or other payee) in a general health application is provided for establishing and tracking a patient's functional (FEM) measurement score. As with the workman compensation module, the rehabilitation module integrates the establishment of current conditions, achievable goals, and time based tracking of the patient treatment (including time elapsed changes in response to flat line response indicating a non-effective treatment plan) in order to define a patient goal outcome and to optimize real time treatment and progress tracking to that goal. To this end, many of the features previously described, including the establishment of the ACO/payer with best practices model, the customizable management pathways, the training and assigning of care providers, etc., is repeated from the previously described workman compensation variant such that repetitive description is not required.

Figure 45A:

The above stated, FIG. 45, subdivided into subset screens 45A & 45B, presents a first rehabilitation setting input screen, generally at 790, according to a further module and providing a series of patient entry fields such as for each of prior function, current function and goal function. These include in the illustrated embodiment for each of "A. Self Care" (at 792), "B. Sphincter Control" (at 794), "C. Transfers" (at 796), "D. Locomotion" (at 798), "E. Communication" (at 800), and "F. Social Cognition" (at 802).

Figure 46:
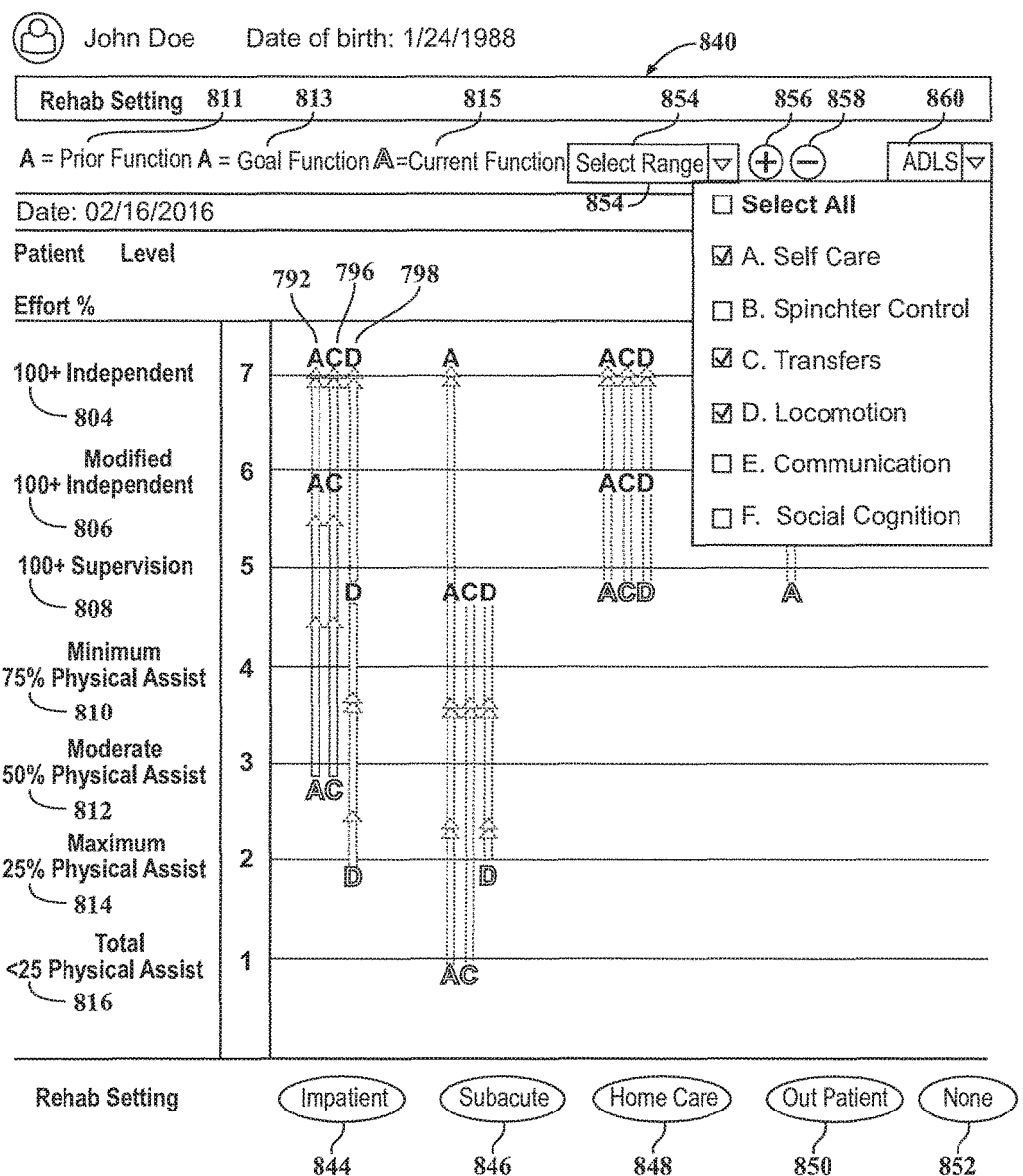
FIGS. 46-47 are rehabilitation setting screens depicting ranges in current, prior and goal function taken form the input screen of FIG. 45 and for use in determining metric performance ranges between total physical assist and independent.
Figure 47:
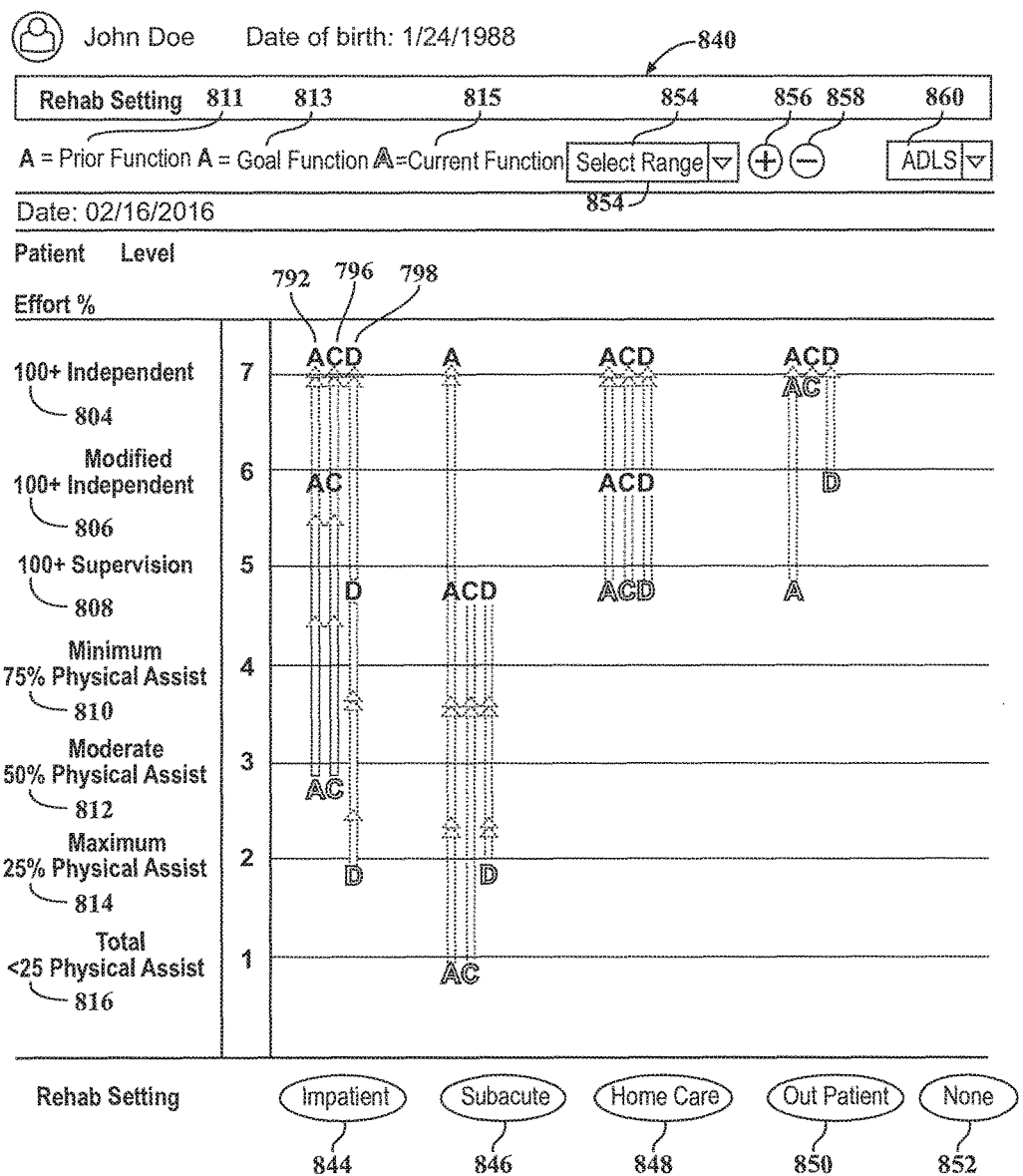

As indicated above, an effort rating is provided (see percentage gradations for each of 100+ (at 804 for Independent, 806 for Modified Independent and 808 for Supervision Independent), 75+ (at 810), 50+ (at 812), 25+ (at 814) and <25 (at 816) for each of discrete Current Function 811, Goal Function 813 and Prior Function 815 subset headings under each of A-F (792-802). The various subheadings also include comment and edit fields as appropriate and which enable the patient to input or supply necessary information for setting up the subsequent module screens. See also patient Yes/No queries 818-826 for such as "is patient willing to be in an in-patient rehab (at 818), a sub-acute rehab (at 820), does patient have cognition to follow therapy instructions (at 822), can patient sit for more than an hour in a chair (at 824), does patient have social support at home (at 826). Finally, field 828 provides for entering all acute diagnosis that the patient is actively being treated for, with add button 830. In this manner, both current function 832 and goal function 834 are listed with a difference between corresponding to a rehab functional gap 836. Submit button 838 is clicked to proceed to the next screens FIGS. 46-47 are rehabilitation setting screens, respectively at 840 and 842, depicting ranges in current, prior and goal function taken form the input screen of FIG. 45 and for use in determining metric performance ranges between total physical assist and independent. For each display, a range of variance between Prior, Goal and Current functions is shown for any selected subset of ADL functions (see again at 792, 796 and 798) and for each of Inpatient Rehab Setting 844, Subacute Rehab Setting 846, Home Care Rehab Setting 848, Out Patient Rehab Setting 850 and None 852. Also shown are drop down menus for each of Range, at 854 with +856 and -858 tabs, as well as ADL drop down menu 860 (e.g. again designating between Self Care and Social Cognition).

Figure 48A:
FIGS. 48A and 48B collectively depict a succeeding rehabilitation length of stay input screen contrasting current ability to goal ability and with the objective of establishing determined goals for achieving a maximum possible level of patient independence for each of self care, sphincter control, transfers, locomotion, communication and social cognition.
Figure 48B:
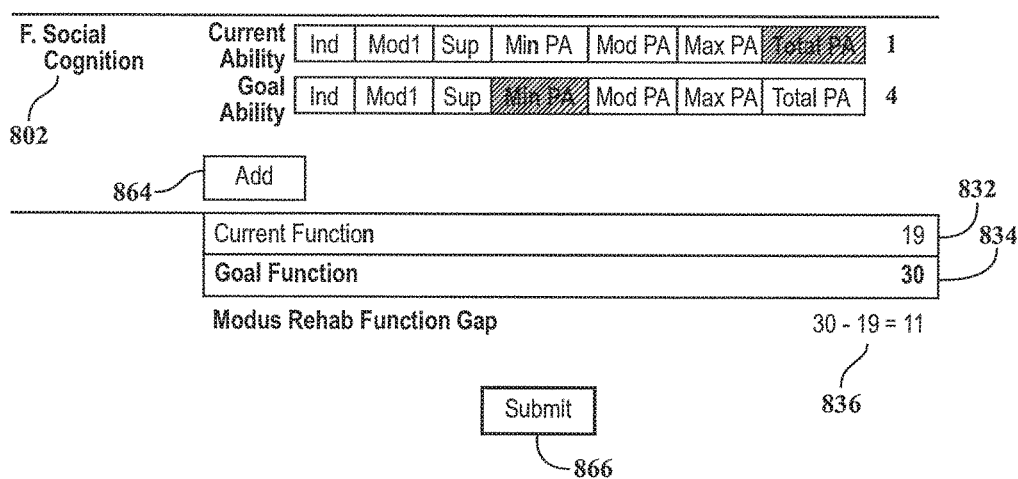

FIGS. 48A and 48B collectively depict a succeeding rehabilitation length of stay input screen, generally at 862 and corresponding largely to the inputs of screen 790 of FIG. 45, contrasting current ability to goal ability and with the objective of establishing determined goals for achieving a maximum possible level of patient independence for each of self-care 792, sphincter control 794, transfers 796, locomotion 798, communication 800 and social cognition 802. The metrics of FIG. 48 assist in estimating an anticipated length of stay of the patient using the same general algorithms as in the previous modules. Add button 864 again cumulates the current and goal function variables (at 832 and 834) in order to determine a rehab functional gap 836, with submit button 866 recording the information and advancing the module to the next screen.

Figure 49:
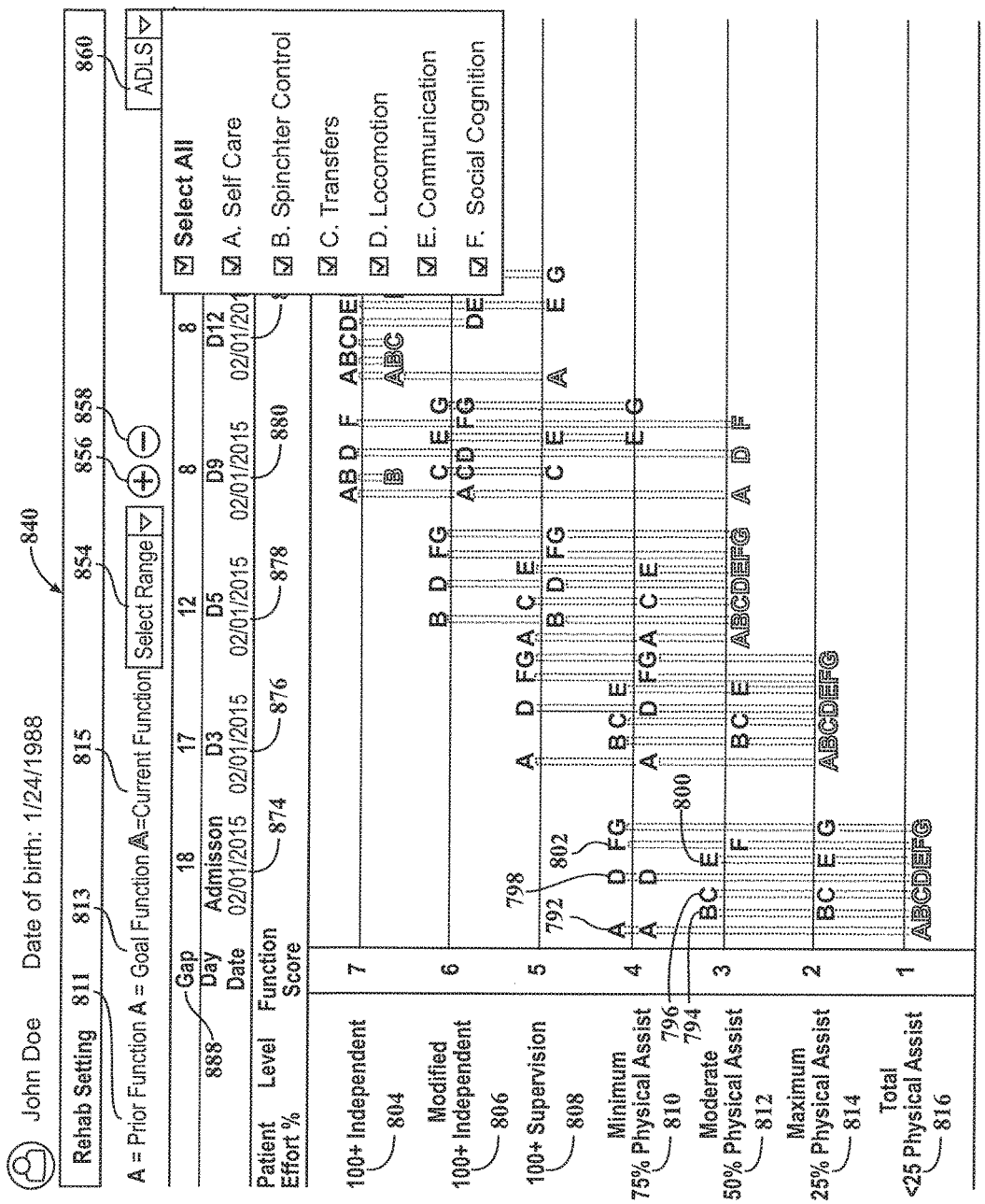
FIGS. 49-51 present a series of overlapping and time elapsed treatment and rehab length of stay screens which track the inter-ranges and adjustment/progress established between each of current function, goal function and prior function variables, with the objective being to close or eliminate the ranges over a time variable extending from date of admission (compare date of injury as in workman comp module) and date of discharge (compare further to date of return to work in prior module).
Figure 50:
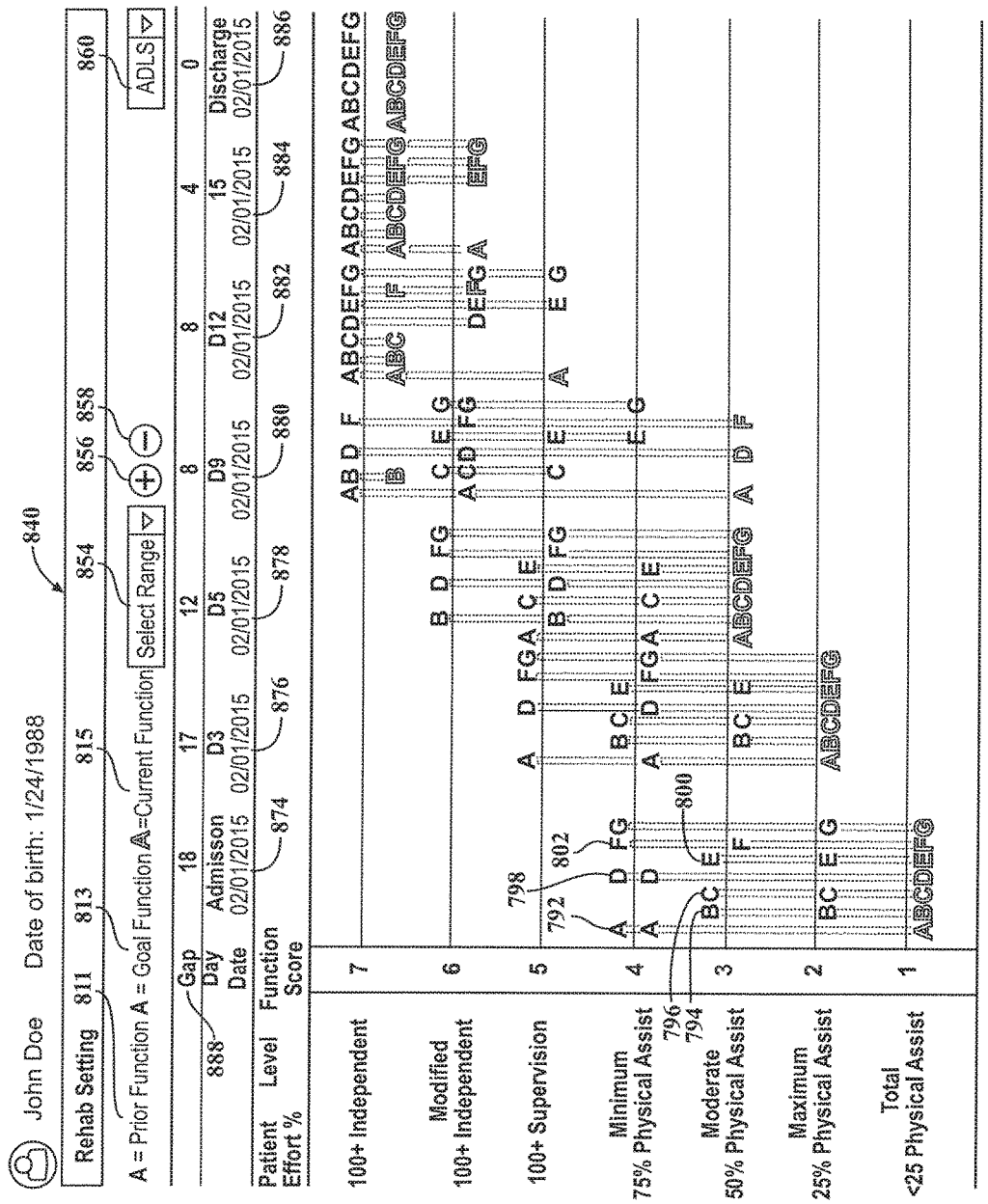
Figure 51:
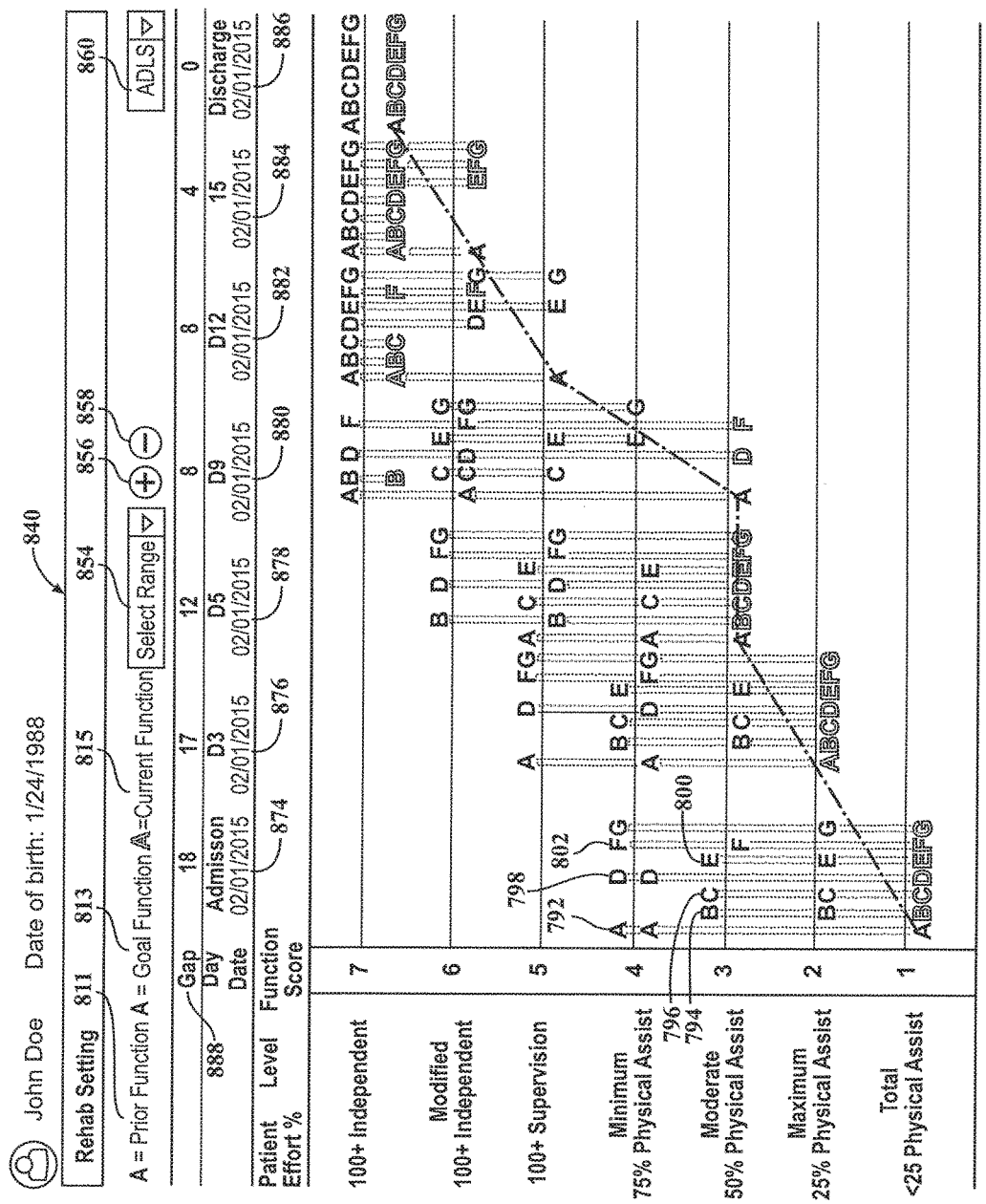

FIGS. 49-51 present a series of overlapping and time elapsed treatment and rehab length of stay screens, respectively at 868, 870 and 872, which track the inter-ranges and adjustment/progress established between each of the current function 815, goal function 813 and prior function 811 variables, with the objective being to close or eliminate the ranges over a time variable extending from date of admission 874, succeeding dates D3 876, D5 878, D9 880, D12, 882, D14 884 (compare date of injury as in workman comp module) and date of discharge 886 (compare further to date of return to work in prior module). Gap 888 column also provides a diminishing numerical variable (compare at 18 for Admission 874 to 0 at Discharge 886) which corresponds to the general closing of the ranges for each Function A-F 792-802.

Similar to FIG. 44, a graphical depiction (generally at 890) is provided for determining time interval components including each of 892 (Admission 874 to D3 876), 894 (D3 876 to D5 878), 896 (D5 878 to D9 880) denoting lack of improvement and necessitating a change in treatment, 898 (D9 880 to D12 882), 900 (D12 882 to D15 884) and, finally at 902 for D15 884 to Discharge 886. As with the workman comp module, the upward angle of the interval to interval graphical components is generally understood to correspond to the overall improvement of the patient in response to the treatment protocols prescribed according to the modules disclosed herein and concluding in the metrics of ADL's (see again 792, 794, 796, et seq.) between Prior, Current and Goal functions eventually closing to no range (at time of Discharge).

As with the previously disclosed variants, the above screen displays and protocols associated with the modules of FIGS. 23-44 and 45-51 can be integrated into subroutines associated with the non-transitory computer writeable medium, such as which is usable with a processor driven device for use in the treatment of an injured worker by a care provider, and in the instance of a worker further being involved in a workman compensation claim with an employer or payer.

A listing of such subroutines can include each of a first subroutine for assembling a provider network incorporating a best practices model (see again FIGS. 1-17) in the form of a database interfacing with the processor device and which presents series of treatment options associated with a given type of service, along with a fee schedule incentivizing the care provider in the achievement of a best functional outcome. A second subroutine is provided for training a plurality of the care providers in one or more of a series of medical related diagnosis and treatment programs consistent with the objectives of the first subroutine, the second subroutine further including establishing one or more management pathways which are customizable by the provider network and through establishing a questioning protocol for modifying or customizing a base algorithm for any one or more of a variety of treatment sub-species (see again FIGS. 18-22).

A third subroutine in the computer model may also include use by a supervisor designated by the employer/payer and which, upon the occurrence of an injury event, provides input of both worker biographical and detail of injury, with a fourth subroutine providing an assignment, by the provider network, of the care provider (such being the doctor in the area who is best suited for treating the patient as determined by screen illustration of FIG. 25). A fifth subroutine, upon an initial visit of the injured worker with the care provider, provides for confirmation by the worker of details previously provided by the supervisor and for the inputting of additional information and/or details surrounding the injury event.

A sixth subroutine can establish, by the worker with or without the assistance of the care provider, an electronic initial injury detail chart including at least one of a pictorial representation of a human form, along with inputs for symptoms relating to the injury event including type and intensity of pain. A seventh subroutine synthesizes all of the preceding subroutines in the establishment of a symptoms and treatment catalog over a duration of time extending from the injury event to an eventually determined end event corresponding to a recovery by the worker of a level of ability and function necessary for triggering a return to work event. Finally, an eighth subroutine provides for iterative treatment of the worker and updating the symptoms and treatment catalog, such occurring at determined time intervals following the injury event until the eventually determined end event.

Additional related subroutines include for determining, between the care provider, worker and employer/payer, a set of goals for achievement by the injured worker in triggering the return to work event. The afore-mentioned sixth subroutine may also include front and back pictorial depictions of a human form (see again FIG. 28 et seq.), the symptom inputs further including a listing of any of an aching pain, stabbing pain, burning pain or a numbness/tingling, along with either of a color or numerical intensity code.

Further consistent with the afore-described embodiments, a tenth worker ability input subroutine can be provided, occurring between the fifth and seventh subroutines, and listing a number of typical duties associated with a job of the worker, and for which the worker provides a current ability input. The current ability input of the tenth subroutine may also include a listing a point score for each duty as tied to any one of a minimum effort, moderate effort, severe effort, extreme effort and unable to perform, an accumulation of the points totaling a worker current ability.

Additional features of the eighth subroutine include a time interval comparison of the current ability and goals and corresponding to both treatment and changes in treatment derived from the first and second subroutines. Other features include synthesizing the worker ability input subroutine with the seventh and eighth subroutines in order to create an eleventh subroutine for determining, for each time interval, a range between worker inputted current ability and goal ability for each identified job duty.

Yet additional inputs include a twelfth subroutine for graphing a succession of time interval data points, each corresponding to an average of a current worker ability for the identified job duties, the care provider comparing an angle of inclination of the graph with the treatment protocols provided in the best practices model of the first subroutine and the management pathways of the second subroutine in the continued treatment of the worker according to the eighth subroutine.

As to the related rehabilitation module, a listing of the associated subroutines can similarly include a first subroutine for assembling a provider network incorporating a best practices model in the form of a database interfacing with the processor device and which presents series of treatment options associated with a given type of service, along with a fee schedule incentivizing the care provider in the achievement of a best functional outcome, with a second subroutine for training a plurality of the care providers in one or more of a series of medical related diagnosis and treatment programs consistent with the objectives of the first subroutine, the second subroutine further including establishing one or more management pathways which are customizable by the provider network and through establishing a questioning protocol for modifying or customizing a base algorithm for any one or more of a variety of treatment sub-species.

A third subroutine is provided for entering or synthesizing patient information including biographical and nature/type of condition associated with an event date, with a fourth subroutine for assignment, by the provider network, of a care provider for the treatment of the patient.

Additional inputs include a fifth rehabilitation setting input subroutine for establishing, by the patient with or without the assistance of the care provider, a listing of scaled efforts ranging independent to total physical assist and associated with a listing of patient ADL functions, such determinative of a present or future rehabilitative setting as recommended to the provider network. A sixth subroutine synthesizing all of the preceding subroutines in the establishment of a treatment and rehabilitation catalog over a duration of time extending from the event date to an eventually determined end event corresponding to an eventual final degree of recovery by the patient of a level of ability and function associated with an end rehabilitation setting. Finally, a seventh subroutine provides for iteratively treating the patient and updating the symptoms and treatment catalog, such occurring at determined time intervals following the event date until the eventually determined end date.

As to the rehabilitation module, additional inputs include an eighth rehabilitation subroutine for determining, between the care provider, patient and provider network, a set of goals for achievement by the patient in satisfying an established criteria for a given rehabilitation setting ranging from inpatient, subacute, home care, outpatient or none. The seventh subroutine can further include a time interval comparison of the current ability and goals and corresponding to both treatment and changes in treatment derived from the first and second subroutines Additional inputs include synthesizing the rehabilitation setting input subroutine with the sixth and seventh subroutines in order to create a ninth rehab setting subroutine for determining, for each time interval, a range between patient inputted prior function, current function and goal function for each identified ADL function. An eighth subroutine input proides for graphing a succession of time interval data points, each corresponding to an average of a patient ability for the identified ADL functions, the care provider comparing an angle of inclination of the graph with the treatment protocols provided in the best practices model of the first subroutine and the management pathways of the second subroutine in the continued treatment of the patient according to the seventh subroutine.

Numerous advantages associated with the present system include each of enabling patients and healthcare providers to input function in a simplified, accurate way, to create a date stamped and visually displayed record for patient function, such being displayed in an expanded or focused time chart, enabling medical providers to easily consume, to synthesize medical data, and take effective actions to improve outcomes, to simplify and standardize communications between patient, providers and healthcare managers/payers, to create a visual display of a patient's functional status and to visually identify gaps between current and desired/goal functions, and to accurately report the patient function, with savings incurred to both the provider and patient.

Other advantages associated with the symptoms/input catalog include savings in time and increased accuracy by avoiding asking and answering of duplicative questions and duplicative inputting of descriptions of patient symptoms, creating a date stamped visually displayed record for the patient's symptoms which is displaced in both expanded or focused time charts, enabling the medical providers to easily consume and synthesize medical data and take effective actions to improve outcomes. Other advantages include simplifying and standardizing communications between the patient, provider and healthcare managers/payers, creating a visual display of the patient's symptoms and visually identifying gaps between the current and desired or goal symptoms and, finally, accurately reporting with time savings to all parties.

Having described my invention, other and additional embodiments will become apparent to those skilled in the art to which it pertains and without deviating from the scope of the appended claims.

I claim:

1. A non-transitory software based algorithmic medium usable with a processor driven device for use in the treatment of an injured worker by a care provider through a graphical user interface, the injured worker further being involved in a workman compensation claim with an employer or payer, comprising:
    a first subroutine for assembling a provider network incorporating a best practices model in a database interfacing with the processor device and which presents series of treatment options associated with a given type of service, along with a fee schedule incentivizing the care provider in an achievement of a best functional outcome;
    a second subroutine, configured to be executed after the first subroutine, for training a plurality of the care providers in one or more of a series of medical related diagnosis and treatment programs consistent with objectives of the first subroutine, said second subroutine further including establishing one or more management pathways which are customizable by the provider network and through establishing a questioning protocol for modifying or customizing a base algorithm for any one or more of a variety of treatment subspecies;
    a third subroutine, configured to be executed after the second subroutine, for use by a supervisor designated by the employer/payer and which, upon occurrence of an injury event, provides input of both worker biographical and detail of injury;
    a fourth subroutine, configured to be executed after the third subroutine, for assignment, by the provider network, of the care provider;
    a fifth subroutine, configured to be executed after the fourth subroutine, which, upon an initial visit of the injured worker with the care provider, provides for confirmation by the injured worker of details previously provided by the supervisor and for: inputting of additional information, details surrounding the injury event, or both;
    a sixth subroutine, configured to be executed after the fifth subroutine, for establishing, by the injured worker, an electronic initial injury detail chart including a pictorial representation of a human form and inputs for symptoms relating to the injury event including type and intensity of pain;
    a seventh subroutine, configured to be executed after the sixth subroutine, for synthesizing all of the preceding subroutines in the establishment of a symptoms and treatment catalog over a duration of time extending from the injury event to an eventually determined end event corresponding to a recovery by the injured worker of a level of ability and function necessary for triggering a return to work event; and
    an eighth subroutine, configured to be executed after the seventh subroutine, for iteratively treating the injured worker and updating the symptoms and treatment catalog, such occurring at determined time intervals following the injury event until the eventually determined end event.

2. The non-transitory software based algorithmic medium of claim 1, further comprising a ninth subroutine for determining, between the care provider, worker and employer/payer, a set of goals for achievement by the injured worker in triggering the return to work event.

3. The non-transitory software based algorithmic medium of claim 2, said sixth subroutine further comprising front and back pictorial depictions of a human form, said symptom inputs further comprising listing of any of an aching pain, stabbing pain, burning pain or a numbness/tingling, along with either of a color or numerical intensity code.

4. The non-transitory software based algorithmic medium of claim 1, further comprising a tenth worker ability input subroutine, occurring between the fifth and seventh subroutines, and listing a number of typical duties associated with a job of the injured worker, and for which the injured worker provides a current ability input.

5. The non-transitory software based algorithmic medium of claim 4, said current ability input of the tenth subroutine further comprising listing a point score for each duty as tied to any one of a minimum effort, moderate effort, severe effort, extreme effort and unable to perform, an accumulation of the points totaling the injured worker's current ability.

6. The non-transitory software based algorithmic medium of claim 5, said eighth subroutine further comprising a time interval comparison of said current ability and goals and corresponding to both treatment and changes in treatment derived from the first and second subroutines.

7. The non-transitory software based algorithmic medium of claim 6, further comprising synthesizing said injured worker ability input subroutine with said seventh and eighth subroutines in order to create an eleventh subroutine for determining, for each time interval, a range between injured worker inputted current ability and goal ability for each identified job duty.

8. The non-transitory software based algorithmic medium of claim 7, further comprising a twelfth subroutine for graphing a succession of time interval data points, each corresponding to an average of a current injured worker ability for the identified job duties, the care provider comparing an angle of inclination of the graph with the treatment protocols provided in the best practices model of the first subroutine and the management pathways of the second subroutine in continued treatment of the injured worker according to the eighth subroutine.

9. A non-transitory software based algorithmic medium usable with a processor driven device utilizing a graphical user interface for use in the treatment and rehabilitation of a patient covered by a provider network, comprising:
   a first subroutine for assembling a provider network incorporating a best practices model in a database interfacing with the processor device and which presents series of treatment options associated with a given type of service, along with a fee schedule incentivizing the care provider in the achievement of a best functional outcome;
   a second subroutine, configured to be executed after the first subroutine, for training a plurality of the care providers in one or more of a series of medical related diagnosis and treatment programs consistent with objectives of the first subroutine, said second subroutine further including establishing one or more management pathways which are customizable by the provider network and through establishing a questioning protocol for modifying or customizing a base algorithm for any one or more of a variety of treatment subspecies;
   a third subroutine, configured to be executed after the second subroutine, for entering or synthesizing patient information including biographical and nature/type of condition associated with an event date;
   a fourth subroutine, configured to be executed after the third subroutine, for assignment, by the provider network, of a care provider for the treatment of the patient;
   a fifth rehabilitation setting input subroutine, configured to be executed after the fourth subroutine, for establishing, by the patient with or without assistance of the care provider, a listing of scaled efforts ranging independent to total physical assist and associated with a listing of patient ADL functions, such determinative of a present or future rehabilitative setting as recommended to the provider network;
   a sixth subroutine, configured to be executed after the fifth rehabilitation setting input subroutine, for synthesizing all of the preceding subroutines in establishing a treatment and rehabilitation catalog over a duration of time extending from the event date to an eventually determined end event corresponding to an eventual final degree of recovery by the patient of a level of ability and function associated with an end rehabilitation setting; and
   a seventh subroutine, configured to be executed after the sixth subroutine, for iteratively treating the patient and updating the symptoms and treatment catalog, such occurring at determined time intervals following the event date until an eventually determined end date.

10. The non-transitory software based algorithmic medium of claim 9, further comprising an eighth rehabilitation subroutine for determining, between the care provider, patient and provider network, a set of goals for achievement by the patient in satisfying an established criteria for a given rehabilitation setting ranging from inpatient, subacute, home care, outpatient or none.

11. The non-transitory software based algorithmic medium of claim 10, said seventh subroutine further comprising a time interval comparison of said current ability and goals and corresponding to both treatment and changes in treatment derived from the first and second subroutines.

12. The non-transitory software based algorithmic medium of claim 11, further comprising synthesizing said rehabilitation setting input subroutine with said sixth and seventh subroutines in order to create a ninth rehab setting subroutine for determining, for each time interval, a range between patient inputted prior function, current function and goal function for each identified ADL function.

13. The non-transitory software based algorithmic medium of claim 12, further comprising an eighth subroutine for graphing a succession of time interval data points, each corresponding to an average of a patient ability for the identified ADL functions, the care provider comparing an angle of inclination of the graph with the treatment protocols provided in the best practices model of the first subroutine and the management pathways of the second subroutine in continued treatment of the patient according to the seventh subroutine.

14. The non-transitory software based algorithmic medium of claim 3, wherein the front and back pictorial depictions of a human form further comprise displayed physiological location indicators based upon input received from the injured worker at a symptoms input graphical user interface.

* * * * *